US009533055B2

(12) United States Patent
Pardridge et al.

(10) Patent No.: US 9,533,055 B2
(45) Date of Patent: Jan. 3, 2017

(54) COMPOSITIONS AND METHODS FOR BLOOD-BRAIN BARRIER DELIVERY OF IGG-DECOY RECEPTOR FUSION PROTEINS

(75) Inventors: William M. Pardridge, Pacific Palisades, CA (US); Ruben J. Boado, Agoura Hills, CA (US)

(73) Assignee: ARMAGEN TECHNOLOGIES, INC., Calabasas, CA (US)

( * ) Notice: Subject to any disclaimer, the term of this patent is extended or adjusted under 35 U.S.C. 154(b) by 0 days.

(21) Appl. No.: 13/141,682

(22) PCT Filed: Mar. 18, 2010

(86) PCT No.: PCT/US2010/027882
§ 371 (c)(1),
(2), (4) Date: Aug. 31, 2011

(87) PCT Pub. No.: WO2010/108048
PCT Pub. Date: Sep. 23, 2010

(65) Prior Publication Data
US 2012/0269807 A1  Oct. 25, 2012

Related U.S. Application Data

(60) Provisional application No. 61/161,320, filed on Mar. 18, 2009.

(51) Int. Cl.
| C07K 16/28 | (2006.01) |
| A61K 47/48 | (2006.01) |
| A61K 38/00 | (2006.01) |
| A61K 39/00 | (2006.01) |

(52) U.S. Cl.
CPC ... *A61K 47/48276* (2013.01); *A61K 47/48623* (2013.01); *C07K 16/2869* (2013.01); *A61K 38/00* (2013.01); *A61K 2039/505* (2013.01); *C07K 2317/76* (2013.01); *C07K 2317/90* (2013.01); *C07K 2319/32* (2013.01)

(58) Field of Classification Search
None
See application file for complete search history.

(56) References Cited

U.S. PATENT DOCUMENTS

| 4,801,575 A | 1/1989 | Pardridge |
| 4,902,505 A | 2/1990 | Pardridge et al. |
| 4,946,778 A | 8/1990 | Ladner et al. |
| 5,154,924 A | 10/1992 | Friden |
| 5,180,820 A | 1/1993 | Barde et al. |
| 5,182,107 A | 1/1993 | Friden |
| 5,229,500 A | 7/1993 | Barde et al. |
| 5,438,121 A | 8/1995 | Barde et al. |
| 5,453,361 A | 9/1995 | Yancopoulos et al. |
| 5,527,288 A | 6/1996 | Gross et al. |
| 5,527,527 A | 6/1996 | Friden |
| 5,562,903 A | 10/1996 | Co et al. |
| 5,610,279 A * | 3/1997 | Brockhaus et al. ....... 530/387.3 |
| 5,618,920 A | 4/1997 | Robinson et al. |
| 5,656,284 A | 8/1997 | Balkin |
| 5,672,683 A | 9/1997 | Friden et al. |
| 5,693,762 A | 12/1997 | Queen et al. |
| 5,824,782 A | 10/1998 | Holzer et al. |
| 5,837,231 A | 11/1998 | Low et al. |
| 5,848,991 A | 12/1998 | Gross et al. |
| 5,977,307 A | 11/1999 | Friden et al. |
| 5,997,501 A | 12/1999 | Gross |
| 6,015,662 A | 1/2000 | Hackett |
| 6,041,775 A | 3/2000 | Century |
| 6,060,069 A | 5/2000 | Hill et al. |
| 6,153,190 A | 11/2000 | Young et al. |
| 6,165,783 A | 12/2000 | Weiss et al. |
| 6,201,105 B1 * | 3/2001 | Smith et al. ................. 530/350 |
| 6,248,262 B1 | 6/2001 | Kubotera et al. |
| 6,284,262 B1 | 9/2001 | Place |
| 6,287,792 B1 | 9/2001 | Pardridge et al. |
| 6,322,808 B1 | 11/2001 | Trautman et al. |
| 6,329,508 B1 | 12/2001 | Friden |
| 6,348,210 B1 | 2/2002 | Gale |
| 6,361,760 B1 | 3/2002 | Murata |
| 6,372,250 B1 | 4/2002 | Pardridge |
| 6,375,975 B1 | 4/2002 | Modi |
| 6,531,309 B1 | 3/2003 | Hu et al. |

(Continued)

FOREIGN PATENT DOCUMENTS

| EP | 0613007 A2 | 8/1994 |
| EP | 0613007 A3 | 10/1995 |

(Continued)

OTHER PUBLICATIONS

Aronovich et al., "Molecular Genetic Defect Underlying α-L-Iduronidase," Am. Journ. Hum. Genet. 58: 75-85 (1996).

Auclair, et al. Repeated intrathecal injections of recombinant human 4-sulphatase remove dural storage in mature mucopolysaccharidosis VI cats primed with a short-course tolerisation regimen. Mol Genet Metab. Feb. 2010;99(2):132-41. doi: 10.1016/j.ymgme.2009.10.002. Epub Oct. 13, 2009.

Begley et al., "Lysosomal storage diseases and the blood-brain barrier," Current Pharmaceutical Design, vol. 14, No. 16, pp. 1566-1580 (2008).

Boado et al., "Drug targeting of erythropoietin across the primate blood-brain barrier with an IgG molecular Trojan horse," Journal of Pharmacology and Experimental Therapeutics, vol. 333, No. 3, Jun. 1, 2010.

(Continued)

*Primary Examiner* — Marianne P Allen
(74) *Attorney, Agent, or Firm* — Wilson Sonsini Goodrich & Rosati

(57) ABSTRACT

Provided herein are compositions and related methods for delivering an IgG-decoy receptor to the CNS. The methods include systemic administration of a bifunctional decoy receptor-BBB receptor antibody fusion antibody comprising a receptor extracellular domain (ECD) covalently linked to an antibody to a receptor expressed on the surface of the blood-brain barrier (BBB receptor). In some embodiments, the compositions described herein are administered to treat a subject suffering from a CNS condition.

1 Claim, 14 Drawing Sheets

(56) References Cited

U.S. PATENT DOCUMENTS

| | | | |
|---|---|---|---|
| 6,541,610 B1 * | 4/2003 | Smith | 530/387.1 |
| 6,582,945 B1 | 6/2003 | Raso | |
| 6,583,272 B1 | 6/2003 | Bailon | |
| 6,709,833 B2 | 3/2004 | Fukui et al. | |
| 6,743,427 B1 | 6/2004 | Schenk | |
| 6,858,206 B2 | 2/2005 | Kakkis | |
| 7,053,202 B2 | 5/2006 | O'Keefe et al. | |
| 7,078,376 B1 | 7/2006 | Thompson | |
| 7,214,658 B2 * | 5/2007 | Tobinick | 424/134.1 |
| 7,226,758 B1 | 6/2007 | Lin et al. | |
| 7,294,704 B2 | 11/2007 | Simone et al. | |
| 7,309,687 B1 | 12/2007 | Brines et al. | |
| 7,388,079 B2 | 6/2008 | Pardridge et al. | |
| 8,486,399 B2 | 7/2013 | Pardridge et al. | |
| 8,715,661 B2 | 5/2014 | Pardridge et al. | |
| 8,741,260 B2 | 6/2014 | Pardridge et al. | |
| 8,753,610 B2 | 6/2014 | Pardridge et al. | |
| 8,759,297 B2 | 6/2014 | Pardridge et al. | |
| 8,834,874 B2 | 9/2014 | Pardridge et al. | |
| 8,920,801 B2 | 12/2014 | Pardridge et al. | |
| 8,974,791 B2 | 3/2015 | Pardridge et al. | |
| 2002/0052311 A1 | 5/2002 | Solomon et al. | |
| 2002/0137684 A1 | 9/2002 | Tchistiakova et al. | |
| 2002/0169109 A1 | 11/2002 | Plata-Salaman et al. | |
| 2003/0129186 A1 | 7/2003 | Beliveau et al. | |
| 2003/0165853 A1 | 9/2003 | Partridge et al. | |
| 2004/0043446 A1 | 3/2004 | DeFrees et al. | |
| 2004/0072291 A1 | 4/2004 | Carr et al. | |
| 2004/0101904 A1 | 5/2004 | Pardridge et al. | |
| 2004/0102369 A1 | 5/2004 | Wu et al. | |
| 2004/0229250 A1 | 11/2004 | Figura et al. | |
| 2004/0248197 A1 | 12/2004 | Holtzman et al. | |
| 2005/0142141 A1 | 6/2005 | Pardridge | |
| 2007/0031402 A1 | 2/2007 | Zhang et al. | |
| 2007/0081992 A1 | 4/2007 | Pardridge et al. | |
| 2007/0082380 A1 | 4/2007 | Pardridge et al. | |
| 2007/0275882 A1 | 11/2007 | Meijer et al. | |
| 2007/0280940 A1 | 12/2007 | Winkles et al. | |
| 2008/0003211 A1 | 1/2008 | Fogh et al. | |
| 2008/0051564 A1 | 2/2008 | Pardridge et al. | |
| 2008/0152645 A1 | 6/2008 | Pardridge et al. | |
| 2008/0170994 A1 | 7/2008 | Pardridge et al. | |
| 2008/0171055 A1 | 7/2008 | Pardridge et al. | |
| 2008/0292639 A1 | 11/2008 | Shen et al. | |
| 2009/0053219 A1 | 2/2009 | Pardridge et al. | |
| 2009/0068206 A1 | 3/2009 | Pardridge et al. | |
| 2009/0156498 A1 | 6/2009 | Pardridge et al. | |
| 2009/0238789 A1 | 9/2009 | Guyon et al. | |
| 2010/0077498 A1 | 3/2010 | Pardridge | |
| 2010/0098693 A1 | 4/2010 | Pardridge | |
| 2010/0172919 A1 | 7/2010 | Grimm et al. | |
| 2010/0261647 A1 | 10/2010 | Pardridge et al. | |
| 2010/0290985 A1 | 11/2010 | Pardridge et al. | |
| 2011/0110935 A1 | 5/2011 | Pardridge et al. | |
| 2012/0014936 A1 | 1/2012 | Natoli et al. | |
| 2012/0094934 A1 | 4/2012 | Collard et al. | |
| 2012/0269807 A1 | 10/2012 | Pardridge et al. | |
| 2013/0142794 A1 | 6/2013 | Pardridge et al. | |
| 2013/0287773 A1 | 10/2013 | Pardridge et al. | |
| 2014/0193409 A1 | 7/2014 | Pardridge et al. | |
| 2014/0288273 A1 | 9/2014 | Pardridge et al. | |
| 2014/0294822 A1 | 10/2014 | Pardridge et al. | |
| 2015/0004160 A1 | 1/2015 | Pardridge et al. | |
| 2015/0023956 A1 | 1/2015 | Pardridge et al. | |
| 2015/0064184 A1 | 3/2015 | Pardridge et al. | |
| 2015/0203586 A1 | 7/2015 | Pardridge et al. | |

FOREIGN PATENT DOCUMENTS

| | | |
|---|---|---|
| JP | 6-228199 | 8/1994 |
| WO | WO 99/00150 A2 | 1/1999 |
| WO | WO 99/00951 A1 | 1/1999 |
| WO | WO 99/00150 A3 | 4/1999 |
| WO | WO 99/66951 A1 | 12/1999 |
| WO | WO 00/15759 A1 | 3/2000 |
| WO | WO 00/37502 A2 | 6/2000 |
| WO | 0051621 A1 | 9/2000 |
| WO | WO 01/45730 A2 | 6/2001 |
| WO | WO 03/074081 A1 | 12/2003 |
| WO | WO-2004003019 A2 | 1/2004 |
| WO | WO 2004/050016 A2 | 6/2004 |
| WO | 2004108071 A2 | 12/2004 |
| WO | WO 2006/081171 A1 | 8/2006 |
| WO | WO 2007/022416 A2 | 2/2007 |
| WO | WO 2007/044323 A2 | 4/2007 |
| WO | WO 2007/022416 A3 | 5/2007 |
| WO | WO-2008-022349 | 2/2008 |
| WO | WO-2009-018122 | 2/2009 |
| WO | WO 2007/044323 A3 | 5/2009 |
| WO | WO 2009/070597 A2 | 6/2009 |
| WO | WO 2010/003101 * | 1/2010 |
| WO | 2011044542 A1 | 4/2011 |

OTHER PUBLICATIONS

Boado et al., "Genetic engineering of a lysosomal enzyme fusion protein for targeted delivery across the human blood-brain barrier," Biotechnology and Bioengineering, vol. 99, No. 2, pp. 475-484 (2008).

Boado et al., "IgG-single chain Fv fusion protein therapeutic for Alzheimer's disease: Expression in CHO cells and pharmacokinetics and brain delivery in the rhesus monkey," Biotechnology and Bioengineering, vol. 105, No. 3, pp. 627-635 (2010).

Boado et al., "Pharmacokinetics and brain uptake if a genetically engineered bifunctional fusion antibody targeting the mouse transferrin receptor," Molecular Pharmaceutics, vol. 7, No. 1, pp. 237-244 (2010).

Boado et al., Genetic Engineering of IgG-glucuronidase fusion proteins, J. Drug Targeting 18(3):205-11 (2010).

Degraaf, M. et al., "Expression of scFvs and scFv Fusion Proteins in Eukaryotic Cells." Methods in Biology, 2001, vol. 178: Antibody Phage Display: Methods and Protocols, p. 379-387.

Franco, et al. A cluster of sulfatase genes on Xp22.3: mutations in chondrodysplasia punctata (CDPX) and implications for warfarin embryopathy. Cell. Apr. 7, 1995;81(1):15-25.

Fu et al., "Neuroprotection in stroke in the mouse with intravenous erythropoietin-Trojan horse fusion protein," Brain Research, vol. 1369, Jan. 19, 2011.

Hui et al., "Tumor Necrosis Factor Receptor-IgG Fusion Protein for Targeted Drug Delivery across the Human Blood-Brain Barrier," vol. 6, No. 5, pp. 1536-1543 (2009).

Knaust, "Residues Critical for Formylglycine Formation and/or Catalytic Activity of Arylsulfatase A," American Chemical Society, 37:13941-13946 (1998).

Lu et al., "Expression in CHO Cells and Pharmacokinetics and Brain Uptake in the Rhesus Monkey of an IgG-Iduronate-2-Sulfatase Fusion Protein," Biotechnology and Bioengineering, vol. 108, No. 8, pp. 1954-1964 (2011).

Lu et al., "Genetic Engineering of a Bifunctional IgG fusion protein with iduronate-2-sulfatase," Bioconjugate Chemistry, 21(1) pp. 151-156 (2010).

Lukatela, et al. Crystal structure of human arylsulfatase A: the aldehyde function and the metal ion at the active site suggest a novel mechanism for sulfate ester hydrolysis. Biochemistry. Mar. 17, 1998;37(11):3654-64.

Nawashiro et al., "Neuroprotective effects of TNF binding protein in focal cerebral ischemia," Brain Research, vol. 778, No. 2, pp. 265-271 (1997).

NCBI GenBank Accession No. NM-000487 (Oct. 23, 2011).

Pardridge et al., "Biologic TNF[alpha]-inhibitors that cross the human blood-brain barrier," Bioengineered Bugs, Landes Bioscience, vol. 1, No. 4, pp. 231-234 (2010).

Pardridge et al., "Blood-brain barrier delivery of protein and non-viral gene therapeutics with molecular Trojan horses," Journal of Controlled Release, vol. 122, No. 3, pp. 345-348 (2007).

Pardridge, "Re-engineering biopharmaceuticals for delivery to brain with molecular Trojan horses," Bioconjugate Chemistry, vol. 18, No. 7, pp. 1327-1338 (2008).

(56) References Cited

OTHER PUBLICATIONS

Polito et al., "IDS Crossing of the Blood-Brain Barrier Corrects CNS Defects in MPSII Mice," Amer. Journ. Human Genetics, vol. 85, No. 2, pp. 296-301 (2009).
Schoonjans, R. et al., "Fab Chains as an Efficient Heterodimerization Scaffold for the Production of Recombinant Bispecific and Trispecific Antibody Derivatives." The Journal of Immunology, 2000, 165 (12): 7050-7057.
Tobinick et al., "Perispinal etanercept for neuroinflammatory disorders," Drug Discovery Today, vol. 14, No. 3-4, pp. 168-177 (2009).
Zhang, et al. 2003. Global Non-Viral Gene Transfer to the Primate Brain Following Intravenous Administration. Molecular Therapy 7 (1): 11-18.
Zhou, et al. Brain penetrating IgG-erythropoietin fusion protein is neuroprotective following intravenous treatment in Parkinson's disease in the mouse. Brain Res. Mar. 25, 2011;1382:315-20. Epub Jan. 26, 2011.
Zito, et al. Sulphatase activities are regulated by the interaction of sulphatase-modifying factor 1 with SUMF2, EMBO Rep 2005;6(7):655-660.
Barth et al. Boron neutron capture therapy of brain tumors: an emerging therapeutic modality. Neurosurgery. Mar. 1999;44(3):433-50; discussion 450-1.
Boado et al, Genetic engineering, expression, and activity of a fusion protein of a human neurotrophin and a molecular Trojan horse for delivery across the human blood-brain barrier. Biotechnology and Bioengineering. 2007;97:1376-1386.
Boado et al. Humanization of anti-human insulin receptor antibody for drug targeting across the human blood-brain barrier. Biotechnology and Bioengineering. 2007;96:381-391.
Boado, et al. Selective targeting of a TNFR decoy receptor pharmaceutical to the primate brain as a receptor-specific IgG fusion protein. J Biotechnol. Mar. 2010;146(1-2):84-91.
Brummell, et al. Probing the combining site of an anti-carbohydrate antibody by saturation-mutagenesis: role of the heavy-chain CDR3 residues. Biochemistry. 1993;32(4):1180-7.
Buchli, et al. Inhibition of Nogo: a key strategy to increase regeneration, plasticity and functional recovery of the lesioned central nervous system. Ann Med. 2005;37(8):556-67.
Coloma, et al. 1999. Transport Across the Primate Blood-Brain Barrier of a Genetically Engineered Chimeric Monoclonal Antibody to the Human Insulin Receptor. Pharmaceutical Research 17 (3): 266-274.
Coloma, et al. Design and production of novel tetravalent bispecific antibodies. Nat Biotechnol. Feb. 1997;15(2):159-63.
Coloma, et al. The hinge as a spacer contributes to covalent assembly and is required for function of IgG. J Immunol. Jan. 15, 1997;158(2):733-40.
Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.
Duchnowska, et al. Central nervous system metastases in breast cancer patients administered trastuzumab. Cancer Treat Rev. Jun. 2005;31(4):312-8.
Ferber, D. Bridging the blood-brain barrier: new methods improve the odds of getting drugs to the brain cells that need them. PLoS Biol. Jun. 2007;5(6):e169: 1191-1194.
Forough, et al. Differential transforming abilities of non-secreted and secreted forms of human fibroblast growth factor-1. J Biol Chem. Feb. 5, 1993;268(4):2960-8.
Lai, et al. Structural determinants of Trk receptor specificities using BDNF-based neurotrophin chimeras. J Neurosci Res. Dec. 1, 1996;46(5):618-29.
Marvin, et al. Recombinant approaches to IgG-like bispecific antibodies. Acta Pharmacol Sin. Jun. 2005;26(6):649-58.
McGrath, et al. Bifunctional fusion between nerve growth factor and a transferrin receptor antibody. J Neurosci Res. Jan. 15, 1997;47(2):123-33.

McLendon et al. Radiotoxicity of systemically administered 211At-labeled human/mouse chimeric monoclonal antibody: a long-term survival study with histologic analysis. Int J Radiat Oncol Biol Phys. Sep. 1, 1999;45(2):491-9.
Padlan, et al. Identification of specificity-determining residues in antibodies. FASEB J. 1995; 9(1):133-9.
Pardridge, et al. 1998, Combined Use of Carboxyl-Directed Protein Pegylation and Vector Mediated Blood-Brain Barrier Drug Delivery System Optimizes Brain Uptake of Brain-Derived Neurotrophic Factor Following Intravenous Administration. Pharmaceutical Research 15 (4): 576-582.
Park, et al. Production and characterization of fusion proteins containing transferrin and nerve growth factor. J Drug Target. 1998;6(1):53-64.
Raghavan, et al. Analysis of the pH dependence of the neonatal Fc receptor/immunoglobulin G interaction using antibody and receptor variants. Biochemistry. Nov. 14, 1995;34(45):14649-57.
Schlachetzki, et al. Expression of the neonatal Fc receptor (FcRn) at the blood-brain barrier. J Neurochem. Apr. 2002;81(1):203-6.
Triguero et al. Capillary depletion method for quantification of blood-brain barrier transport of circulating peptides and plasma proteins. J Neurochem. 1990; 54(6):1882-8.
Zhang, et al. Mediated efflux of IgG molecules from brain to blood across the blood-brain barrier. J Neuroimmunol. Mar. 1, 2001;114(1-2):168-72.
Aharoni, et al. Directed evolution of mammalian paraoxonases PON1 and PON3 for bacterial expression and catalytic specialization. Proc Natl Acad Sci U S A. Jan. 13, 2004;101(2):482-7. Epub Dec. 26, 2003.
Ai, et al., 2003. Intraputamenal Infusion of GDNF in Aged Rhesus Monkeys: Distribution and Dopaminergic Effects. The Journal of Comparative Neurology 461: 250-261.
Airavaara, et al. Effects of repeated morphine on locomotion, place preference and dopamine in heterozygous glial cell line-derived neurotrophic factor knockout mice. Genes Brain Behav. Apr. 2007;6(3):287-98.
Al Sawaf, et al. Neurological findings in Hunter disease: pathology and possible therapeutic effects reviewed, J Inherit Metab Dis. Aug. 2008:31(4):473-80.
Albayrak, et al. Effect of transient focal ischemia on blood-brain barrier permeability in the rat: Correlation to Cell Injury. Acta Neuropathol 1997;94:158-63.
Alberts, et al. Molecular Biology of the Cell. 3rd Edition. Garland Publishing Inc. New York. 1994; pp. 1206-1207.
Altschul, et al. Optimal sequence alignment using affine gap costs. Bulletin of Mathematical Biology. 1966; 48(5-6):603-16.
Altschul, et al. Basic Local Alignment Search Tool. J. Mol. Biol. 1990;215:403-410.
Altschul, et al. Gapped BLAST and PSI-BLAST: a new generation of protein database search programs. Nucleic Acids Res. 1977;25:3389-402.
Arndt, et al. Generation of a highly stable, internalizing anti-CD22 single-chain Fv fragment for targeting non-Hodgkin's lymphoma. Int J Cancer. Dec. 10, 2003;107(5):822-829.
Bachis, et al. 2003. Brain-Derived Neurotropic Factor Inhibits Human Immunodeficiency Virus-1/gp 120-Mediated Cerebellar Granule Cell Death by Preventing gp 120 Internalization. The Journal of Neuroscience 23 (13): 5712-22.
Baloh, et al. Functional mapping of receptor specificity domains of glial cell line-derived neurotrophic factor (GDNF) family ligands and production of GFRalpha1 RET-specific agonists. J Biol Chem. Feb. 4, 2000;275(5):3412-20.
Batzer, et al. Enhanced evolutionary PCR using oligonucleotides with inosine at the 3'-terminus. Nucleic Acid Res.1991;19:5081.
Beck, et al. Brain-Derived Neurotrophic Factor Protects Against Ischemic Cell Damage in Rat Hippocampus. Journal of Cerebral Blood Flow and Metabolism 1994. 14: 689-92.
Bifare, et al. Brain-Derived Neurotrophic Factor Protects against Multiple Forms of Brain Injury in Bacterial Meningitis. 2005. The Journal of Infectious Diseases 191: 40-45.
Boado et al. Fusion Antibody for Alzheimer's Disease with Bi-Directional Transport Across the Blood-Brain Barrier and Abeta Fibril Disaggregation. Bioconjug Chem. 2007;18(2):447-55.

(56) References Cited

OTHER PUBLICATIONS

Boado, et al, Genetic engineering, expression, and activity of a fusion protein of a human neurotrophin and a molecular Trojan horse for delivery across the human blood-brain barrier. Biotechnology and Bioengineering. 2007;97:1376-86.
Boado, et al. AGT-181: expression in CHO cells and pharmacokinetics, safety, and plasma iduronidase enzyme activity in Rhesus monkeys. Oct. 2009; 144(2):135-41.
Boado, et al. CHO cell expression, long-term stability, and primate pharmacokinetics and brain uptake of an IgG-paraoxonase-1 fusion protein. Biotechnol Bioeng. Jan. 2011;108(1):186-96.
Boado, et al. Drug delivery of antisense molecules to the brain for treatment of Alzheimer's disease and cerebral AIDS. J Pharm Sci. Nov. 1998;87(11):1308-15.
Boado, et al. Engineering and expression of a chimeric transferrin receptor monoclonal antibody for blood-brain barrier delivery in the mouse. Biotechnol Bioeng. Mar. 1, 2009;102(4):1251-8.
Boado, et al. GDNF fusion protein for targeted-drug delivery across the human blood-brain barrier. Biotechnol Bioeng. Jun. 1, 2008;100(2):387-96.
Boado, et al, Genetic engineering of a lysosomal enzyme fusion protein for targeted delivery across the human blood-brain barrier. Biotechnology and Bioengineering. 2008;99:475-84.
Boado, et al. Reversal of lysosomal storage in brain of adult MPS-I mice with intravenous Trojan horse-iduronidase fusion protein. Mol Pharm. Aug. 1, 2011;8(4):1342-50. Epub Jun. 17, 2011.
Braun, et al. Metabolic correction and cross-correction of mucopolysaccharidosis type II (Hunter syndrome) by retroviral-mediated gene transfer and expression of human iduronate-2-sulfatase. Proc Natl Acad Sci 1993;90:11830-11834.
Brines, et al. Erythropoietin crosses the blood-brain barrier to protect against experimental brain injury, Proc Natl Acad Sci USA. 2000; 97:10526-10531.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Carnicella, et al. GDNF is a fast-acting potent inhibitor of alcohol consumption and relapse. Proc Natl Acad Sci U S A. Jun. 10, 2008;105(23):8114-9.
Casset, et al. A peptide mimetic of an anti-CD4 monoclonal antibody by rational design. Biochem Biophys Res Commun. Jul. 18, 2003;307(1):198-205.
Cassol, et al. Stability of dried blood spot specimens for detection of human immunodeficiency virus DNA by polymerase chain reaction. J Clin Microbial. Dec. 1992;30(12):3039-42.
Chen, et al. In vitro scanning saturation mutagenesis of all the specificity determining residues in an antibody binding site. Protein Engineering. 1999; vol. 12, No. 4, 349-56.
Cheng, et al. 1997. Marked Age-dependent Neuroprotection by Brain-derived Neurotropic Factor Against Neonatal Hypoxic-Ischemic Brain Injury. Annals of Neurology 41 (4): 521-29.
Cheng, et al. 2004. Neuroprotection for Ischemic Stroke: Two Decades of Success and Failure. The Journal of the American Society for Experimental Neuro Therapeutics 1: 36-45.
Chothia, et al. Canonical structures for the hypervariable regions of immunoglobulins. J Mol Biol. Aug. 20, 1987;196(4):901-17.
Chung et al, Antibodies against West Nile Virus nonstructural protein NS1 prevent lethal infection through Fc gamma receptor-dependent and -independent mechanisms. J Virol. Feb. 2006;80(3):1340-51.
Colman, P.M. Effects of amino acid sequence changes on antibody-antigen interactions, Res Immunol. Jan. 1994:145(1):33-6.
Cowen, et al. Neuropeptides: implications for alcoholism. Journal of Neurochemistry. 2004. 89: 273-85.
Crow, et al. Biochemical and histopathological studies on patients with mucopolysaccharidoses, two of whom had been treated by fibroblast transplantation. J Clin Pathol. 1983;36(4):415-30.

Dawson, et al. 2001. A comparative assessment of the efficacy and side-effect liability of the neuroprotective compounds in experimental stroke. Brain Research 892: 344-50.
De Pascalis, et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Deakin, et al. Enzymatically active paraoxonase-1 is located at the external membrane of producing cells and released by a high affinity, saturable, desorption mechanism. J Biol Chem. Feb. 8, 2002;277(6):4301-8. Epub Nov. 28, 2001.
Deane, at al. IgG-assisted age-dependent clearance of Alzheimer's amyloid beta peptide by the blood-brain barrier neonatal Fc receptor. J Neurosci. 2005;25(50):11495-503.
Dreier, et al. Recombinant immunocytokines targeting the mouse transferrin receptor: construction and biological activities. Bioconjug Chem. Jul.-Aug. 1998;9(4):482-9.
Duffy, et al. 1987. Blood-brain barrier transcytosis of insulin in developing rabbits. Brain Research 420: 32-38.
Duffy, et al. 1988. Human blood-brain barrier insulin-like growth factor receptor. Metabolism. Feb;37(2):136-40.
Durrington, et al. Paraoxonase and atherosclerosis. Arterioscler Thromb Vasc Biol. Apr. 2001;21(4):473-80.
Ehrenreich, et al. Erythropoietin therapy for acute stroke is both safe and beneficial. Mol Med. Aug. 2002;8(8):495-505.
Eketjall, et al. Distinct structural elements in GDNF mediate binding to GFRalpha1 and activation of the GFRalpha1-c-Ret receptor complex. EMBO J. Nov. 1, 1999;18(21):5901-10.
Elliott, et al. Control of rHuEPO biological activity: the role of carbohydrate. Exp Hematol. Dec. 2004;32(12):1146-55.
Eslamboli, et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. J. Neurosci. 2005:25:769-77.
Fillebeen, et al. Receptor-mediated transcytosis of lactoferrin through the blood-brain barrier. J Biol Chem. Mar. 12, 1999;274(11):7011-17.
Flowmen, et al. Determination of the organisation of coding sequences within the iduronate sulphate sulphatase (IDS)gene. Hum. Mol. Genet. 1993;2(1):5-10.
Frenkel, et al. Modulation of Alzheimer's beta-amyloid neurotoxicity by site-directed single-chain antibody. J Neuroimmunol. Jul. 1, 2000;106(1-2):23-31.
Friden, et al. Blood-brain barrier penetration and in vivo activity of an NGF conjugate. Science. Jan. 15, 1993;259(5093):373-77.
Fu, et al. Neuroprotection in stroke in the mouse with intravenous erythropoietin-Trojan horse fusion protein. Brain Res. Jan. 19, 2011;1369:203-7. Epub Oct. 31, 2010.
Fukuchi, et al. Amelioration of amyloid load by anti-Abeta single-chain antibody in Alzheimer mouse model. Biochem Biophys Res Commun. May 26, 2006;344(1):79-86.
Fukuda et al. In vitro evolution of single-chain antibodies using mRNA display. Nucleic Acids Research, 2006; 34(19):e127.
Gillies, et al. Bi-functional cytokine fusion proteins for gene therapy and antibody-targeted tratment of cancer. 2002, Cancer Immunology and Immunotherapy, vol. 51, pp. 449-460.
Golden, et al. Human blood-brain barrier leptin receptor. Binding and endocytosis in isolated human brain microvessels. J Clin Invest. Jan. 1, 1997;99(1):14-8.
Grasso, et al. Neuroprotection by erythropoietin administration after experimental traumatic brain injury. Brain Res. Nov. 28, 2007:1182:99-105.
Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003:18(7):2093-8.
Habgood, et al. Changes in blood-brain barrier permeability to large and small molecules following traumatic brain injury in mice. Eur J Neurosci. Jan. 2007;25(1):231-8.

(56) References Cited

OTHER PUBLICATIONS

Haisma, et al. Construction and characterization of a fusion protein of single-chain anti-CD20 antibody and human beta-glucuronidase for antibody-directed enzyme prodrug therapy. Blood. Jul. 1, 1998;92(1):184-90.

Hansson et al. Prediction of Alzheimer's disease using the CSF Abeta42/Abeta40 ratio in patients with mild cognitive impairment. Dement Geriatr Cogn Disord. 2007;23(5):316-20.

He, et al. Autoregulation of glial cell line-derived neurotrophic factor expression: implications for the long-lasting actions of the anti-addiction drug, Ibogaine. FASEB J. Nov. 2006;20(13):E1820-E1827; 2420-22.

He, et al. Glial cell line-derived neurotrophic factor mediates the desirable actions of the anti-addiction drug ibogaine against alcohol consumption. J Neurosci. Jan. 19, 2005;25(3):619-28.

He, et al. Identification and characterization of the molecular lesion causing mucopolysaccharidosis type I in cats. Mol Genet Metab. 1999; 67(2):106-12.

Henikoff et al. Predicting the effects of amino Acid substitutions on protein function. Annu Rev Genomics Hum Genet. 2006;7:61-80.

Henikoff, et al. Amino acid substitution matrices from protein blocks. Proc Natl Acad Sci U S A. 1992; 89(22):10915-9.

Hetman, et al. 1999. Neuroprotection by Brain-derived Neurotropic Factor Is Mediated by Extracellular Signal-regulated Kinase and Phoshatidylinositol 3-Kinase. The J of Bio Chem 274 (32): 22569-80.

Holliger, et al. Engineered antibody fragments and the rise of single domains. Nat Biotechnol. Sep. 2005;23(9):1126-36.

Hoshaw, et al. 2005. Central administration of IGF-I and BDNF leads to long-lasting antidepressant-like effects. Brain Research 1037: 204-8.

Huston, et al. Protein engineering of antibody binding sites: recovery of specific activity in an anti-digoxin single-chain Fv analogue produced in *Escherichia coli*. Proc Natl Acad Sci U S A. 1988; 85(16):5879-83.

Ibanez, et al. An extended surface of binding to Trk tyrosine kinase receptors in NGF and BDNF allows the engineering of a multifunctional pan-neurotrophin. EMBO J. Jun. 1993;12(6):2281-93.

Ibanez, Structure-function relationships in the neurotrophin family. J Neurobiol. Nov. 1994;25(11):1349-61.

Iwasaki, et al. Protective effect of interleukin-3 and erythropoietin on motor neuron death after neonatal axotomy. Neural Res. Oct. 2002;24(7):643-6.

Jefferies, et al. Analysis of lymphopoietic stem cells with a monoclonal antibody to the rat transferrin receptor. Immunology. Feb. 1985;54(2):333-41.

Jethwa, et al. 2004. Neuromedin U has a physiological role in the regulation of food intake and partially mediates the effects of leptin. American Journal of Physiology—Endocrinology and Metabolism 289: E301-E305.

Jiang, et al. 2005. BDNF Variation and Mood Disorders: A Novel Functional Promoter Polymorphism and Val66Met are Associated with Anxiety but Have Opposing Effects. Neuropsychopharmacology 30: 1353-61.

Josse, et al. Identification of residues essential for human paraoxonase (PON1) arylesterase/organophosphatase activities. Biochemistry. Mar. 2, 1999;38(9):2816-25.

Josse, et al. Oligomeric states of the detergent-solubilized human serum paraoxonase (PON1). J Biol Chem. Sep. 6, 2002;277(36):33386-97.

Josse, et al. The active site of human paraoxonase (PON1). J Appl Toxicol. Dec. 2001;21 Suppl 1:S7-11.

Juul, et al. Erythropoietin concentrations in cerebrospinal fluid of nonhuman primates and fetal sheep following high-dose recombinant erythropoietin, Biol. Neonate. 2004;85:138-144.

Kabat, et al., Sequences of Proteins of Immunological Interest. 5th Ed. Public Health Service, National Institutes of Health, Bethesda, Md. 1991;pp. 647-649.

Kakkis, et al. Overexpression of the human lysosomal enzyme alpha-L-iduronidase in Chinese hamster ovary cells. Protein Expr Purif. 1994; 5(3):225-32.

Karlin, et al. Applications and statistics for multiple high-scoring segments in molecular sequences. Proc. Natl. Acad. Sci. USA. 1993;90:5873-87.

Kashmiri, et al. SDR grafting—a new approach to antibody humanization. Methods. May 2005;36(1):25-34.

Kastin, et al. Glial cell line-derived neurotrophic factor does not enter normal mouse brain. Neuroscience Letters. 2003;340:239-41.

Kido, et al. 2000. Neuroprotective effects of brain-derived neurotropic factor in eyes with NMDA-induced neuronal death. Brain Research 884:59-67.

Kim, et al. Decreased paraoxonase-1 activity is a risk factor for ischemic stroke in Koreans. Biochem Biophys Res Commun. Dec. 7, 2007;364(1):157-62.

Kim, et al., Continuous Brain-derived Neurotropic Factor (BDNF) Infusion After Methylprednisolone Treatment in Severe Spinal Cord Injury. Journal of Korean Medical Science 2003;19: 113-22.

Kitagawa, et al. Reduction of Ischemic Brain Injury by Topical Application of Glial Cell Line-Derived Neurotrophic Factor After Permanent Middle Cerebral Artery Occlusion in Rats. Stroke. 1998;29:1417-22.

Kobayashi, et al. Intracerebral Infusion of Glial Cell Line-Derived Neurotrophic Factor Promotes Striatal Neurogenesis After Stroke in Adult Rats Stroke. 2006;37:2361-67.

Koehne, et al. Vascular endothelial growth factor and erythropoietin concentrations in cerebrospinal fluid of children with hydrocephalus. Childs Nerv Syst. Apr. 2002;18(3-4):137-41.

Krewson, et al. 1995. Distribution of nerve growth factor following direct delivery to brain interstitium. Brain Research 680: 196-206.

Kurihara, et al. 1999. Imaging Brain Tumors by Targeting Peptide Radiopharmaceuticals through the Blood-Brain Barrier. Cancer Research 59: 6159-63.

Lang, et al. Randomized controlled trial of intraputamenal glial cell line-derived neurotrophic factor infusion in Parkinson disease. Annals of Neurology. 2006;59:459-66.

Lapchak, et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. Neuroscience. 1997;78:61-72.

Lazar, et al. Transforming growth factor alpha: mutation of aspartic acid 47 and leucine 48 results in different biological activities. Mol Cell Biol. Mar. 1988;8(3):1247-52.

Lee, et al. Drug targeting to the brain using avidin-biotin technology in the mouse; (blood-brain barrier, monoclonal antibody, transferrin receptor, Alzheimer's disease). J Drug Target. 2000;8(6):413-24.

Lee, et al., Imaging Brain Amyloid of Alzheimer Disease In Vivo in Transgenic Mice With an Aβ Peptide Radiopharmaceutical. Journal of Cerebral Blood Flow and Metabolism 2002;22: 223-31.

Lenz, et al. Stoichiometric and catalytic scavengers as protection against nerve agent toxicity: a mini review. Toxicology. Apr. 20, 2007;233(1-3):31-9.

Lewin, B. Genes IV. Oxford University Press. 1990. p. 810.

Li, et al. Genetically engineered brain drug delivery vectors: cloning, expression and in vivo application of an anti-transferrin receptor single chain antibody-streptavidin fusion gene and protein. Protein Eng. Sep. 1999;12(9):787-96.

Lin, et al. GDNF: a glial cell line-derived neurotrophic factor for midbrain dopaminergic neurons. Science. 1993;260:1130-32.

Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.

Liu, et al. Anti beta-amyloid (Abets) SCFV inhibits Abeta aggregation and neurotoxicity (P4-354). Neurobiology of Aging, Tarrytown, NY. 2004;25:S575-S576.

Liu, et al. Single chain variable fragments against beta-amyloid (Abeta) can inhibit Abeta aggregation and prevent abeta-induced neurotoxicity. Biochemistry. Jun. 8, 2004;43(22):6959-67.

Lu, et al. Cationic Liposome-Mediated GDNF Gene Transfer after Spinal Cord Injury. Journal of Neurotrauma. 2002;19:1081-1090.

(56) References Cited

OTHER PUBLICATIONS

Ma, et al. Erythropoietin protects PC12 cells from beta-amyloid(25-35)-induced apoptosis via PI3K/Akt signaling pathway. Neuropharmacology. May-Jun. 2009;56(6-7):1027-34.

MacCallum, et al. Antibody-antigen interactions: contact analysis and binding site topography. J Mol Biol. Oct. 11, 1996;262(5):732-45.

Manoutcharian, et al. Amyloid-beta peptide-specific single chain Fv antibodies isolated from an immune phage display library. J Neuroimmunol. 2003; 145(1-2):12-7.

Martell, et al. Efficacy of transferrin receptor-targeted immunotoxins in brain tumor cell lines and pediatric brain tumors. Cancer Res, Mar. 15, 1993;53(6):1348-53.

Martin et al. Crystal structure at 2.8 A of an FcRn/heterodimeric Fc complex: mechanism of pH-dependent binding. Mol Cell. Apr. 2001;7(4):867-77.

Matis, et al. Erythropoietin in spinal cord injury. Eur Spine J. Mar. 2009;18(3):314-23.

Menzies, et al. 1993. Contributions of ions and albumin to the formations and resolution of ischemic brain edema. Journal of Neurosurgery 78: 257-266.

Messer, et al. Role for GDNF in biochemical and behavioral adaptations to drugs of abuse. Neuron. Apr. 2000;26(1):247-57.

Mori, et al. 2004. Differential expression patterns of TrkB ligands in the macaque monkey brain. Developmental Neuroscience 15: 2507-11.

Muenzer, et al. A phase II/III clinical study of enzyme replacement therapy with idursulfase in mucopolysaccharidosis II (Hunter syndrome). Genet Med Aug. 2006;8(8):465-73.

Muenzer, et al. Advances in the treatment of mucopolysaccharidosis type I. N Engl J Med. May 6, 2004;350(19):1932-4.

NCBI Reference Sequence: NM-000202.5 *Homo sapiens* iduronate 2-sulfatase (IDS), transcript variant 1, mRNA. 1992. http://www.ncbi.nlm.nih.gov/nuccore/NM000202.5.

Needleman, et al, A general method applicable to the search for similarities in the amino acid sequence of two proteins. J. Mol. Biol. 1970;48:443-53.

Ng, et al. Paraoxonase-1 deficiency in mice predisposes to vascular inflammation, oxidative stress, and thrombogenicity in the absence of hyperlipidemia. Cardiovasc Pathol. Jul.-Aug. 2008;17(4):226-32.

Ng, et al. Predicting the effects of amino acid substitutions on protein function. Annual Review of Genomics and Human Genetics. 2006;7:61-80.

Nutt, et al., Randomized, double-blind trial of glial cell line-derived neurotropic factor (GDNF) in PD. Neurology 2003;60: 69-73.

Ober, et al. Differences in promiscuity for antibody-FcRn interactions across species: implications for therapeutic antibodies. Int Immunol. Dec. 2001;13(12):1551-9.

Ohtsuka, et al. An alternative approach to deoxyoligonucleotides as hybridization probes by insertion of Deoxyinosine at Ambiguous Codon Positions. J. Biol. Chem. 1985;260:2605-08.

Osbourn, et al. Directed selection of MIP-1 alpha neutralizing CCR5 antibodies from a phage display human antibody library. Nat Biotechnol. Aug. 1998;16(8):778-81.

Padlan, et al. Structure of an antibody-antigen complex: crystal structure of the HyHEL-10 Fab-lysozyme complex. Proc Natl Acad Sci U S A. Aug. 1989;86(15):5938-42.

Paragh, et al. Ciprofibrate increases paraoxonase activity in patients with metabolic syndrome. Br J Clin Pharmacol. Jun. 2006;61(6):694-701.

Pardridge, 2001. Brain drug targeting: The future of brain drug development. Cambridge University Press.

Pardridge, 2001. Neuroprotection in stroke: is it time to consider large-molecule drugs? Drug Discovery Today 6: 751-53.

Pardridge, 2002. Neurotrophins, neuroprotection and the blood-brain barrier. Current Opinion in Investigational Drugs 3 (12): 1753-57.

Pardridge, 2003. Blood-Brain Barrier Drug Targeting: The Future of Brain Drug Development. Molecular Interventions 3: 90-105.

Pardridge, 2005. The Blood-Brain Barrier and Neurotherapeutics. NeuroRx: The Journal of the American Society for Experimental NeuroTherapeutics 2 (1): 1-2.

Pardridge, 2005. The Blood-Brain Barrier: Bottleneck in Brain Drug Development. NeuroRx: The Journal of the American Society for Experimental NeuroTherapeutics 2: 3-14.

Pardridge, 2005. Tyrosine Hydroxylase Replacement in Experimental Parkinson's Disease with Transvascular Gene Therapy. NueuoRx: Journal of the American Society for Experimental NeuroTherapeutics. 2(1):129-138.

Pardridge, 2007. Drug Targeting to the Brain. Pharm Res 24:1733-44.

Pardridge, et al. 1987. Human Blood-Brain Barrier Transferrin Receptor. Metabolism 36: 892-95.

Pardridge, et al. 1989. Transport of histone through the blood-brain barrier. J Pharmacol Exp Ther. Dec;251(3):821-6.

Pardridge, et al. 1993. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-46.

Pardridge, et al. 1995 Human insulin receptor monoclonal antibody undergoes high affinity binding to human brain capillaries in vitro and rapid transcytosis through the blood-brain barrier in vivo in the primate. Pharm Res. 12(6):807-16.

Pardridge, et al. Drug and gene targeting to the brain with molecular Trojan horses. Nat Rev Drug Discov. Feb. 2002;1(2):131-9.

Patel, et al. Intraputamenal infusion of glial cell line-derived neurotrophic factor in PD: A two-year outcome study. Annals of Neurology. 2005;57:298-302.

Paul, W. Fundamental Immunology. 3rd Edition. 1993;292-95.

Pearson, et al. Improved Tools for Biological Sequence Comparison. Proc. Nat'l Acad. Sci. USA. 1988;85:2444-48.

Pearson, Rapid and sensitive sequence comparison with FASTP and FASTA. Meth. Enzymol. 1990;183:63-98.

Pencea, et al. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 2001 21 (17): 6706-17.

Penichet, et al. An antibody-avidin fusion protein specific for the transferrin receptor serves as a delivery vehicle for effective brain targeting: initial applications in anti-HIV antisense drug delivery to the brain. J Immunol. Oct. 15, 1999;163(8):4421-26.

Pluckthun, A. Antibodies from *Escherichia coli*. In The Pharmacology of Monoclonal Antibodies. vol. 113, Rosenburg and Moore eds. Springer-Verlag, New York. 1994; pp. 269-315.

Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.

Preston, et al, 1997. Evidence for pore-like opening of the blood-brain barrier following forebrain ischemia in rats. Brain Research 761: 4-10.

Ratliff-Schaub, et al. 2005. Randomized controlled trial of transdermal secretion on behavior of children with autism. Autism 9 (3): 256-65.

Reiber, et al. Protein transfer at the blood cerebrospinal fluid barrier and the quantitation of the humoral immune response within the central nervous system. Clin Chim Acta. Mar. 30, 1987;163(3):319-28.

Rempel, et al. A homology model for human α-L-Iduronidase: Insights into human disease. Mol. Genetics and Met. 2005; 85:28-37.

Robinson, et al. The structures of the neurotrophin 4 homodimer and the brain-derived neurotrophic factor / neurotrophin 4 heterodimer reveal a common Trk-binding site. Protein Science 1999 8: 2589-97.

Rochu, et al. Human paraoxonase: a promising approach for pretreatment and therapy of organophosphorus poisoning. Toxicology. Apr. 20, 2007;233(1-3):47-59.

Rossolini, et al. Use of deoxyinosine-containing primers vs degenerate primers for polymerase chain reaction based on ambiguous sequence information. Mol. Cell. Probes. 1994;8(2):91-98.

Rudikoff, et al. Single amino acid substitution altering antigen-binding specificity. Proc Natl Acad Sci U S A. Mar. 1982;79(6):1979-83.

(56) References Cited

OTHER PUBLICATIONS

Ruiz-Leon, et al. Induction of Tyrosine Kinase Receptor B by Retinoic Acid Allows Brain-Derived Neurotrophic Factor-Induced Amyloid Precursor Protein Gene Expression in Human SHSY5Y Neuroblastoma Cells. Neuroscience 120;2003:1019-26.
Sakanaka, et al. In vivo evidence that erythropoietin protects neurons from ischemic damage. Proc Natl Acad Sci U S A. Apr. 14, 1998;95(8):4635-40.
Sakane, et al. Carboxyl-directed Pegylation of Brain-derived Neurotrophic Factor Markedly Reduces Systemic Clearance with Minimal Loss of Biologic Activity. Pharmaceutical Research 1997 14(8):1085-1091.
Sampson et al. Unarmed, tumor-specific monoclonal antibody effectively treats brain tumors. Proc Natl Acad Sci U S A. Jun. 20, 2000;97(13):7503-8.
Sariola, et al. Novel functions and signalling pathways for GDNF. J Cell Sci. Oct. 1, 2003;116(Pt 19):3855-62.
Schabitz, et al. Intraventricular Brain-Derived Neurotrophic Factor Reduces Infarct Size After Focal Cerebral Ischemia in Rats. Journal of Cerebral Blood Flow and Metabolism 1997;17: 500-6.
Schlachetzki, et al. Gene therapy of the brain: the trans-vascular approach. Neurology. Apr. 27, 2004;62(8):1275-81.
Schwartz, et al. A superactive insulin: [B10-aspartic acid]insulin(human). Proc Natl Acad Sci U S A. Sep. 1987;84(18):6408-11.
Scott, et al. Human alpha-L-iduronidase: cDNA isolation and expression. Proc Natl Acad Sci U S A. Nov. 1, 1991;88(21):9695-9.
Sellers, On the theory and computation of evolutionary distances. SIAM Journal on Applied Mathematics. 1974;26:787.
Selmayr, et al. Induction of tumor immunity by autologous B lymphoma cells expressing a genetically engineered idiotype. Gene Ther. May 1999;6(5):778-84.
Shanafelt, et al. Identification of critical amino acid residues in human and mouse granulocyte-macrophage colony-stimulating factor and their involvement in species specificity. J Biol Chem. Jul. 25, 1991;266(21):13804-10.
Shin, et al. Transferrin-antibody fusion proteins are effective in brain targeting, Proceedings of the Natinal Academy of Sciences, 1995. vol. 92, pp. 2820-2824.
Sifuentes, et al. A follow-up study of MPS I patients treated with laronidase enzyme replacement therapy for 6 years. Mol Genet Metab. Feb. 2007;90(2):171-80. Epub Sep. 29, 2006.
Siren, et al., Erythropoetin prevents neuronal apoptosis after cerebral ischemic and metabolic stress. Proc Natl Acad Sci U S A. Mar. 27, 2001;98(7):4044-9.
Skolnick, et al. From genes to protein structure and function: novel applications of computational approaches in the genomic era. Trends Biotechnol. Jan. 2000;18(1):34-9. Review.
Smith, et al. Comparison of Biosequences. Adv. Appl. Math. 1981 1;482-89.
Soukharev, et al. A fluorogenic substrate for detection of organophosphatase activity. Anal Biochem. Apr. 1, 2004;327(1):140-8.
Spina, et al., Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry1992;59 (1):99-106.
Strauss, et al., Brain-derived neurotrophic factor variants are associated with childhood-onset mood disorder: confirmation in a Hungarian sample. Molecular Psychiartry 2005;10: 861-67.
Sukegawa-Hayasaka, et al. Effect of Hunter disease (mucopolysaccharidosis type II) mutations on molecular phenotypes of iduronate-2-sulfatase; enzymatic activity, protein processing and structural analysis. J Inherit Metab Dis 2006;29:755-761.
Takahashi, et al., Inhibition of cell growth and tumorigenesis of human glioblastoma cells by a neutralizing antibody against human basic fibroblast growth factor. Federation of European Biochemical Societies 1991;288 (1,2):65-71.

The BDNF Study Group (Phase III). A controlled trial of recombinant methionyl human BDNF in ALS. Neurology 1999;52: 1427-33.
Thoenen, et al. Neurotrophins: from enthusiastic expectations through sobering experiences to rational therapeutic approaches. Nature Neuroscience Supplement 5;2002:1046-50.
Tomatsu, et al. Murine model (GaIns(tm(C76S)slu)) of MPS IVA with missense mutation at the active site cystein conserved among sulfatase proteins. Mol Genet Metab. Jul. 2007;91(3):261-8.
Tougou, et al. Paraoxonase has a major role in the hydrolysis of prulifloxacin (NM441), a prodrug of a new antibacterial agent. Drug Metab Dispos. Apr. 1998;26(4):355-9.
Tsukahara, et al. The Role of Brain-derived Neurotrophic Factor in Transient Forebrain Ischemia in the Rat Brain. Neurosurgery 34 (2);1994:323-31.
Um, et al. A "classical" homodimeric erythropoietin receptor is essential for the antiapoptotic effects of erythropoietin on differentiated neuroblastoma SH-SY5Y and pheochromocytoma PC-12 cells. Cell Signal. Mar. 2007;19(3):634-45.
Unger, et al. Recombinant α-iduronidase: characterization of the purified enzyme and correction of mucopolysaccharidosis type I fibroblasts. Biochem J. 1994; 384:43-49.
Voznyi, et al. A fluorimeteric enzyme assay for the diagnosis of MPS II (Hunter disease). J Inherit Metab Dis. 2001;24;675-80.
Wang, et al. Identification of the key amino acids of glial cell line-derived neurotrophic factor family receptor alpha1 involved in its biological function. J Biol Chem. Jan. 2, 2004;279(1):109-16.
Ward, E.S. Binding activities of a repertoire of single immunoglobulin variable domains secreted from *Escherichia coli*. Nature. Oct. 12, 1989;341(6242):484-5.
Warrington, et al. Human monoclonal antibodies reactive to oligodendrocytes promote remyelination in a model of multiple sclerosis. Proc Natl Acad Sci U S A. Jun. 6, 2000;97(12):6820-5.
Weich, et al. Interleukin-3/erythropoietin fusion proteins: in vitro effects on hematopoietic cells. Exp Hematol. May 1993;21(5):647-55.
Whetstone, et al. Blood-spinal cord barrier after spinal cord injury: relation to revascularization and wound healing. J Neurosci Res. Oct. 15, 2003;74(2):227-39.
Whittaker, et al. Characterization of the functional insulin binding epitopes of the full-length insulin receptor. J Biol Chem. 2005;280(22):20932-6.
Wiesenhofer, et al. Glial cell line-derived neurotrophic factor (GDNF) and its receptor (GFR-α1) are strongly expressed in human gliomas. Acta Neuropathol. (Berl). 2000;99:131-37.
Wraith, J. Enzyme replacement therapy in mucopolysaccharidosis type I: progress and emerging difficulties. J Inherit Metab Dis. Apr. 2001;24(2):245-50.
Wraith, et al. Mucopolysaccaridosis type II (Hunter syndrome): a clinical review and recommendations for treatment in the era of enzyme replacement therapy. Eur J Pediatr. Mar. 2008;167(3):267-77.
Wu, et al. Drug targeting of a peptide radiopharmaceutical through the primate blood-brain barrier in vivo with a monoclonal antibody to the human insulin receptor. J Clin Invest. Oct. 1, 1997;100(7):1804-12.
Wu, et al. Neuroprotection with noninvasive neurotrophin delivery to the brain. Proc Natl Acad Sci U S A. Jan. 5, 1999;96(1):254-9.
Wu, et al. Neuroprotection in Experimental Stroke with Targeted Neurotrophins. NeuroRX: The Journal of the American Society for Experimental NeuroTherapeutics. 2005;2(1):120-128.
Xue, et al. Intrastriatal administration of erythropoietin protects dopaminergic neurons and improves neurobehavioral outcome in a rat model of Parkinson's disease. Neuroscience. May 25, 2007;146(3):1245-58.
Yamashita, et al. Post-Occlusion Treatment with BDNF Reduces Infarct Size in a Model of Permanent Occlusion of the Middle Cerebral Artery in Rat. Metabolic Brain Disease 12 (4);1997:271-80.
Yan, et al. 1994. Distribution of Intracerebral Ventricularly Administered Neurotrophins in Rat Brain and Its Correlation with Trk Receptor Expression. Experimental Neurology 127: 23-36.

(56) References Cited

OTHER PUBLICATIONS

Yan, et al. 2007 Enduring vulnerability to reinstatement of methamphetamine-seeking behavior in glial-cell-line-derived neurotrophic factor mutant mice. FASEB J. Jul;21(9):1994-2004.
Yip, et al. Three-dimensional structural interactions of insulin and its receptor. J Biol Chem. Jul. 25, 2003;278(30):27329-32.
Zhang, et al. 2001. Conjugation of brain-derived neurotrophic factor to a blood-brain barrier drug targeting system enables neuroprotection in regional brain ischemia following intrvenous injection of the neurotrophin. Brain Research 889: 49-56.
Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-84.
Zhang, et al. 2001. Rapid transferrin efflux from brain to blood across the blood-brain barrier. J Neurochem. Mar;76(5):1597-600.
Albeck, et al. A non-invasive transport system for GDNF across the blood-brain barrier. Regeneration and Transplantation. Jul. 7, 1997; 8(9-10):2293-2298.
Christian, et al. The distribution of D2/D3 receptor binding in the adolescent rhesus monkey using small animal PET imaging. Neuroimage. Feb. 15, 2009;44(4):1334-44. doi: 10.1016/j.neuroimage.2008.10.020. Epub Oct. 29, 2008.
Gehrmann, et al. Biochemical properties of recombinant human beta-glucuronidase synthesized in baby hamster kidney cells. Biochem J. Aug. 1, 1994;301 ( Pt 3):821-8.
Jeffrey, et al. 26-10 Fab-digoxin complex. Affinity and specificity due to surface complementarity. Proc Natl. Acad. Sci USA. 1993; 90(21):10310-10314.
Schuchman, et al. Human alpha-L-iduronidase: Purification and properties of the high uptake (higher molecular weight) and the low uptake (processed) forms. J. Bioi. Chem. 1984; 259(5):3132-3140.
Shipley, et al. The role of glycosylation and phosphorylation in the expression of active human beta-glucuronidase. J Biol Chem. Jun. 5, 1993;268(16):12193-8.
Bosslet, et al. Molecular and functional characterisation of a fusion protein suited for tumour specific prodrug activation. Br J Cancer. Feb. 1992;65(2):234-8.
Bosslet, et al. Tumor-selective prodrug activation by fusion protein-mediated catalysis. Cancer Res. Apr. 15, 1994;54(8):2151-9.
Byrn, et al. Biological properties of a CD4 immunoadhesin. Nature. Apr. 12, 1990;344(6267):667-70.
Chamow, et al. Immunoadhesins: principles and applications. Trends Biotechnol. Feb. 1996;14(2):52-60.
Corchero, et al. The position of the heterologous domain can influence the solubility and proteolysis of beta-galactosidase fusion proteins in *E. coli*. J Biotechnol. Jul. 31, 1996;48(3):191-200.
Kim, et al. N-terminal domains of native multidomain proteins have the potential to assist de novo folding of their downstream domains in vivo by acting as solubility enhancers. Protein Sci. Apr. 2007;16(4):635-43.
Lappi, et al. Expression and activities of a recombinant basic fibroblast growth factor-saporin fusion protein. J Biol Chem. Apr. 29, 1994;269(17):12552-8.
Morita, et al. Association of tumor necrosis factor receptor type II polymorphism 196R with Systemic lupus erythematosus in the Japanese: molecular and functional analysis. Arthritis Rheum. Dec. 2001;44(12):2819-27.

Orcutt, et al. A modular IgG-scFv bispecific antibody topology. Protein Eng Des Sel. Apr. 2010;23(4):221-8. doi: 10.1093/protein/gzp077. Epub Dec. 17, 2009.
Prince, et al. Lipoprotein receptor binding, cellular uptake, and lysosomal delivery of fusions between the receptor-associated protein (RAP) and alpha-L-iduronidase or acid alpha-glucosidase. J Biol Chem. Aug. 13, 2004;279(33):35037-46. Epub May 31, 2004.
Qi, et al. Binding and cytotoxicity of conjugated and recombinant fusion proteins targeted to the gonadotropin-releasing hormone receptor. Cancer Res. Mar. 15, 2004;64(6):2090-5.
Rohrback, et al. Therapeutic antibodies and antibody fusion proteins. Biotechnol Genet Eng Rev. 2003;20:137-63.
Rybak, et al. Humanization of immunotoxins. Proc Natl Acad Sci U S A. Apr. 15, 1992;89(8):3165-9.
Scallon, et al. Functional comparisons of different tumour necrosis factor receptor/IgG fusion proteins. Cytokine. Nov. 1995;7(8):759-70.
Thompson, et al. Improved binding of a bivalent single-chain immunotoxin results in increased efficacy for in vivo T-cell depletion. Protein Eng. Dec. 2001;14(12):1035-41.
Wu, et al. Simultaneous targeting of multiple disease mediators by a dual-variable-domain immunoglobulin. Nat Biotechnol. Nov. 2007;25(11):1290-7. Epub Oct. 14, 2007.
Bickel; et al., "In vivo demonstration of subcellular localization of anti-transferrin receptor monoclonal antibody-colloidal gold conjugate in brain capillary endothelium", Nov. 1994, 42(11), 1493-7.
Boado, et al. Glycemic control and chronic dosing of rhesus monkeys with a fusion protein of iduronidase and a monoclonal antibody against the human insulin receptor. Drug Metab Dispos. Oct. 2012;40(10):2021-5. doi: 10.1124/dmd.112.046375. Epub Jul. 20, 2012.
Jones, et al. Determination of Tumor Necrosis Factor Binding Protein Disulfide Structure: Deviation of the Fourth Domain Structure from the TNFR/NGFR Family Cysteine-Rich Region Signature Biochemistry. 1997; 36: 14914-23.
Pardridge, Biopharmaceutical drug targeting to the brain. Journal of Drug Targeting, 18(3): 157-167 (2010).
Peppel; et al., "A tumor necrosis factor (TNF) receptor-IgG heavy chain chimeric protein as a bivalent antagonist of TNF activity.", Dec. 1, 1991, 174(6), 1483-9.
Sumbria; et al., "Brain protection from stroke with intravenous TNFa decoy receptor-Trojan horse fusion protein", Oct. 2012, 32(10), 1933-8.
Traunecker; et al., "Highly efficient neutralization of HIV with recombinant CD4-immunoglobulin molecules.", May 4, 1989, 339(6219), 68-70.
Zhou; et al., "Neuroprotection with a brain-penetrating biologic tumor necrosis factor inhibitor.", Nov. 2011, 339(2), 618-23.
Boado, Ruben J. et al. Glycemic Control and Chronic Dosing of Rhesus Monkeys with a Fusion Protein of Iduroniadase and a Monoclonal Antibody Against the Human Insulin Receptor Drug Metabolism and Disposition vol. 40, No. pp. 2021-2025 (2012).
Zhou, et all. Brain-penetrating IgG-iduronate 2-sulfatase fusion protein for the mouse. Drug Metab. Dispos. Feb. 2012;40(2):329-35. doi: 10.1124/dmd.111.042903. Epub Nov. 7, 2011.

\* cited by examiner

COMPOSITIONS AND METHODS FOR BLOOD-BRAIN BARRIER DELIVERY OF IGG-DECOY RECEPTOR FUSION PROTEINS

CROSS-REFERENCE

This application is a national stage application of International Application No. PCT/US2010/027882, filed Mar. 18, 2010, which claims the benefit of U.S. Provisional Patent Application No. 61/161,320, filed Mar. 18, 2009, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Oct. 25, 2012, is named 28570831.txt and is 33,754 bytes in size.

BACKGROUND OF THE INVENTION

The soluble extracellular domain (ECD) of a target receptor, such as the tumor necrosis factor receptor (TNFR), has therapeutic actions in human diseases. The receptor ECD acts as an exogenous decoy receptor, which sequesters the endogenous ligand, e.g. tumor necrosis factor (TNF)-α, and thereby blocks access of the endogenous ligand to the endogenous target receptor. Decoy receptors could be powerful new treatments of brain diseases. However, decoy receptors, like other large molecule drugs, do not cross the blood-brain barrier (BBB). Thus, to date, it has not been possible to treat patients with brain disorders by systemic administration of recombinant decoy receptors.

SUMMARY OF THE INVENTION

Described herein are compositions and related methods for delivering IgG-receptor ECD ("decoy receptor") fusion proteins across the BBB to the CNS in a subject in need thereof. In particular, the methods allow delivery of a decoy receptor to the CNS by systemically administering a therapeutically effective amount of a bifunctional decoy receptor fusion antibody that comprises a receptor ECD and an antibody that binds to the extracellular domain of a receptor expressed on the surface of BBB.

Accordingly, in one aspect provided herein is a bifunctional decoy receptor fusion antibody comprising the amino acid sequence of a heavy chain immunoglobulin or a light chain immunoglobulin covalently linked to the amino acid sequence of a receptor extracellular domain, wherein the fusion antibody binds to a receptor expressed on the BBB and a ligand for the receptor extracellular domain. In some embodiments, the receptor expressed on the BBB is an insulin receptor, a transferrin receptor, or a lipoprotein receptor. In some embodiments, the receptor expressed on the BBB is a human insulin receptor. In some embodiments, the bifunctional decoy receptor fusion antibody competes for binding to the human insulin receptor with a bifunctional decoy receptor fusion antibody comprising the amino acid sequences of SEQ ID NOs 4 and 6, or SEQ ID NOs: 6 and 7. In some embodiments, the receptor extracellular domain is from a cytokine receptor, a TNF-α receptor, a TNF-related apoptosis inducing ligand (TRAIL) receptor, a TNF-like weak inducer of apoptosis (TWEAK) receptor, an IL-6 receptor, a vascular endothelial growth factor receptor, or an ephrin receptor. In some embodiments, the receptor extracellular domain comprises a TNF-α receptor extracellular domain. In some cases, the TNF-α receptor extracellular domain comprises an amino acid sequence at least 85% (e.g., 90%, 95%, or 100%) identical to that of a human, mouse, rat, or pig TNF-α receptor extracellular domain. In certain embodiments, the amino acid sequence of the TNF-α receptor extracellular domain is fused to the carboxy terminus of the heavy chain immunoglobulin or the light chain immunoglobulin. In certain embodiments, the amino acid sequence of the TNF-α receptor extracellular domain is fused to the carboxy terminus of the heavy chain immunoglobulin.

In a related aspect provided herein is a bifunctional decoy receptor fusion antibody (e.g., HIRMAb-TNFR fusion protein) that has a brain uptake that is more than 1%. 2%. 3%. 5%, 7% or 10% ID/100 gram protein. In some embodiments, the bifunctional decoy receptor fusion antibody (e.g., HIRMAb-TNFR fusion protein) exhibits a brain uptake that is more than 1-, 2-. 5-, 10-, 13-, 15-, 17-, 20-, 25-, 30-, 35-, 40-, 45-, or 50-fold greater than the brain uptake of a fusion protein of a decoy receptor and the Fc fragment of human IgG, e.g., TNFR:Fc. In some embodiments, a bifunctional decoy receptor fusion antibody described herein (e.g., HIRMAb-TNFR fusion protein) is selectively enriched in the brain when compared to other organs. In some embodiments, when the ratio of the organ PS product for a decoy receptor-BBB receptor AB fusion antibody described herein (e.g., HIRMAb-TNFR fusion protein) relative to the organ PS product for the TNFR:Fc fusion protein is determined for multiple organs, the brain ratio is more than 1-, 2-. 5-, 10-, 13-, 15-, 17-, 20-, 25-, 30-, 35-, 40-, 45-, or 50-fold greater than the fat, muscle, heart, lung, liver, and/or spleen ratio.

In a related aspect provided herein is a nucleic acid comprising: (i) a first sequence encoding a heavy chain immunoglobulin and a receptor extracellular domain in frame with the heavy chain immunoglobulin; (ii) a second sequence encoding a light chain immunoglobulin and a receptor extracellular domain in frame with the light chain immunoglobulin; or (iii) the complementary sequence of (i) or (ii); wherein the heavy chain and light chain immunoglobulin are from an antibody against a BBB receptor. In some embodiments, the encoded receptor extracellular domain is from a TNF-α receptor, a TNF-related apoptosis inducing ligand (TRAIL) receptor, a TNF-like weak inducer of apoptosis (TWEAK) receptor, an IL-6 receptor, a vascular endothelial growth factor receptor, or an ephrin receptor. In some embodiments, the encoded receptor extracellular domain is from a TNF-α receptor (e.g., a human TNF-α receptor). In other embodiments, the encoded extracellular domain from a TNF-α receptor comprises an amino acid sequence at least 85% identical to that of a human, mouse, rat, or pig TNF-α receptor extracellular domain. In some embodiments, the encoded immunoglobulin heavy chain or light chain is from an antibody against the human insulin receptor, transferrin receptor, or lipoprotein receptor. In certain embodiments, the above-mentioned first sequence encodes an amino acid sequence at least 85% (e.g., 90%, 95%, or 100%) identical to the amino acid sequence corresponding to SEQ ID NOs:4 or 7; or the above-mentioned second sequence encodes an amino acid sequence at least 85% (e.g., 90%, 95%, or 100%) identical to the amino acid sequence corresponding to SEQ ID NO:6. In other embodiments, the nucleic acid hybridizes, under high stringency conditions, to a nucleic acid encoding SEQ ID NOs 4, 6, or 7 (e.g., a nucleic acid comprising the nucleotide sequence of SEQ ID NOs 3 or 5). In some embodiments, the encoded extracellular domain from a TNF-α receptor is covalently linked to the carboxy terminus of the heavy chain immunoglobulin or the light chain immunoglobulin. In some embodiments, the encoded extracellular domain from a TNF-α receptor is covalently linked to the carboxy terminus of the heavy chain immunoglobulin.

In some embodiments, the nucleic acid is provided as a nucleic acid vector. In some embodiments, the nucleic acid vector comprises: (i) a first sequence encoding a heavy chain immunoglobulin and a receptor extracellular domain in frame with the heavy chain immunoglobulin; (ii) a second sequence encoding a light chain immunoglobulin and a receptor extracellular domain in frame with the light chain immunoglobulin; or (iii) the complementary sequence of (i) or (ii); wherein the heavy chain and light chain immunoglobulin are from an antibody against a BBB receptor. In some embodiments, the nucleic acid vector comprises (i) and further comprises a nucleic acid sequence encoding a light chain immunoglobulin from an antibody against the BBB receptor; or the nucleic acid comprises (ii) and further comprises a nucleic acid encoding a heavy chain immunoglobulin from an antibody against the BBB receptor. In a related aspect provided herein is a cell (e.g., a mammalian cell) comprising any of the above-mentioned nucleic acids.

In a further aspect provided herein is a method for delivering a decoy receptor across the blood brain barrier, comprising systemically administering to a subject a pharmaceutical composition comprising a bifunctional decoy receptor fusion antibody comprising the amino acid sequence of a heavy chain immunoglobulin or a light chain immunoglobulin covalently linked to the amino acid sequence of a receptor extracellular domain, wherein the fusion antibody binds to a receptor expressed on the BBB and the ligand for the receptor extracellular domain. In some embodiments, the receptor expressed on the BBB is an insulin receptor, a transferrin receptor, an insulin-like growth factor (IGF) receptor, a leptin receptor, or a lipoprotein receptor. In some embodiments, the receptor extracellular domain is from a TNF-α receptor, a TNF-related apoptosis inducing ligand (TRAIL) receptor, a TNF-like weak inducer of apoptosis (TWEAK) receptor, an IL-6 receptor, a vascular endothelial growth factor receptor, or an ephrin receptor. In some embodiments, the extracellular domain from a TNF-α receptor is covalently linked to the carboxy terminus of the heavy chain immunoglobulin or the light chain immunoglobulin. In some embodiments, the extracellular domain from a TNF-α receptor is covalently linked to the carboxy terminus of the heavy chain immunoglobulin.

In another aspect provided herein is a method for treating a CNS condition, comprising systemically administering to a subject in need thereof a therapeutically effective amount of a pharmaceutical composition comprising a bifunctional decoy receptor fusion antibody comprising the amino acid sequence of a heavy chain immunoglobulin or a light chain immunoglobulin covalently linked to the amino acid sequence of a receptor extracellular domain, wherein the fusion antibody binds to a receptor expressed on the BBB and the ligand for the receptor extracellular domain. In some embodiments, the receptor expressed on the BBB is an insulin receptor, a transferrin receptor, an insulin-like growth factor (IGF) receptor, a leptin receptor, or a lipoprotein receptor. In some embodiments, the receptor extracellular domain is from a TNF-α receptor, a TNF-related apoptosis inducing ligand (TRAIL) receptor, a TNF-like weak inducer of apoptosis (TWEAK) receptor, an IL-6 receptor, a vascular endothelial growth factor receptor, or an ephrin receptor. In some embodiments, the CNS condition to be treated is an acute CNS condition, e.g., global brain ischemia, local brain ischemia, traumatic brain injury, or spinal cord injury. In other embodiments, the CNS condition to be treated is a chronic CNS condition, e.g., a neurodegenerative condition such as Alzheimer's disease, Parkinson's disease, amyotrophic lateral sclerosis, Huntington's disease, multiple sclerosis, transverse myelitis, motor neuron disease, Pick's disease, tuberous sclerosis, Canavan's disease, Rett's syndrome, spinocerebellar ataxias, Friedreich's ataxia, optic atrophy, or retinal degeneration.

In yet another aspect provided herein is a method for manufacturing a bifunctional decoy receptor fusion antibody, comprising stably integrating into a eukaryotic cell a single tandem expression vector encoding:

(i) both an immunoglobulin heavy chain fused to a receptor extracellular domain, and an immunoglobulin light chain; or (ii), both an immunoglobulin light chain fused to a receptor extracellular domain, and an immunoglobulin heavy chain, wherein the encoded immunoglobulin heavy chain and immunoglobulin light chain are from an antibody against a receptor expressed on the BBB. In some embodiments, the receptor expressed on the BBB is an insulin receptor, a transferrin receptor, an insulin-like growth factor (IGF) receptor, a leptin receptor, or a lipoprotein receptor. In some embodiments, the encoded receptor extracellular domain is from a TNF-α receptor, a TNF-related apoptosis inducing ligand (TRAIL) receptor, a TNF-like weak inducer of apoptosis (TWEAK) receptor, an IL-6 receptor, a vascular endothelial growth factor receptor, or an ephrin receptor. In some embodiments, the extracellular domain from a TNF-α receptor is covalently linked to the carboxy terminus of the immunoglobulin heavy chain or the immunoglobulin light chain. In some embodiments, the encoded extracellular domain from a TNF-α receptor is covalently linked to the carboxy terminus of the immunoglobulin heavy chain.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, as follows:

DETAILED DESCRIPTION OF THE INVENTION

Figure 1:
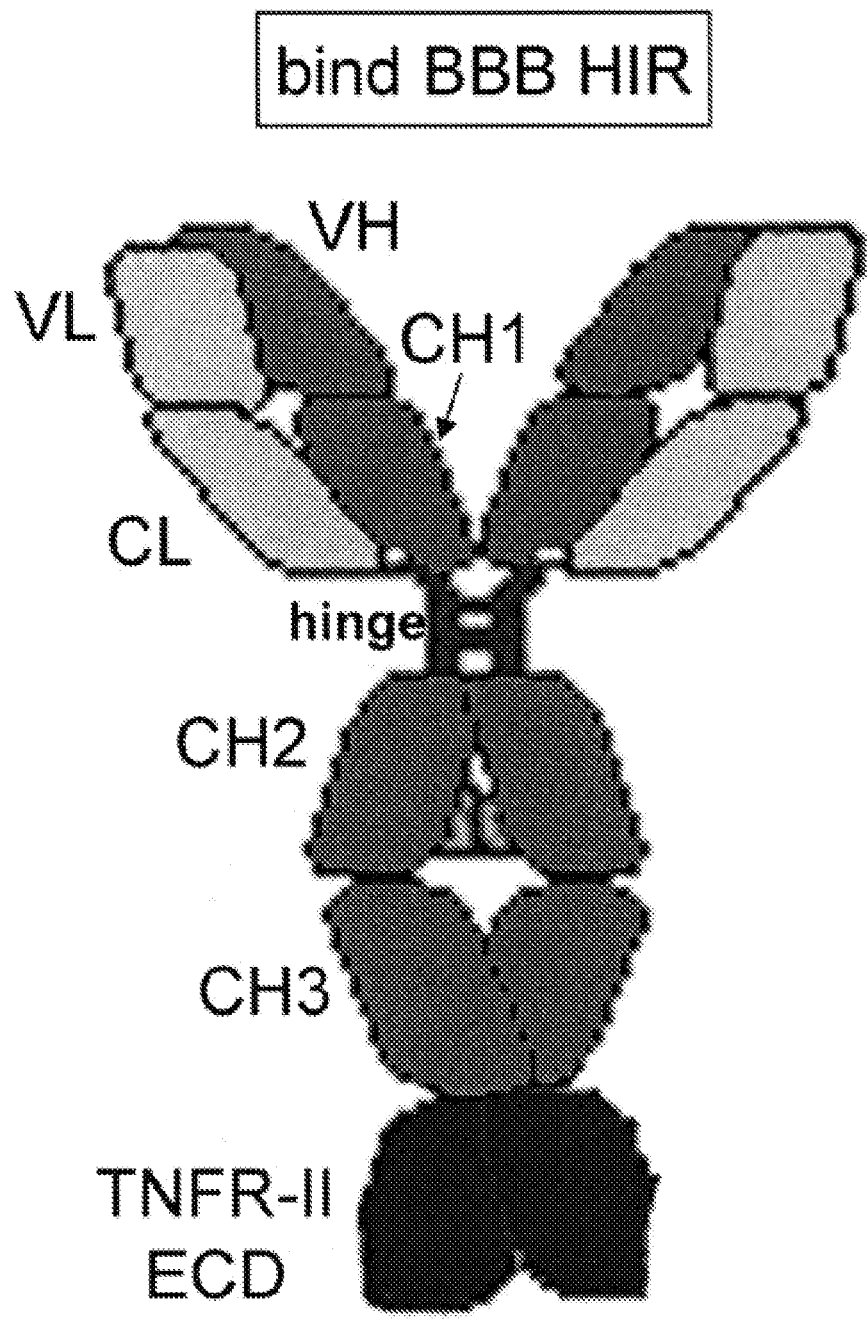
FIG. 1. The HIRMAb-TNFR fusion protein is formed by fusion of the amino terminus of the TNFR ECD to the carboxyl terminus of the CH3 region of the heavy chain of the chimeric HIRMAb. The fusion protein is a bi-functional molecule: the fusion protein binds the HIR, at the BBB, to mediate transport into the brain, and binds TNFα, to suppress the inflammatory properties of this cytokine.

I. Introduction
II. Some Definitions
III. The blood brain barrier
IV. Decoy Receptor Fusion Antibodies for transport across the BBB
V. Compositions
VI. Nucleic acids, vectors, cells, and manufacture
VII. Methods
VIII. Examples
IX. Sequences

ABBREVIATIONS

AA amino acid
BBB blood-brain barrier
BCA bicinchoninic acid
BGH bovine growth hormone CDR complementarity determining region
CHO Chinese hamster ovary
CMV cytomegalovirus
DC dilutional cloning
DHFR dihydrofolate reductase
ECD extracellular domain
ED50 effective dose causing 50% saturation
FR framework region
FS flanking sequence
FWD forward
HC heavy chain
HIR human insulin receptor
HIRMAb MAb to HIR
HIRMAb HC heavy chain of HIRMAb
HIRMAb LC light chain of HIRMAb
HIRMAb-TNFR fusion protein of HIRMAb and TNFR ECD, where the TNFR is fused to the HC carboxyl terminus
HT hypoxanthine-thymidine
IgG immunoglobulin G
IGF insulin-like growth factor
LC light chain
MAb monoclonal antibody
MAH mouse anti-human IgG
MTX methotrexate
MW molecular weight
N asparagine
nt nucleotide
ODN oligodeoxynucleotide
orf open reading frame
pA poly-adenylation
PAGE polyacrylamide gel electrophoresis
PBS phosphate buffered saline
PBST PBS plus Tween-20
PCR polymerase chain reaction
pI isoelectric point
R receptor
REV reverse
RNase A ribonuclease A
RT reverse transcriptase
RT room temperature
SDM site-directed mutagenesis
SDS sodium dodecyl sulfate
SEC size exclusion chromatography
Ser serine
SFM serum free medium
TH Trojan horse
TNF tumor necrosis factor
TNFR TNF receptor
TV tandem vector
UTV universal TV
VH variable region of heavy chain
VL variable region of light chain

I. INTRODUCTION

Genetically engineered decoy receptors are powerful new therapeutics, particularly when the receptor ECD is fused to the amino terminus of the Fc fragment of a human immunoglobulin G, such as IgG1. The Fc fragment is a dimeric protein of two constant region chains. As most receptors form dimers within the membrane, fusion of a receptor ECD to an Fc fragment permits the native dimeric configuration of the receptor protein. One well described example of a decoy receptor is the TNFα decoy receptor-Fc fusion protein. The TNFα decoy receptor-Fc fusion protein is a powerful biologic therapeutic for peripheral inflammatory conditions due to its ability to sequester the pro-inflammatory cytokine, TNFα, which thereby inhibits activation of the endogenous TNFR by its endogenous ligand. However, the TNFR:Fc fusion protein cannot be prescribed for CNS conditions.

The blood brain barrier is a severe impediment to the delivery of systemically administered soluble decoy receptors to the central nervous system, where they act to neutralize certain ligands (e.g., TNF-α) that play a role in some neuropathologies, e.g., neuroinflammation. The compositions and methods described herein address three factors that are important in delivering decoy receptors across the BBB to the CNS: 1) modification of a receptor extracellular domain (ECD), referred to herein as a "decoy receptor," to allow it to cross the BBB; 2) the amount and rate of uptake of systemically administered modified IgG-receptor fusion antibodies into the CNS, and 3) retention of decoy receptor activity once across the BBB. Various aspects of the methods and compositions described herein address these factors, by providing fusion antibodies, that can be administered systemically, comprising a decoy receptor fused, with or without an intervening linker sequence, to an immunoglobulin (heavy chain or light chain) directed against the extracellular domain of a receptor (e.g., a human insulin receptor) expressed on the BBB.

Accordingly, the invention provides compositions and methods for delivering a decoy receptor (e.g., a soluble TNF-α receptor ECD) to the central nervous system of a subject in need, e.g., a subject suffering from or at high risk of CNS inflammation, by systemically administering to a subject in need thereof a therapeutically effective dose of a bifunctional decoy receptor fusion antibody comprising an antibody against a receptor expressed on the BBB (e.g., an hIR) and a receptor ECD (e.g., human TNF-α receptor ECD).

II. SOME DEFINITIONS

The term "antibody" describes an immunoglobulin whether natural or partly or wholly synthetically produced. The term also covers any polypeptide or protein having a binding domain which is, or is homologous to, an antigen-binding domain. CDR grafted antibodies are also contemplated by this term.

"Native antibodies" and "native immunoglobulins" are usually heterotetrameric glycoproteins of about 150,000 daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH") followed by a number of constant domains ("CH"). Each light chain has a variable domain at one end ("VL") and a constant domain ("CL") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable domain" refers to protein domains that differ extensively in sequence among family members (i.e. among different isoforms, or in different species). With respect to antibodies, the term "variable domain" refers to the variable domains of antibodies that are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the "framework region" or "FR". The variable domains of unmodified heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., (1991), Sequences of Proteins of Immunological Interest, 5th Ed. Public Health Service, National Institutes of Health, Bethesda, Md., pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from three "complementarity determining regions" or "CDRs", which directly bind, in a complementary manner, to an antigen and are known as CDR1, CDR2, and CDR3 respectively. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3); Kabat et al., (1991), Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, (1987), *J. Mol. Biol.*, 196:901-917.

As used herein, "variable framework region" or "VFR" refers to framework residues that form a part of the antigen binding pocket or groove and/or that may contact antigen. In some embodiments, the framework residues form a loop that is a part of the antigen binding pocket or groove. The amino acids residues in the loop may or may not contact the antigen. In an embodiment, the loop amino acids of a VFR are determined by inspection of the three-dimensional structure of an antibody, antibody heavy chain, or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g. structural positions) can be less diversified. The three dimensional structure of the antibody variable domain can be derived from a crystal structure or protein modeling. In some embodiments, the VFR comprises, consists essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3.

The VFR can form a loop that is well positioned to make contact with a target antigen or form a part of the antigen binding pocket.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

In referring to an antibody or fusion antibody described herein, the terms "selectively bind," "selectively binding," "specifically binds," or "specifically binding" refer to binding to the antibody or fusion antibody to its target antigen for which the dissociation constant (Kd) is about $10^{-6}$ M or lower, i.e., $10^{-7}$, $10^{-8}$, $10^{-9}$, $10^{-10}$, $10^{-11}$, or $10^{-12}$M.

The term antibody as used herein will also be understood to mean one or more fragments of an antibody that retain the ability to specifically bind to an antigen, (see generally, Holliger et al., (2005), *Nature Biotech.*, 23(9):1126-1129). Non-limiting examples of such antibodies include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature*, 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) *Science*, 242:423 426; and Huston et al., (1988) *Proc. Natl. Acad. Sci. USA*, 85:5879 5883; and Osbourn et al., (1998), *Nat. Biotechnol.*, 16:778). Such single chain antibodies are also intended to be encompassed within the term antibody. Any VH and VL sequences of specific scFv can be linked to human immunoglobulin constant region cDNA or genomic sequences, in order to generate expression vectors encoding complete IgG molecules or other isotypes. VH and VL can also be used in the generation of Fab, Fv or other fragments of immunoglobulins using either protein chemistry or recombinant DNA technology. Other forms of single chain antibodies, such as diabodies are also encompassed.

"F(ab')2" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CHγ1 (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise a VH, a VL, or both a VH and VL domain of an antibody, wherein both domains are present in a single polypeptide chain. In some embodiments, the Fv polypeptide further comprises a polypeptide linker between the VH and VL domains which enables the sFv to form the desired structure for antigen binding. For a review of sFv see, e.g., Pluckthun in *The Pharmacology of Monoclonal Antibodies, Vol.* 113, Rosenburg and Moore eds. Springer-Verlag, New York, pp. 269 315 (1994).

A "chimeric" antibody includes an antibody derived from a combination of different mammalian sources. The mammal may be, for example, a rabbit, a mouse, a rat, a goat, or a human. The combination of different mammals includes combinations of fragments from human and mouse sources.

In some embodiments, an antibody of the present invention is a monoclonal antibody (MAb), typically a chimeric human-mouse antibody derived by humanization of a mouse monoclonal antibody. Such antibodies are obtained from, e.g., transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesis human antibodies specific for human antigens, and the mice can be used to produce human antibody-secreting hybridomas.

"Treatment" or "treating" as used herein includes achieving a therapeutic benefit and/or a prophylactic benefit. By therapeutic benefit is meant eradication or amelioration of the underlying disorder or condition being treated. A prophylactic benefit of treatment includes reducing the risk of a condition, retarding the progress of, or decreasing the likelihood of occurrence of a condition. As used herein, "treating" or "treatment" includes prophylaxis.

As used herein, the term "effective amount" can be an amount, which when administered systemically, is sufficient to effect beneficial or desired results in the CNS. An effective amount is also an amount that produces a prophylactic effect, e.g., an amount that delays, reduces, or eliminates the appearance of an acute pathological or undesired condition. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention will be determined by a patient's attending physician or veterinarian. Such amounts are readily ascertained by one of ordinary skill in the art and will a therapeutic effect when administered in accordance with the present invention.

The term "molecular trojan horse," as used herein, refers to a molecule that is transported across the BBB, and is capable of acting as a ferry for trans-BBB transport into the CNS when linked covalently or non-covalently to another molecule that does not cross the BBB on its own. Examples of a molecular trojan horse include, but are not limited to, polypeptides (e.g., antibodies) that bind to the ECD of receptors expressed on the BBB, e.g., insulin receptors, transferrin receptors, IGF receptors, lipoprotein receptors, or leptin receptors.

A "subject" or an "individual," as used herein, is an animal, for example, a mammal. In some embodiments a "subject" or an "individual" is a human. In some non-limiting embodiments, the subject suffers from a chronic or acute CNS condition.

In some embodiments, a pharmacological composition comprising a decoy receptor ECD-BBB receptor Ab fusion antibody is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, intra-arterial, subcutaneous, intramuscular, intraperitoneal, transdermal, by inhalation, transbuccal, intranasal, rectal, oral, parenteral, sublingual, or trans-nasal.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in *Remington's Pharmaceutical Sciences*, Gennaro, A R, ed., 20th edition, 2000: Williams and Wilkins Pa., USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine Amino acid analogs refers to compounds that have the same basic chemical structure as a naturally occurring amino acid, i.e., an carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al.,
(1991), *Nucleic Acid Res.*, 19:5081; Ohtsuka et al., (1985), *J. Biol. Chem.*, 260:2605-2608; and Rossolini et al., (1994), *Mol. Cell. Probes* 8:91-98).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc.) in a sample. In another example, a polypeptide is purified if it is substantially removed from or concentrated in its natural environment. Methods for purification and isolation of nucleic acids and proteins are well known in the art.

The term "BBB receptor Ab," refers to an antibody against the extracellular domain of a receptor expressed on the blood-brain barrier. Non-limiting examples of BBB receptors include insulin receptor (e.g. human insulin receptor), transferrin receptor, lipoprotein receptor, and leptin receptor.

III. THE BLOOD BRAIN BARRIER

The BBB is formed by tight junctions that cement together the endothelial cells that form the capillaries of the brain and spinal cord (Pardridge, 2008, *Bioconj Chem*, 19: 1327-1338). There are 400 miles of brain capillaries in the human brain. The electrical resistance across the brain capillary endothelial plasma membrane, which forms the BBB in vivo, is as high as in any biological membrane. The usual para-cellular and trans-cellular pathways for free solute exchange between the blood and an organ are absent in the CNS. Consequently, a drug in blood can access brain only via 1 of 2 mechanisms: (i) free diffusion owing to high lipid solubility of small molecules, and (ii) transport via an endogenous BBB transporter. One approach to solving the BBB drug delivery problem for decoy receptor compositions is to re-engineer the decoy receptor so that it can access certain endogenous transport systems within the BBB. The methods described herein permit a functional decoy receptor to cross the BBB from the peripheral blood into the CNS following systemic administration of a decoy receptor fusion antibody composition described herein. The methods described herein exploit the expression receptors expressed on the surface of the BBB (e.g., human insulin receptors) to shuttle the desired bifunctional receptor ECD-BBB receptor fusion antibody from peripheral blood into the CNS.

IV. DECOY RECEPTOR FUSION ANTIBODIES FOR TRANSPORT ACROSS THE BBB

In one aspect, the invention provides compositions and methods that utilize a bifunctional decoy receptor fusion antibody that contains the amino acid sequence of a receptor ECD (e.g., a human TNF-α receptor ECD) covalently linked to the amino acid sequence of a heavy chain immunoglobulin or a light chain immunoglobulin. Such bifunctional decoy receptor fusion antibodies can bind to a receptor expressed on the BBB and a ligand for the receptor ECD. The compositions and methods are useful in transporting a decoy receptor from the peripheral blood and across the BBB into the CNS.

The BBB has been shown to have specific receptors that allow the transport from the blood to the brain of several macromolecules; these transporters are suitable as transporters for compositions of the invention. Endogenous BBB receptor-mediated transport systems useful in the invention include, but are not limited to, those that transport insulin, transferrin, insulin-like growth factors 1 and 2 (IGF1 and IGF2), leptin, and lipoproteins. In some embodiments, the invention utilizes an antibody that is capable of crossing the BBB via the endogenous insulin BBB receptor-mediated transport system, e.g., the human endogenous insulin BBB receptor-mediated transport system. In some embodiments, the bifunctional decoy receptor fusion antibody comprises an HIR antibody. The decoy receptor-HIRAb fusion antibodies described herein bind to the ECD of the human insulin receptor. In some embodiments, the decoy receptor ECD is fused to the carboxy terminus of the heavy chain immunoglobulin (e.g, a HIRAb heavy chain immunoglobulin). In other embodiments, the decoy receptor ECD is fused to the C-terminus of the light chain immunoglobulin (e.g., a HIRAb light chain immunoglobulin). In some cases, the above-mentioned receptor ECD contains an amino acid sequence at least 80% (e.g., 85%, 90%, 95%, 97%, 99%, or another percent identical from at least 80% to 100% identical to an ECD from a human, mouse, rat, or pig cytokine receptor, TNF-α receptor, TNF-related apoptosis inducing ligand (TRAIL) receptor, TNF-like weak inducer of apoptosis (TWEAK) receptor, IL-6 receptor, vascular endothelial growth factor receptor, or ephrin receptor. In some embodiments, the above-mentioned receptor ECD is from a cytokine receptor. In some embodiments, the receptor ECD contains a TNF-α receptor domain (e.g., a human TNF-α receptor ECD). GenBank accession numbers for the amino acid sequences of the above-mentioned receptors are provided in table 1 below.

antibodies to the human BBB insulin receptor with sufficient human sequences for use in the invention are described in, e.g., Boado et al., (2007), *Biotechnol Bioeng*, 96(2):381-391. A more highly humanized form of the HIRMAb can also be engineered, and the humanized HIR Ab has activity comparable to the murine HIR Ab and can be used in embodiments of the invention. See, e.g., U.S. Patent Application Publication Nos. 20040101904, filed Nov. 27, 2002 and 20050142141, filed Feb. 17, 2005.

In exemplary embodiments, bifunctional decoy receptor fusion antibodies compete for binding to the human insulin receptor with a bifunctional decoy receptor fusion antibody containing the amino acid sequences of SEQ ID NOs 4 and 6, or SEQ ID NOs: 6 and 7. In some cases, the competing bifunctional decoy receptor has an affinity for the human insulin receptor that is at least about 20%, e.g., 25%, 30%, 35%, 40%, 45%, 50%, 60%, 65%, 70%, 75%, 80%, 85%, 90%, or another percent from at least about 20% to 100% identical to a functional decoy receptor fusion antibody containing the amino acid sequences of SEQ ID NOs 4 and 6, or SEQ ID NOs: 6 and 7. In other embodiments, the bifunctional decoy receptor fusion antibody contains amino acid sequences that are least about 80%, 85%, 90%, 95%, or some other percent identical from at least about 80% to about 100% identical to SEQ ID NOs 4 and 6, or SEQ ID NOs 6 and 7.

BBB receptor antibodies used in the invention may be glycosylated or non-glycosylated. If the antibody is glycosylated, any pattern of glycosylation that does not signifi-

TABLE 1

GenBank Accession Numbers for Receptors from Various Species

| Receptor | Human | Mouse | Rat | Pig |
|---|---|---|---|---|
| TNF-α | NP_001056 | AY541589.1 | AAK53563 | NP_999134 |
| TRAIL | NP_003835 | NP_064671 | ACL51000.1 | XP_001926758.1 |
| TWEAK | NP_057723.1 | NP_038777.1 | NP_851600.1 | NP_001136311.1 |
| IL-6 | NP_000556.1 | NP_034689.2 | NP_058716.2 | NP_999568.1 |
| VEGF | NP_002010.2 | NP_034358.2 | NP_062179.1 | XP_001925775.1 |
| Ephrin | NP_005223.4 | NP_076069.2 | NP_001101328.1 | NP_001128439.1 |

Insulin receptors and their extracellular, insulin binding domain (ECD) have been extensively characterized in the art both structurally and functionally. See, e.g., Yip et al., (2003), *J. Biol. Chem.*, 278(30):27329-27332; and Whittaker et al., (2005), *J. Biol. Chem.*, 280(22):20932-20936. The amino acid and nucleotide sequences of the human insulin receptor can be found under GenBank accession No. NM_000208.

Insulin receptors expressed on the BBB can thereby serve as a vector for transport of a decoy receptor, e.g., a TNF-α receptor ECD, across the BBB. Certain insulin receptor ECD-specific antibodies may mimic the endogenous ligand and thereby traverse a plasma membrane barrier via transport on the specific receptor system. In certain embodiments, a receptor decoy-HIRAb fusion antibody binds an exofacial epitope on the human BBB HIR and this binding enables the fusion antibody to traverse the BBB via a transport reaction that is mediated by the human BBB insulin receptor.

For use in humans, a chimeric HIR Ab is preferred that contains enough human sequence that it is not significantly immunogenic when administered to humans, e.g., about 80% human and about 20% mouse, or about 85% human and about 15% mouse, or about 90% human and about 10% mouse, or about 95% human and 5% mouse, or greater than about 95% human and less than about 5% mouse Chimeric cantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

One of ordinary skill in the art will appreciate that current technologies permit a vast number of sequence variants of BBB receptor Abs or decoy receptor ECDs to be readily generated (e.g., in vitro) and screened for binding to a target antigen such as the ECD of the human insulin receptor or for binding to a ligand of the decoy receptor ECD. See, e.g., Fukuda et al., (2006), *Nuc. Acid Res.*, 34(19) (published online) for an example of μltra high throughput screening of antibody sequence variants. See also, Chen et al., (1999), *Prot Eng*, 12(4): 349-356. In order to isolate sequence variants, random mutagenesis of the entire sequence or specific subsequences corresponding to particular domains may be performed. Alternatively, site directed mutagenesis can be performed reiteratively while avoiding mutations to residues known to be critical to BBB receptor or decoy receptor ligand binding. For example, the structure function of the TNF-α receptor is known in the art as described in, e.g., Mukai et al (2009), *J Mol Biol,* 385(4):1221-1229. Further, in generating multiple variants of a decoy receptor ECD sequence such as that of the human TNF-α receptor, mutation tolerance prediction programs can be used to greatly reduce the number of non-functional sequence variants that would be generated by strictly random mutagenesis. Various programs for predicting the effects of amino acid substitutions in a protein sequence on protein function (e.g., SIFT, PolyPhen, PANTHER PSEC, PMUT, and TopoSNP) are described in, e.g., Henikoff et al., (2006), *Annu. Rev. Genomics Hum. Genet.,* 7:61-80. Accordingly, one of ordinary skill in the art will appreciate that a very large number of operable decoy receptor ECD sequence variants can be obtained by generating and screening extremely diverse "libraries" of decoy receptor (e.g., human TNF-α receptor ECD sequences) sequence variants by methods that are routine in the art, as described above.

Percent sequence identity is determined by conventional methods. See, for example, Altschul et al., (1986), *Bull. Math. Bio.,* 48:603, and Henikoff and Henikoff, (1992), *Proc. Natl. Acad. Sci. USA,* 89:10915. Briefly, two amino acid sequences are aligned to optimize the alignment scores using a gap opening penalty of 10, a gap extension penalty of 1, and the "BLOSUM62" scoring matrix of Henikoff and Henikoff (supra). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson et al., (1988), *Proc. Nat'l Acad. Sci. USA,* 85:2444, and by Pearson (1990), *Meth. Enzymol.* 183:63. Briefly, FASTA first characterizes sequence similarity by identifying regions shared by the query sequence (e.g., SEQ ID NO:4 or SEQ ID NO: 6) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman et al., (1970), *J. Mol. Biol.* 48:444; Sellers (1974), *SIAM J. Appl. Math.,* 26:787, which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, (1990), *Meth. Enzymol.,* 183:63.

The present invention also includes proteins having a conservative amino acid change, compared with an amino acid sequence disclosed herein. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al., (1992), *Proc. Nat'l Acad. Sci., USA,* 89:10915. Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the invention.

V. COMPOSITIONS

Strikingly, it has been found that the bifunctional decoy receptor fusion antibodies described herein retain a high proportion of the activity of their separate constituent proteins, i.e., binding of the BBB receptor Ab to the BBB receptor, e.g., the human insulin receptor ECD, and binding of the decoy receptor ECD (e.g., a TNF-α receptor to a cognate ligand).

Described herein are bifunctional decoy receptor-BBB receptor fusion antibodies containing a BBB receptor Ab capable of crossing the BBB fused to a decoy receptor ECD, where the BBB receptor Ab capable of crossing the blood brain barrier and the receptor ECD each retain an average of at least about 5, 10, 15, 18, 20, 25, 30, 35, 40, 40, 45, or 50% of their activities, compared to their activities as separate entities. Examples of BBB receptor Abs include Abs (e.g. monoclonal Abs) against an insulin receptor (e.g., human insulin receptor), transferrin receptor, and a lipoprotein receptor. Examples of suitable receptor ECDs include, but are not limited to, those contains an amino acid sequence at least 80% (e.g., 85%, 90%, 95%, 97%, 99%, or another percent identical from at least 80% to 100% identical to a human, mouse, rat, or pig cytokine receptor, TNF-α receptor, TNF-related apoptosis inducing ligand (TRAIL) receptor, TNF-like weak inducer of apoptosis (TWEAK) receptor, IL-6 receptor, vascular endothelial growth factor receptor, or ephrin receptor.

In some embodiments the BBB receptor Ab is an antibody to the ECD of the human insulin receptor (HIR). In the bifunctional decoy receptor-BBB receptor Ab fusion antibodies described herein, the covalent linkage between the BBB receptor antibody and the receptor ECD may be to the carboxy or amino terminal of the BBB receptor antibody heavy chain immunoglobulin or light chain immunoglobulin as long as the linkage allows the decoy receptor ECD-BBB receptor Ab fusion antibody to bind to the ECD of the BBB receptor and cross the blood brain barrier, and allows the decoy receptor ECD to retain a therapeutically useful portion of its activity, e.g., at least 10%, 20%, 30%, 40%, 50%, 60%, 70%, 80%, or another percent of its activity from at least about 10% to 100%. In certain embodiments, the covalent link is between a HC of the antibody and the decoy receptor ECD. In other embodiments, the covalent link is between a LC of the antibody and the decoy receptor ECD. Any suitable linkage may be used, e.g., carboxy terminus of light chain to amino terminus of decoy receptor ECD, carboxy terminus of heavy chain to amino terminus of decoy receptor ECD, or amino terminus of light chain to carboxy terminus of decoy receptor ECD. In preferred embodiments, the linkage is from the carboxy terminus of the HC to the amino terminus of the decoy receptor ECD. In some embodiments, the fusion antibody composition comprises a human TNF-α receptor ECD covalently linked via its N-terminus to the C-terminus of the heavy chain of a human insulin receptor antibody.

Figure 10:
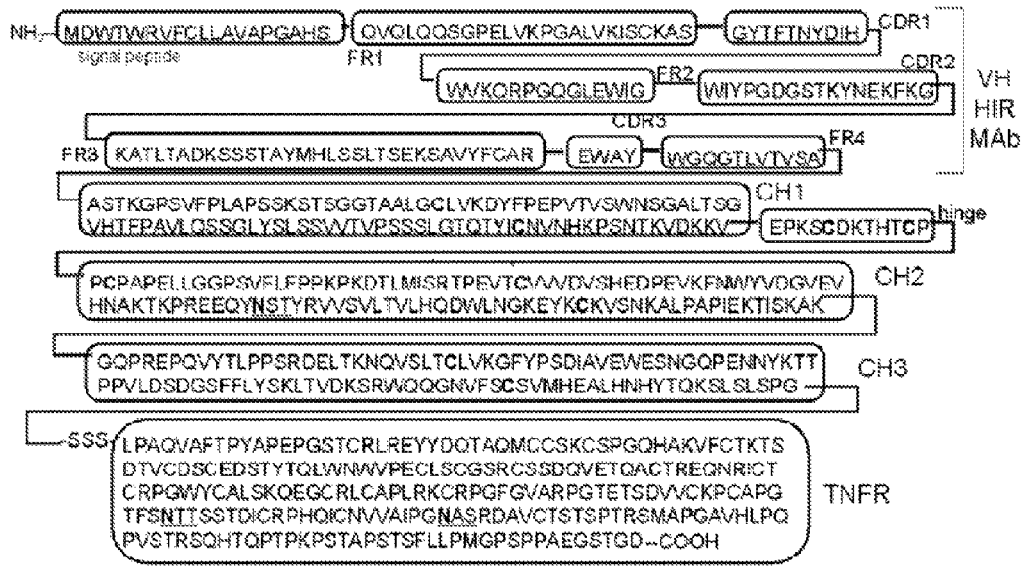
FIG. 10. Domain structure of heavy chain of the HIRMAb-TNFR fusion protein (SEQ ID NO 4). The 19 amino acid IgG signal peptide (SEQ ID NO 12) is followed by the VH of the HIRMAb heavy chain, which is comprised of 3 CDRs (CDR1, CDR2, CDR3 (SEQ ID NOS 14, 16 and 18, respectively, in order of appearance)) and 4 FRs (FR1, FR2, FR3, FR4 (SEQ ID NOS 13, 15, 17 and 19, respectively, in order of appearance)), which is followed by the domains (CH1, hinge, CH2, CH3 (SEQ ID NOS 20-23, respectively, in order of appearance)) of the human IgG1 heavy chain C-region, which is followed by a 3-amino acid linker (Ser-Ser-Ser), which is followed by the 235-amino acid sequence of the human TNFR-II ECD (SEQ ID NO: 24). The 3 N-linked glycosylation sites are underlined, and include 1 site within the CH2 region and 2 sites within the TNFR region.

It will be appreciated that a linkage between terminal amino acids can be accomplished by an intervening peptide linker sequence that forms part of the fused amino acid sequence. The peptide sequence linker may be 1, 2, 3, 4, 5, 6, 7, 8, 9, 10, or more than 10 amino acids in length. In some embodiments, a two amino acid linker is used. In some embodiments, the linker has the sequence ser-ser. The peptide linker sequence may include a protease cleavage site, however this is not a requirement for activity of the decoy receptor ECD. Indeed, an advantage of these embodiments of the present invention is that the bifunctional decoy receptor-BBB receptor antibody fusion antibody, without cleavage, is partially or fully active both for transport and for activity once across the BBB. FIG. 10 shows an exemplary embodiment of the amino acid sequence of a decoy receptor ECD-BBB receptor antibody fusion antibody, which is a human TNF-α receptor ECD-HIR antibody fusion antibody (SEQ ID NO:4) in which the HC is fused through its carboxy terminus via a three amino acid "ser-ser-ser" linker to the amino terminus of the TNF-α receptor ECD.

In some embodiments, a decoy receptor-BBB receptor Ab fusion antibody comprises both a HC and a LC. In some embodiments, the decoy receptor-BBB receptor Ab fusion antibody is a monovalent antibody. In other embodiments, the decoy receptor-BBB receptor Ab fusion antibody is a divalent antibody, as described herein in the Examples section.

The BBB receptor Ab used as part of the decoy-BBB receptor Ab fusion antibody can be glycosylated or nonglycosylated; in some embodiments, the antibody is glycosylated, e.g., in a glycosylation pattern produced by its synthesis in a CHO cell.

As used herein, "activity" includes physiological activity (e.g., ability to cross the BBB and/or therapeutic activity), binding affinity of the BBB receptor Ab for its target BBB receptor, or the affinity of the decoy receptor for a cognate ligand (e.g., TNF in the case of a TNF-α decoy receptor). Transport of a decoy receptor-BBB receptor Ab fusion antibody across the BBB may be compared to transport across the BBB of the BBB receptor Ab alone by standard methods. For example, pharmacokinetics and brain uptake of the decoy receptor-BBB receptor Ab fusion antibody by a model animal, e.g., a mammal such as a non-human primate, may be used. Similarly, standard models for determining decoy receptor ligand binding (e.g., ELISA) may be used to compare the function of a decoy receptor ECD alone and as part of a decoy receptor-BBB receptor Ab fusion antibody. See, e.g., Example 4, which demonstrates the binding of TNFα to the HIRMAb-TNF-decoy receptor fusion protein versus TNF receptor (TNFR)-II:human IgG1 Fc fusion protein, designated TNFR:Fc. Binding affinity for the BBB receptor can also be compared for the decoy receptor-BBB receptor Ab fusion antibody versus the BBB receptor Ab alone. See, e.g., Example 4.

In some cases, the brain uptake of a decoy receptor-BBB receptor AB fusion antibody (e.g., HIRMAb-TNFR fusion protein) is more than 1%. 2%. 3%. 5%, 7% or 10% ID/100 gram protein. Transport of a decoy receptor-BBB receptor Ab fusion antibody across the BBB may also be compared to transport across the BBB of a fusion protein of a decoy receptor and the Fc fragment of human IgG, e.g., TNFR:Fc. The brain uptake of a decoy receptor-BBB receptor AB fusion antibody (e.g., HIRMAb-TNFR fusion protein) may be more than 1-, 2-. 5-, 10-, 13-, 15-, 17-, 20-, 25-, 30-, 35-, 40-, 45-, or 50-fold greater than the brain uptake of a fusion protein of a decoy receptor and the Fc fragment of human IgG, e.g., TNFR:Fc. The organ clearance constant, referred to herein as the permeability-surface area (PS) product, for the brain and other organs may be computed for the fusion proteins described herein. A decoy receptor-BBB receptor AB fusion antibody described herein (e.g., HIRMAb-TNFR fusion protein) may be selectively enriched in the brain when compared to other organs. For example, when the ratio of the organ PS product for a decoy receptor-BBB receptor AB fusion antibody described herein (e.g., HIRMAb-TNFR fusion protein) relative to the organ PS product for the TNFR:Fc fusion protein is determined for multiple organs (see, e.g., FIG. 14), the brain ratio may be more than 1-, 2-. 5-, 10-, 13-, 15-, 17-, 20-, 25-, 30-, 35-, 40-, 45-, or 50-fold greater than the ratio for other organs such as fat, muscle, heart, lung, liver, or spleen.

Also included herein are pharmaceutical compositions that contain one or more decoy receptor-BBB receptor Ab fusion antibodies described herein and a pharmaceutically acceptable excipient. A thorough discussion of pharmaceutically acceptable carriers/excipients can be found in Remington's Pharmaceutical Sciences, Gennaro, A R, ed., 20th edition, 2000: Williams and Wilkins Pa., USA. Pharmaceutical compositions of the invention include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compositions of the invention are particularly suited for injection, e.g., as a pharmaceutical composition for intravenous, subcutaneous, intramuscular, or intraperitoneal administration. Aqueous compositions of the present invention comprise an effective amount of a composition of the present invention, which may be dissolved or dispersed in a pharmaceutically acceptable carrier or aqueous medium. The phrases "pharmaceutically" or "pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include calcium salts, for example, such as calcium chlorides, calcium bromides, calcium sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be systemically administered in a manner compatible with the dosage formulation and in such amount as is therapeutically effective based on the criteria described herein. The formulations are easily administered in a variety of dosage forms, such as the type of injectable solutions described above, but drug release capsules and the like can also be employed The appropriate quantity of a pharmaceutical composition to be administered, the number of treatments, and unit dose will vary according to the CNS uptake characteristics of a decoy receptor-BBB receptor Ab fusion antibody as described herein, and according to the subject to be treated, and the disease state of the subject. The person responsible for administration will, in any event, determine the appropriate dose for the individual subject.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284,262), transdermal administration (See U.S. Pat. Nos. 6,348,210; and 6,322,808) and transmucosal administration (See U.S. Pat. No. 5,656,284). Such methods of administration are well known in the art. One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

VI. NUCLEIC ACIDS, VECTORS, CELLS, AND MANUFACTURE

The invention also provides nucleic acids, vectors, cells, and methods of production. In some embodiments, the invention provides nucleic acids that code for polypeptides described herein, e.g., a nucleic acid that includes: (i) a first sequence encoding a heavy chain immunoglobulin and a receptor extracellular domain in frame with the heavy chain immunoglobulin; (ii) a second sequence encoding a light chain immunoglobulin and a receptor extracellular domain in frame with the light chain immunoglobulin; or (iii) the complementary sequence of (i) or (ii). The heavy chain and light chain immunoglobulins encoded by the just-mentioned nucleic acid are from an antibody against a BBB receptor, e.g., a human insulin receptor, transferrin receptor, an insulin-like growth factor (IGF) receptor, a leptin receptor, or lipoprotein receptor. In some cases, the encoded receptor ECD is from a TNF-α receptor, a TNF-related apoptosis inducing ligand (TRAIL) receptor, a TNF-like weak inducer of apoptosis (TWEAK) receptor, an IL-6 receptor, a vascular endothelial growth factor receptor, or an ephrin receptor. In some cases, the amino acid sequence of the encoded receptor is least about 80%, 85%, 90%, 95%, or some other percent identical from at least about 80% to about 100% identical to the amino acid sequence of an ECD from one of the foregoing receptors. In some cases, the nucleic acid encodes an ECD comprising an amino acid sequence that is least about 80%, 85%, 90%, 95%, or some other percent identical from at least about 80% to about 100% identical to the extracellular domain of a human, mouse, rat, or pig TNF-α receptor. In some embodiments, the first sequence encodes an amino acid sequence that is least about 80%, 85%, 90%, 95%, or some other percent identical from at least about 80% to about 100% identical to the amino acid sequence corresponding to SEQ ID NOs:4 or 7. In other embodiments, the second sequence encodes an amino acid sequence that is least about 80%, 85%, 90%, 95%, or some other percent identical from at least about 80% to about 100% identical to the amino acid sequence corresponding to SEQ ID NO:6.

A nucleic acid provided herein can, in some cases, further contain a nucleic acid sequence that codes for a peptide linker between the heavy chain of the MAb and the receptor ECD. In some embodiments, the linker is S-S-M. In other embodiments, the linker is S-S. In another embodiment, the linker is S-S-S. The nucleic acid may further contain a nucleic acid sequence coding for a signal peptide, wherein the signal peptide is linked to the heavy chain. Any suitable signal peptide, as known in the art or subsequently developed, may be used. In some embodiments, the signal peptide attached to the heavy chain immunoglobulin comprises a sequence that is about 60, 70, 80, 90, 95, 99, or 100% identical to amino acids 1-19 of SEQ ID NO:4. In some embodiments, the nucleic acid contains a nucleic acid sequence coding for another signal peptide, wherein the other signal peptide is linked to the light chain. The signal peptide linked to the light chain can comprise a sequence that is about 60, 70, 80, 90, 95, 99, or 100% identical to amino acids 1-20 of SEQ ID NO:6.

The invention also provides nucleic acid vectors. The vector can contain any of the nucleic acid sequences described herein. In some embodiments, the vector includes: (i) a first sequence (or its complement) encoding a heavy chain immunoglobulin from an antibody against a BBB receptor and a receptor extracellular domain in frame with the heavy chain immunoglobulin, or (ii) a second sequence (or its complement) encoding a light chain immunoglobulin from an antibody against the BBB receptor and a receptor extracellular domain in frame with the light chain immunoglobulin. In some embodiments, the invention provides nucleic acid sequences, and in some embodiments the invention provides nucleic acid sequences that are at least about 60, 70, 80, 90, 95, 99, or 100% identical to a particular nucleotide sequence. For example, in some embodiments, the invention provides a nucleic acid containing a sequence that is at least about 60, 70, 80, 90, 95, 99, or 100% identical to SEQ ID NOs:3 or 5.

In some embodiments, the invention provides a single tandem expression vector containing both (i) a first sequence (or its complement) encoding a heavy chain immunoglobulin from an antibody against a BBB receptor and a receptor extracellular domain in frame with the heavy chain immunoglobulin, and (ii) a second sequence (or its complement) encoding a light chain immunoglobulin from an antibody against the BBB receptor and a receptor extracellular domain in frame with the light chain immunoglobulin, all incorporated into a single piece of nucleic acid, e.g., a single piece of DNA referred to herein as a "tandem vector." The single tandem vector can also include one or more selection and/or amplification genes, e.g., DHFR, neomycin phosphotransferase, hygromycin phosphotransferase, or puromycin N-acetyl transferase. In some embodiments the encoded selectable marker is DHFR. In some embodiments, the tandem vector encodes DHFR and a second selection/amplification marker (e.g., neomycin phosphotransferase). A method of making an exemplary tandem vector of the invention is provided in the Examples. However, any suitable techniques, as known in the art, may be used to construct the vector.

The use of a single tandem vector has several advantages. The transfection of a eukaryotic cell line with immunoglobulin G (IgG) genes generally involves the co-transfection of the cell line with separate plasmids encoding the heavy chain (HC) and the light chain (LC) comprising the IgG. In the case of a IgG fusion protein, the gene encoding the recombinant therapeutic protein may be fused to either the HC or LC gene. However, this co-transfection approach makes it difficult to select a cell line that has equally high integration of both the HC and LC-fusion genes, or the HC-fusion and LC genes. The approach to manufacturing the fusion protein utilized in certain embodiments of the invention is the production of a cell line that is permanently transfected with a single plasmid DNA that contains all the required genes on a single strand of DNA, including the HC-fusion protein gene, the LC gene, the selection gene, e.g. neo, and the amplification gene, e.g. the dihydrofolate reductase gene. As shown in the diagram of the fusion protein tandem vector in FIG. 9, the HC-decoy receptor fusion gene, the LC gene, the neo gene, and the DHFR gene are all under the control of separate, but tandem promoters and separate but tandem transcription termination sequences. Therefore, all genes are equally integrated into the host cell genome, including the fusion gene of the therapeutic protein and either the HC or LC IgG gene.

The invention further provides cells that incorporate one or more of the vectors of the invention. The cell may be a prokaryotic cell or a eukaryotic cell. In some embodiments, the cell is a eukaryotic cell. In some embodiments, the cell is a mouse myeloma hybridoma cell. In some embodiments, the cell is a Chinese hamster ovary (CHO) cell. Exemplary methods for incorporation of the vector(s) into the cell are given in the Examples. However, any suitable techniques, as known in the art, may be used to incorporate the vector(s) into the cell. In some embodiments, the invention provides a cell capable of expressing an immunoglobulin fusion protein, where the cell is a cell into which has been permanently introduced a single tandem expression vector, where both the immunoglobulin light chain gene and the gene for the immunoglobulin heavy chain fused to the therapeutic agent, are incorporated into a single piece of nucleic acid, e.g., DNA. In some embodiments, the invention provides a cell capable of expressing an immunoglobulin fusion protein, where the cell is a cell into which has been stably introduced a single tandem expression vector, where both the immunoglobulin heavy chain gene and the gene for the immunoglobulin light chain fused to the decoy receptor ECD, are incorporated into a single piece of nucleic acid, e.g., DNA. The introduction of the tandem vector into a cell may be by, e.g., integration into a chromosomal nucleic acid, or by, e.g., introduction of an episomal genetic element.

For sequence comparison, of two nucleic acids, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman, (1970), *Adv. Appl. Math.*, 2:482c, by the homology alignment algorithm of Needleman and Wunsch, (1970), *J. Mol. Biol.*, 48:443, by the search for similarity method of Pearson and Lipman, (1988), *Proc. Nat'l. Acad. Sci. USA,* 85:2444, by computerized implementations of these algorithms (GAP, BEST-FIT, FASTA, and TFASTA in the Wisconsin Genetics Software Package, Genetics Computer Group, 575 Science Dr., Madison, Wis.), or by manual alignment and visual inspection (see, e.g., Ausubel et al., (1995 supplement), *Current Protocols in Molecular Biology*).

One example of an algorithm that is suitable for determining percent sequence identity and sequence similarity are the BLAST and BLAST 2.0 algorithms, which are described in Altschul et al., (1977), *Nuc. Acids Res.*, 25:3389-3402, and Altschul et al., (1990), *J. Mol. Biol.*, 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. The BLAST algorithm is typically performed with the "low complexity" filter turned off. The BLAST algorithm also performs a statistical analysis of the similarity between two sequences (see, e.g., Karlin and Altschul, (1993), *Proc. Natl. Acad. Sci. USA,* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

As is well-known in the art, owing to the degeneracy of the genetic code, any combination of suitable codons may be used to code for the desired fusion protein. In addition, other elements useful in recombinant technology, such as promoters, termination signals, and the like, may also be included in the nucleic acid sequence. Such elements are well-known in the art. In addition, all nucleic acid sequences described and claimed herein include the complement of the sequence.

In some embodiments, nucleic acids of the invention hybridize specifically under low, medium, or high stringency conditions to a nucleic acid encoding the amino acid sequence of SEQ ID NOs:4, 6, or 7. For example, such a nucleic acid may hybridize under low, medium, or high stringency conditions to a nucleic acid comprising the nucleotide sequences of SEQ ID NOs: 3, 5, both, or their complements. Low stringency hybridization conditions include, e.g., hybridization with a 100 nucleotide probe of about 40% to about 70% GC content at 42° C. in 2×SSC and 0.1% SDS. Medium stringency hybridization conditions include, e.g., at 50° C. in 0.5×SSC and 0.1% SDS. High stringency hybridization conditions include, e.g., hybridization with the above-mentioned probe at 65° C. in 0.2×SSC and 0.1% SDS. Under these conditions, as the hybridization temperature is elevated, a nucleic acid with a higher homology can be obtained.

In addition, the invention provides methods of manufacturing a bifunctional decoy receptor fusion antibody. In some embodiments, the invention includes for manufacturing a bifunctional decoy receptor fusion antibody, comprising stably integrating into a eukaryotic cell a single tandem expression vector encoding: (i) both an immunoglobulin heavy chain fused to a receptor extracellular domain, and an immunoglobulin light chain; or (ii), both an immunoglobulin light chain fused to a receptor extracellular domain, and an immunoglobulin heavy chain, where the encoded immunoglobulin heavy chain and immunoglobulin light chain are from an antibody against a receptor expressed on the BBB. Suitable antibodies against a BBB-receptor, and receptor ECDs include any of the foregoing antibodies and receptor ECDs.

The methods include expressing the immunoglobulin fusion protein, and/or purifying the immunoglobulin fusion protein. Exemplary methods for manufacture, including expression and purification, are given in the Examples.

However, any suitable technique, as known in the art, may be used to manufacture, optionally express, and purify the proteins. These include non-recombinant techniques of protein synthesis, such as solid phase synthesis, manual or automated, as first developed by Merrifield and described by Stewart et al., (1984) in Solid Phase Peptide Synthesis. Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of α-protecting groups have been described, see Stewart et al., (1984) in Solid Phase Peptide Synthesis, with the acid labile, urethane-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid side chain functional groups require blocking until the synthesis is completed. The complex array of functional blocking groups, along with strategies and limitations to their use, have been reviewed by Bodansky (1976) in Peptide Synthesis and, Stewart et al., (1984) in Solid Phase Peptide Synthesis.

Solid phase synthesis is initiated by the coupling of the described C-terminal α-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloro-methane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

VII. METHODS

Described herein are methods for delivering a decoy receptor across the BBB by systemically administering any of the decoy receptor-BBB receptor Ab fusion antibodies described herein. In some embodiments, the compositions described herein are administered to treat a CNS condition by systemically administering to a subject in need thereof a pharmaceutical composition comprising a bifunctional decoy receptor fusion antibody comprising the amino acid sequence of a heavy chain immunoglobulin or a light chain immunoglobulin covalently linked to the amino acid sequence of a receptor extracellular domain, where the fusion antibody binds to a receptor expressed on the BBB and the ligand for the receptor extracellular domain. In some cases, the CNS condition to be treated is an acute CNS condition, e.g., focal ischemia, global ischemia, traumatic brain injury, or spinal cord injury. In some cases, the CNS condition to be treated is a chronic CNS condition. In some embodiments, the chronic CNS condition is a neurodegenerative condition, e.g., Alzheimer's disease, Parkinson's disease, amyotrophic lateral sclerosis, Huntington's disease, multiple sclerosis, transverse myelitis, motor neuron disease, Pick's disease, tuberous sclerosis, Canavan's disease, Rett's syndrome, spinocerebellar ataxias, Friedreich's ataxia, optic atrophy, or retinal degeneration.

In some embodiments, a TNF-α receptor ECD-BBB receptor fusion antibody is systemically administered to treat a subject suffering from a stroke, head injury, spinal cord injury, or a neurodegenerative condition. In other embodiments, a vascular endothelial growth factor receptor (VEGFR)-ECD-BBB receptor Ab fusion antibody is systemically administered to a subject to block angiogenesis in a brain tumor. In some cases, a TNF related apoptosis inducing ligand receptor (TRAIL-R) ECD-BBB receptor Ab fusion antibody is systemically administered to treat dementia from acquired immune deficiency syndrome (AIDS). In some embodiments, an interleukin (IL)-6 decoy receptor ECD-BBB receptor Ab fusion antibody is systemically administered to treat multiple sclerosis (MS). In further embodiments, a TNF-like weak inducer of apoptosis (TWEAK) receptor decoy ECD-BBB receptor Ab fusion antibody is systemically administered to treat stroke. In yet another embodiment, an ephrin receptor, EphA ECD-BBB receptor Ab fusion antibody is systemically administered to accelerate neural repair following stroke or brain injury.

Suitable systemic doses for delivery of a decoy receptor-BBB receptor Ab fusion antibody will vary based on the specific decoy receptor-BBB receptor Ab fusion antibody to be administered its CNS uptake characteristics and its affinity for the decoy receptor ligand.

In some embodiments, the decoy receptor-BBB receptor Ab fusion antibody to be administered contains an antibody against an insulin receptor (e.g., a human insulin receptor), a transferrin receptor, an insulin-like growth factor (IGF) receptor, a leptin receptor, or a lipoprotein receptor, and the decoy receptor contains an ECD from a TNF-α receptor, a TNF-related apoptosis inducing ligand (TRAIL) receptor, a TNF-like weak inducer of apoptosis (TWEAK) receptor, an IL-6 receptor, a vascular endothelial growth factor receptor, or an ephrin receptor. In some embodiments, the decoy receptor-BBB receptor Ab fusion antibody to be administered is a TNF-α receptor-human insulin receptor Ab fusion antibody.

The term "systemic administration" or "peripheral administration," as used herein, includes any method of administration that is not direct administration into the CNS, i.e., that does not involve physical penetration or disruption of the BBB. "Systemic administration" includes, but is not limited to, intravenous, intra-arterial intramuscular, subcutaneous, intraperitoneal, intranasal, transbuccal, transdermal, rectal, transalveolar (inhalation), or oral administration. Any suitable decoy receptor-BBB receptor Ab fusion antibody, as described herein, may be used.

The compositions of the invention may be administered as part of a combination therapy. The combination therapy involves the administration of a composition of the invention in combination with another therapy for treatment or relief of symptoms typically found in a patient suffering from any of the above-mentioned CNS conditions. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

In some embodiments, the composition, e.g., a bifunctional TNF-α receptor ECD-BBB receptor Ab fusion antibody is co-administered to the patient with another medication, either within the same formulation or as a separate composition. For example, the bifunctional TNF-α receptor-human insulin receptor Ab fusion antibody can be formulated with another bifunctional decoy receptor-BBB receptor Ab fusion antibody. Further, the TNF-α receptor ECD-BBB receptor Ab fusion antibody may be formulated in combination with other large or small molecules. Exemplary agents for use in combination with a decoy receptor-BBB receptor Ab fusion antibody to treat CNS or CNS-related conditions are provided below.

Exemplary Agents for Co-Administration to Treat a CnS Inflammatory Condition

Where a subject is suffering from or at risk of suffering from an autoimmune, inflammatory disease, or allergic condition that affects the nervous system (see, e.g., Allan et al. (2003), *Philos Trans R Soc Lond B Biol Sci*, 358(1438): 1669-1677), a decoy receptor-BBB receptor Ab fusion antibody described herein (e.g., a TNF-α receptor ECD-BBB receptor Ab fusion antibody) can be used together with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Exemplary Agents that be can Co-Administered with for Treating Multiple Sclerosis Where a subject is suffering from or at risk of suffering from multiple sclerosis, a decoy receptor-BBB receptor Ab fusion antibody described herein (e.g., an interleukin (IL)-6 decoy receptor ECD-BBB receptor Ab fusion antibody) can be used together with one or more of the following exemplary multiple sclerosis therapeutic agents in any combination: Interferon β-1a, Interferon β-1b, glatiramer acetate (Copaxone®), mitoxantrone (Novantrone®), low dose naltrexone, Natalizumab (Tysabri®), Sativex®, Aimspro (Goats Serum), Trimesta (Oral Estriol), Laquinimod, FTY720 (Fingolimod), MBP8298, NeuroVax™, Tovaxin™, Revimmune, CHR-1103, BHT-3009, BG-12, Cladribine, daclizumab (Zenapax) Rituximab (Rituxan), cyclophosphamide, Campath, Fampridine-SR, MN-166, Temsirolimus, or RPI-78M.

Exemplary Agents that can be Co-Administered for Treatment of (e.g., Alzheimer's Disease or Aids-Related Dementia)

Where a subject is suffering from or at risk of suffering from dementia, a decoy receptor-BBB receptor Ab fusion antibody described herein (e.g., a TNF related apoptosis inducing ligand receptor (TRAIL-R) ECD-BBB receptor Ab fusion antibody) can be used together with one or more agents or methods for treating dementia in any combination. Examples of therapeutic agents/treatments for treating dementia include, but are not limited to any of the following: Flurizan™ (MPC-7869, r flurbiprofen), memantine, galantamine, rivastigmine, donezipil, tacrine, $A\beta_{1-42}$ immunotherapy, resveratrol, (−)-epigallocatechin-3-gallate, statins, vitamin C, or vitamin E.

Exemplary Agents for Treating Thromboembolic Disorders

Where a subject is suffering from or at risk of suffering from a thromboembolic disorder (e.g., stroke), the subject can be treated with a decoy receptor-BBB receptor Ab fusion antibody described herein (e.g., a TNF-like weak inducer of apoptosis (TWEAK) receptor decoy ECD-BBB receptor Ab fusion antibody) in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1

Cloning and Expression of the Human TNFR ECD cDNA

Figure 2:
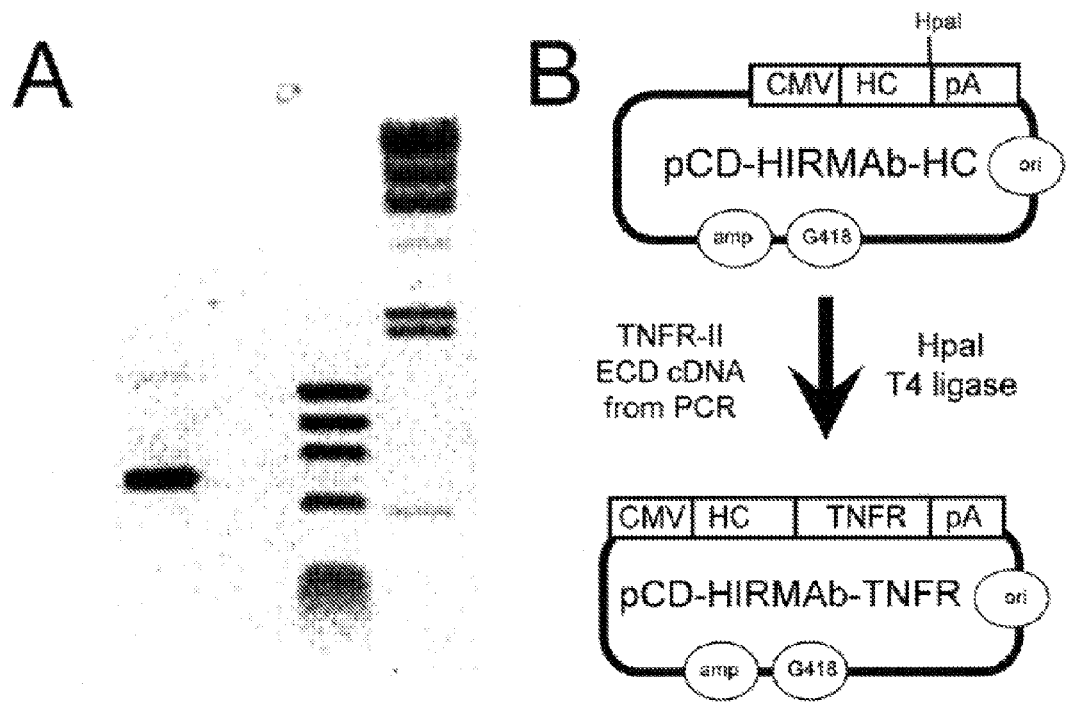
FIG. 2. (A) Ethidium bromide stain of agarose gel of human TNFR ECD cDNA (lane 1), which was produced by PCR from cDNA produced by reverse transcription of RNA from human U87 glial cells, and TNFR-specific ODN primers (Table 2). Lanes 2 and 3: DNA sizing standards. (B) Genetic engineering of pHIRMAb-TNFR, the eukaryotic expression plasmid encoding the fusion protein of TNFR ECD and the heavy chain (HC) of the chimeric HIRMAb. The fusion gene is 5'-flanked by the cytomegalovirus (CMV) promoter and 3'-flanked by the bovine growth hormone polyA (pA) sequence.

The human TNFR-II extracellular domain (ECD), corresponding to amino acids 23-257 of NP_001057, was cloned by the polymerase chain reaction (PCR) using the oligodeoxynucleotides (ODNs) described in Table 2 and cDNA derived from reverse transcription of polyA+RNA isolated from human U87 glial cells. The TNFR cDNA was cloned by PCR using 25 ng polyA+RNA-derived cDNA, 0.2 µM forward and reverse ODN primers (Table I, SEQ ID NO 1, SEQ ID NO 2, respectively), 0.2 mM deoxynucleoside-triphosphates, and 2.5 U PfuUltra DNA polymerase in a 50 µl Pfu buffer. The amplification was performed in a Mastercycler temperature cycler with an initial denaturing step of 95° C. for 2 min followed by 30 cycles of denaturing at 95° C. for 30 sec, annealing at 55° C. for 30 sec and amplification at 72° C. for 1 min; followed by a final incubation at 72° C. for 10 min. PCR products were resolved in 0.8% agarose gel electrophoresis, and the expected major single band of ~0.6 kb corresponding to the human TNFR cDNA was produced (FIG. 2A). The amino acid sequence of the TNFR ECD was deduced from the nucleotide sequence of the cloned TFR ECD cDNA, and encompassed Leu$^{23}$-Asp$^{257}$ (NP_001057).

TABLE 2

Oligodeoxynucleotide primers used in the RT-PCR cloning of human TNFR-II and in the engineering of the HIRMAb-TNFR expression vector

| | |
|---|---|
| Human TNFR FWD: phosphate-CCTTGCCCGCCCAGGTGG | SEQ ID NO 1 |
| Human TNFR REV: phosphate-TCAGTCGCCAGTGCTCCCTTC | SEQ ID NO 2 |

Example 2

Genetic Engineering of Expression Plasmids Encoding Heavy Chain-TNFR Fusion Protein Wherein the TNFR is Fused to the Carboxyl Terminus of the HIRMAb Heavy Chain The expression plasmid expressing the fusion protein of the heavy chain (HC) and the TNFR ECD is designated pCD-HIRMAb-TNFR. This plasmid was engineered by insertion of the mature human TNFR cDNA, corresponding to amino acids Leu$^{23}$-Asp$^{257}$ of the human TNFR-II ECD (NP_001057), at the HpaI site of the pCD-HIRMAb-HC expression plasmid (FIG. 2B) to produce pCD-HIRMAb-TNFR (FIG. 2B). The pCD-HIRMAb-HC plasmid encodes the HC of the chimeric HIRMAb, and dual transfection of COS cells with this plasmid and a light chain (LC) expression plasmid, pHIRMAb-LC, allows for transient expression of the chimeric HIRMAb. The TNFR forward (FWD) PCR primer (Table I) introduces "CA" nucleotides to maintain the open reading frame and to introduce a Ser-Ser-Ser linker between the carboxyl terminus of the CH3 region of the HIRMAb HC and the amino terminus of the TNFR ECD minus its signal peptide. The fusion of the TNFR monomer to the carboxyl terminus of each HC is depicted in FIG. 1. This design sterically restricts the TNFR to a dimeric configuration, which is a preferred conformation of the TNFR ECD, which crystallizes as receptor dimer (Chan et al, (2000), *Immunity*, 13:419-422). The TNFR reverse (REV) PCR primer (Table I) introduces a stop codon, "TGA," immediately after the terminal aspartic acid of the TNFR ECD protein. The engineered pCD-HIRMAb-TNFR expression vector was validated by DNA sequencing.

The HIRMAb HC and LC cDNA expression cassettes are driven by the cytomegalovirus (CMV) promoter and contain the bovine growth hormone (BGH) polyadenylation (pA) sequence (FIG. 2B). The engineering of the universal pCD-HIRMAb-HC vector was performed by insertion of a single HpaI site at the end of the HIRMAb HC CH3 open reading frame (orf) by site directed mutagenesis (SDM), as described previously (Boado et al, (2007b) *Biotechnol. Bioeng.*, 97:1376-1386).

The cDNA corresponding to the 235 amino acid TNFR-II ECD was amplified by PCR using the ODNs in Table 2, and this cDNA was subcloned into the HpaI site of the pCD-HIRMAb-HC plasmid, as outlined in FIG. 2B. DNA sequencing showed the expression cassette of the pCD-HIRMAb-TNFR plasmid encompassed 3,193 nucleotides (nt), including a 714 nt CMV promoter, a 9 nt full Kozak site (GCCGCCACC), a 2,100 nt HIRMAb HC-TNFR fusion protein open reading frame, and a 370 nt BGH sequence (SEQ ID NO 3). The 2,100 nt open reading frame corresponds to nt 724 to 2,823 of SEQ ID NO 3. The plasmid encoded for a 699 amino acid (AA) protein, comprised of a 19 amino acid IgG signal peptide (AA 1 to 19, SEQ ID NO 4), the 442 amino acid HIRMAb HC (AA 20 to 461, SEQ ID NO 4), a 3 amino acid linker (Ser-Ser-Ser), and the 235 amino acid human TNFR-II ECD minus its signal peptide (AA 465 to 699, SEQ ID NO 4). The predicted molecular weight of the heavy chain fusion protein, minus glycosylation, is 73,900 Da, with a predicted isoelectric point (pI) of 8.45. The deduced amino acid sequence of the TNFR ECD portion of the fusion protein included 22 cysteine residues and 2 N-linked consensus glycosylation sites within the TNFR ECD at Asn-149 and Asn-171 (SEQ ID NO 4).

The HIRMAb-TNFR fusion protein is comprised of 2 fusion heavy chains (AA 20-699, SEQ ID NO 4) and 2 light chains (LC). The LC is expressed by the pCD-HIRMAb-LC expression plasmid, and the nt sequence of the LC expression cassette is given in SEQ ID NO. 5. DNA sequencing of the expression cassette of the pCD-HIRMAb-LC plasmid encompassed 1,809 nt, including a 731 nt CMV promoter, a 9 nt full Kozak site (GCCGCCACC), a 705 nt HIRMAb LC fusion protein open reading frame, and a 370 nt BGH sequence (SEQ ID NO 5). The 705 nt open reading frame corresponds to nt 741 to 1,445 of SEQ ID NO 5. This plasmid encodes for a 234 AA protein, comprised of a 20 amino acid IgG signal peptide (AA 1 to 20, SEQ ID NO 6), and the 214 amino acid HIRMAb LC (AA 21 to 234, SEQ ID NO 6).

Example 3

Secretion of HIRMAb-TNFR Fusion Protein by Transfected COS Cells

COS cells were dual transfected with pCD-HIRMAb-LC and pCD-HIRMAb-TNFR using Lipofectamine 2000, with a ratio of 1:2.5, μg DNA:uL Lipofectamine, where pCD-HIRMAb-LC is an expression plasmid encoding the light chain of the chimeric HIRMAb, which is the same light chain incorporated into the HIRMAb-TNFR fusion protein. Following transfection, the cells were cultured in serum free medium. COS cells were initially plated in 6-well cluster dishes for screening for expression with a human IgG specific ELISA. Subsequently, the transfection was scaled up for plating of transfected COS cells in 10×T500 flasks. The conditioned serum free medium was collected at 3 and 7 days. The fusion protein was purified by protein A affinity chromatography.

Human IgG ELISA was performed in Immulon 2 high binding plates with COS cell conditioned medium. A goat anti-human IgG primary antibody was plated in 0.1 M NaHCO3 (100 μA, 2 μg/ml) and incubated overnight at 4 C. Plates were washed 0.01 M Na2HPO4/0.15 M NaCl/pH=7.4/0.05% Tween-20 (PBST), and blocked with 1% gelatin in PBST for 30 min at 22° C. Plates were incubated with 100 μl/well of either human IgG1 standard or the fusion protein for 60 minutes at room temperature (RT). After washing with PBST, a goat anti-human kappa LC antibody conjugated to alkaline phosphatase was plated for 60 min at 37° C. Color development was performed with p-nitrophenyl phosphate at pH=10.4 in the dark. The reaction was stopped with NaOH, and absorbance at 405 nm was measured in an ELISA plate reader.

Figure 3:
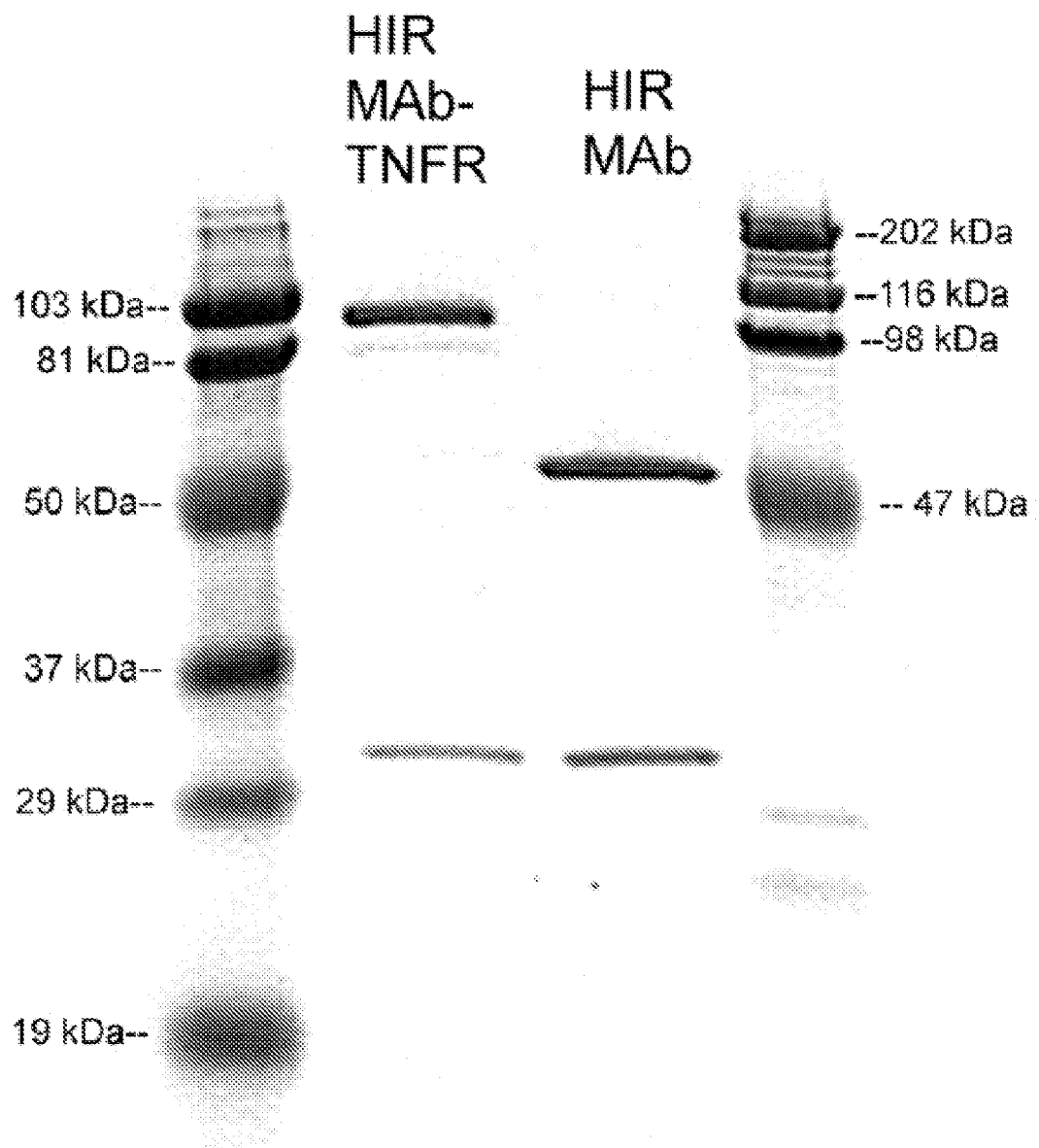
FIG. 3. Reducing SDS-PAGE and Coomasie blue staining of protein A affinity purified chimeric HIRMAb and the HIRMAb-TNFR fusion protein. Both are purified to homogeneity and are comprised of a heavy chain and a light chain.
Figure 4:
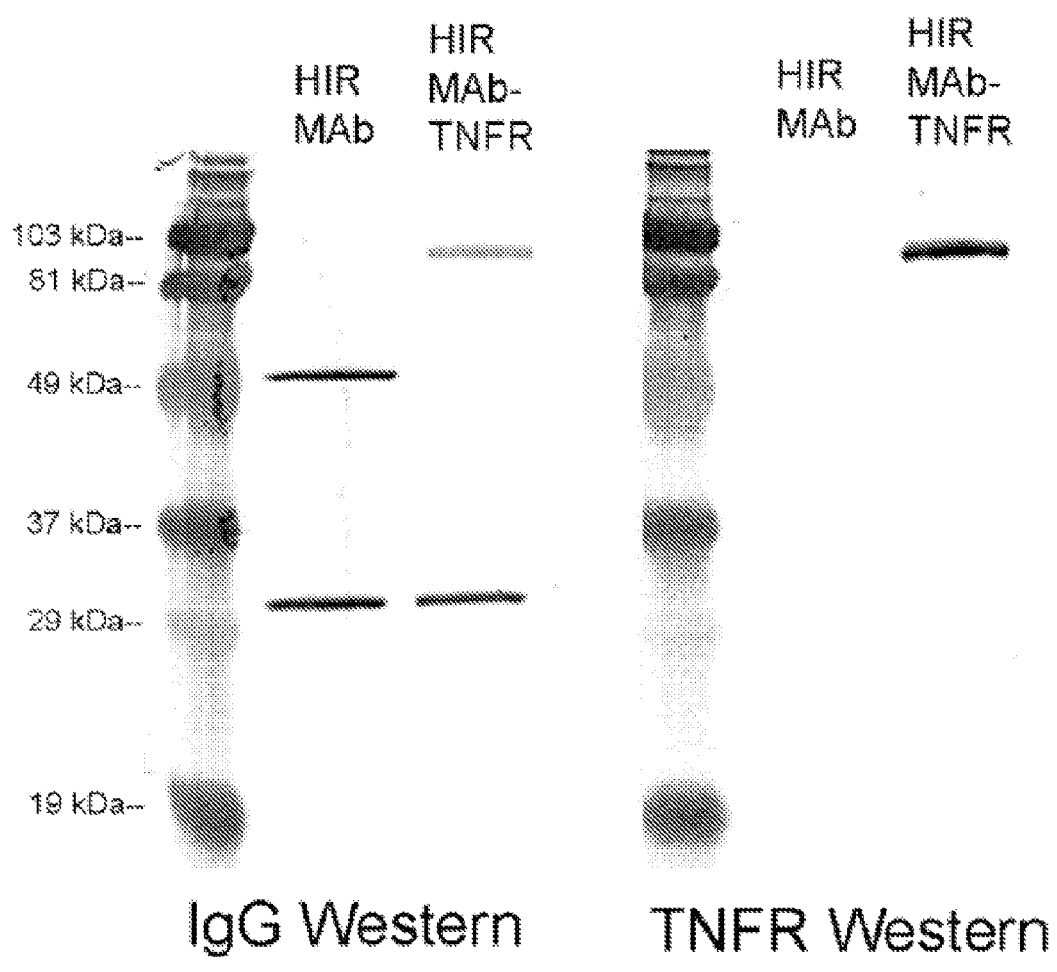
FIG. 4. Western blot with either anti-human (h) IgG primary antibody (left panel) or an anti-human TNFR-II primary antiserum (right panel). The immunoreactivity of the HIRMAb-TNFR fusion protein is compared to the chimeric HIRMAb. Both the HIRMAb-TNFR fusion protein and the HIRMAb have identical light chains on the anti-hIgG Western. The HIRMAb-TNFR fusion heavy chain reacts with both the anti-hIgG and the anti-human TNFR antibody, whereas the HIRMAb heavy chain only reacts with the anti-hIgG antibody. The size of the HIRMAb-TNFR fusion heavy chain is about 30 kDa larger than the size of the heavy chain of the HIRMAb, owing to the fusion of the 30 kDa TNFR ECD to the 55 kDa HIRMAb heavy chain.

The homogeneity of protein A purified fusion protein produced by COS cells was evaluated with a reducing 12% sodium dodecyl sulfate polyacrylamide gel electrophoresis (SDS-PAGE), followed by Coomasie Blue staining. For Western blotting, human IgG immunoreactivity was tested with a primary goat antibody to human IgG (H+L), and human TNFR immunoreactivity was evaluated with a mouse monoclonal antibody to the human TNFR-II ECD. Following SDS-PAGE and Coomasie blue staining, the size of the light chain (LC) is the same for both the HIRMAb and the HIRMAb-TNFR fusion protein (FIG. 3). The size of the heavy chain (HC) of the fusion protein is about 30 kDa larger than the HC of the HIRMAb (FIG. 3). On Western blotting, the LC of either the HIRMAb or the HIRMAb-TNFR fusion protein react equally on the Western with a primary antibody directed against the human IgG (H+L), as shown in FIG. 4 (left panel). The size of the HC of the fusion protein is about 30 kDa larger than the size of the HC of the HIRMAb on both Western blots using either the anti-human IgG primary antibody (FIG. 4, left panel) or the anti-human TNFR primary antibody (FIG. 4, right panel). These results show the HIRMAb-TNFR fusion protein is successfully translated and secreted by the host cell.

Example 4

HIRMAb-TNFR Fusion Protein Retains High Affinity Binding for Both the HIR and TNFα

In the present work, the amino terminus of the decoy receptor is fused to the carboxyl terminus of the IgG chain. Unexpectedly, this configuration yielded a bifunctional decoy receptor-BBB receptor Ab fusion antibody.

Figure 5:
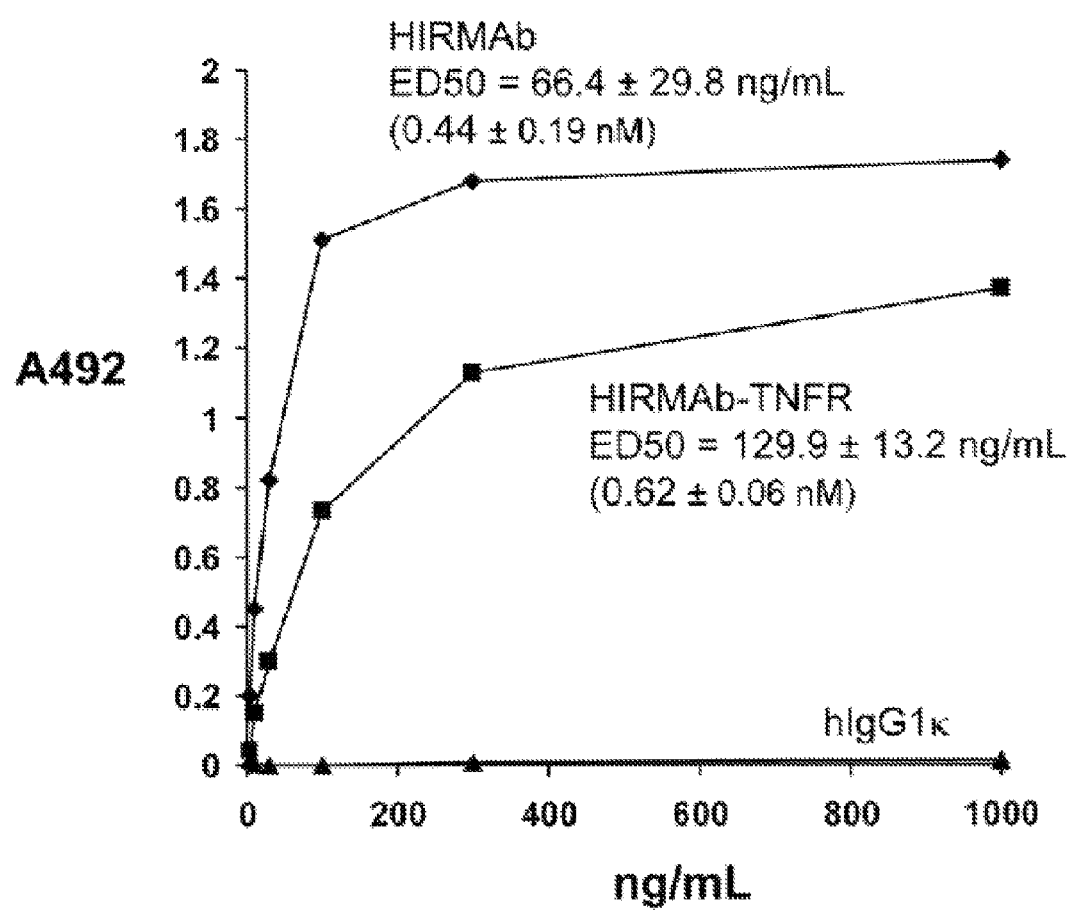
FIG. 5. Binding of either the chimeric HIRMAb or the HIRMAb-TNFR fusion protein to the HIR extracellular domain (ECD) is saturable. The ED50 of HIRMAb-TNFR binding to the HIR ECD is comparable to the ED50 of the binding of the chimeric HIRMAb.

The affinity of the fusion protein for the HIR extracellular domain (ECD) was determined with an ELISA using the lectin affinity purified HIR ECD. CHO cells permanently transfected with the HIR ECD were grown in serum free media (SFM), and the HIR ECD was purified with a wheat germ agglutinin affinity column. The HIR ECD (0.2 μg/well) was plated on Immulon 2 high binding 96-well plates, and the binding of the chimeric HIRMAb, the HIRMAb-TNFR fusion protein, or human IgG1 to the HIR ECD was detected with a biotinylated goat anti-human IgG (H+L) antibody (0.3 μg/well), and the avidin biotinylated peroxidase detection system. The concentration that caused 50% binding to the HIR ECD, the ED50, was determined by non-linear regression analysis. There is comparable binding of the chimeric HIRMAb and the HIRMAb-TNFR fusion protein for the HIR ECD with ED50 of 0.44±0.19 nM and 0.62±0.06 nM, respectively (FIG. 5). This shows there is retention of high affinity binding by the HIRMAb to the HIR, despite fusion of the TNFR to the HIRMAb.

Figure 6:
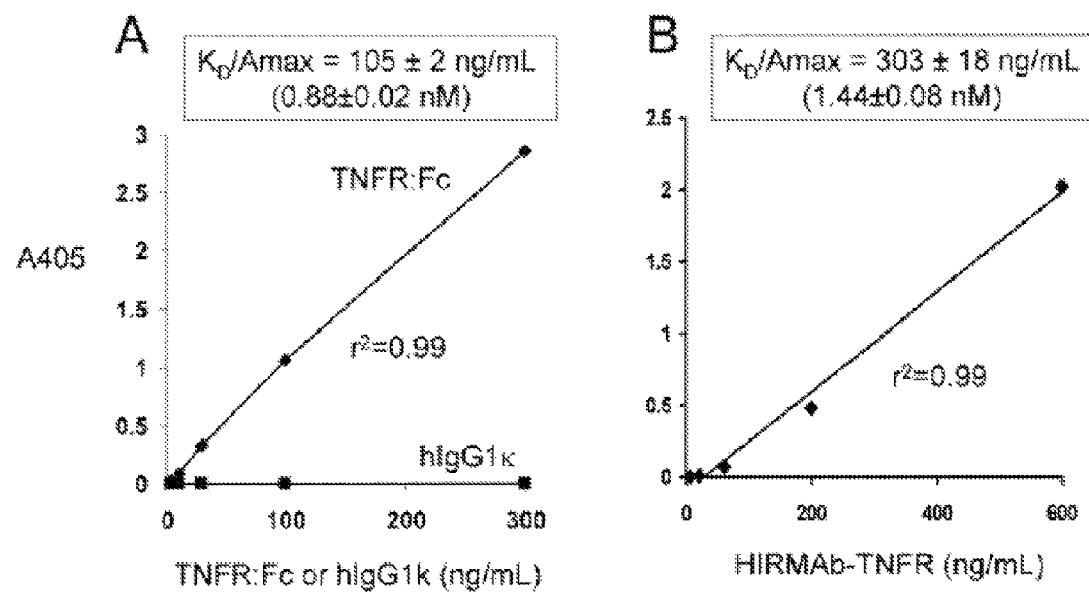
FIG. 6. Binding of either the TNFR:Fc fusion protein (A) or the HIRMAb-TNFR fusion protein (B) to the TNFα is saturable. There is no binding of human IgG1 to the TNFα, as shown in panel A. The slope of the linear regression analysis yields the KD/Amax ratio, where KD is the binding constant for TNFα and Amax is the maximal absorbance, and is a relative index of the KD of binding for TNFα. Both the TNFR:Fc fusion protein and the HIRMAb-TNFR fusion protein bind with comparable affinity to TNFα.

Binding of the HIRMAb-TNFR fusion protein to TNFα was determined with an ELISA. The capture reagent was commercially available human TNFα. The positive control in the assay was commercially available recombinant human TNFR-II:human IgG1 Fc fusion protein, designated TNFR: Fc, and the negative control was human IgG1/κ. The TNFα was dissolved in 0.1 M NaHCO3/pH=9.0 and plated overnight at 4 C in 100 μl/well (0.2 μg/well). After washing with 0.01 M Tris/0.15 M NaCl/pH=7.4 (TBS), the wells were blocked with 1% bovine serum albumin (BSA) in TBS for 30 min. A volume of 100 μl/well of HIRMAb-TNFR, TNFR:Fc, or human IgG1k was plated for 60 min at room temperature. After washing with TBS plus 0.05% Tween-20 (TBST), a goat anti-human IgG-alkaline phosphatase conjugate was incubated (0.2 μg/well) for 60 min. Following washing with TBST, color detection at 405 nm was performed with an ELISA plate reader after color development with para-nitrophenylphosphate and termination of the reaction with 1.2 M NaOH. The human IgG1/kappa (hIgG1/k) did not bind to the TNFα, as shown in FIG. 6A. The TNFR:Fc, or the HIRMAb-TNFR, bound to the plated TNFα in a linear relationship that did not saturate within the tested concentration range of 0-600 ng/mL. Therefore, the data were fit to a linear regression analysis to compute the slope of the binding curve. The reciprocal of the slope is equal to the KD/Amax ratio, where KD is the binding constant of TNFR binding to the plated TNFα, and Amax is the maximum absorbance. In this analysis, the slope of the binding curve is directly proportional to the affinity of the TNFR fusion protein for the TNFα. The affinity of either recombinant TNFR:Fc or the HIRMAb-TNFR fusion protein for human TNFα was measured with an ELISA. The TNFR:Fc bound to the TNFα with a KD/Amax ratio 0.88±0.02 nM (FIG. 6A). The HIRMAb-TNFR fusion protein bound to the TNFα with a comparable KD/Amax ratio of 1.40±0.08 nM (FIG. 6B). This shows there is retention of high affinity binding by the TNFR ECD to the TNFα, despite fusion of the TNFR to the carboxyl terminus of the HIRMAb.

Figure 7:
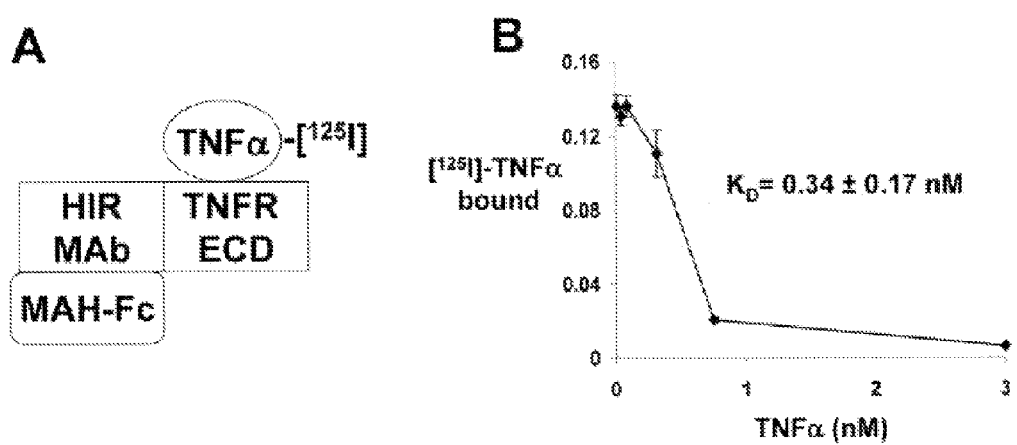
FIG. 7. (A) Outline of radio-receptor assay binding of TNFα to the HIRMAb-TNFR fusion protein. A mouse anti-human (MAH) IgG1 Fc was plated, which bound the Fc region of the HIRMAb-TNFR fusion protein. The TNFR extracellular domain (ECD) region of the fusion protein then bound the [$^{125}$I]-TNFα, which was displaced by the addition of unlabeled TNFα. (B) The saturable binding was analyzed by a non-linear regression analysis to yield the concentration, $K_D$, that gave 50% inhibition of TNFα binding to the HIRMAb-TNFR fusion protein.

The saturable binding of human TNFα to the HIRMAb-TNFR fusion protein was determined with a radio-receptor assay (RRA). A mouse anti-human IgG1 Fc antibody was plated in 96-well plates (0.4 μg/well) with an overnight incubation in 0.1 M NaHCO3/pH=8.3, followed by washing, and blocking with 1% bovine serum albumin (BSA) in 0.01 M Na2HPO4/0.15 M NaCl/pH=7.4 (PBS). Then, one of the following solutions was plated at 100 μl/well: (a) 1% BSA in PBS, (b) 100 ng/well of human IgG1/kappa, or (c) 100 ng/well of the HIRMAb-TNFR fusion protein, followed by a 1 hour incubation at room temperature. The wells were then washed with PBS, followed by the addition of 200 μl/well of a co-mixture of [$^{125}$I]-TNFα at a concentration of 0.01 uCi/well (0.2 ng/well) and various concentrations of unlabeled human TNFα, followed by a 3 hour incubation at room temperature. The wells were emptied by aspiration, washed with cold PBS, and 250 μl/well of 1 N NaOH was added, followed by heating at 60 C for 30 min. Radioactivity was counted in a Perkin Elmer liquid scintillation counter, and the fractional binding per well was computed. The half-saturation constant, KD, of TNF binding to the HIRMAb-TNFR fusion protein was determined by non-linear regression analysis using a statistical software package. Saturable binding of TNFα to the HIRMAb-TNFR fusion protein was detectable with the radio-receptor assay, which is outlined in FIG. 7A. Non-linear regression analysis of the binding data (Methods) indicated the KD of binding was 0.34±0.17 nM (FIG. 7B). These results indicate the TNFR ECD still binds its cognate ligand with very high affinity, despite fusion at its amino terminus to the carboxyl terminus of the HIRMAb heavy chain.

Example 5

Biological Activity of HIRMAb-TNFR Fusion Protein in Human Cells

Figure 8:
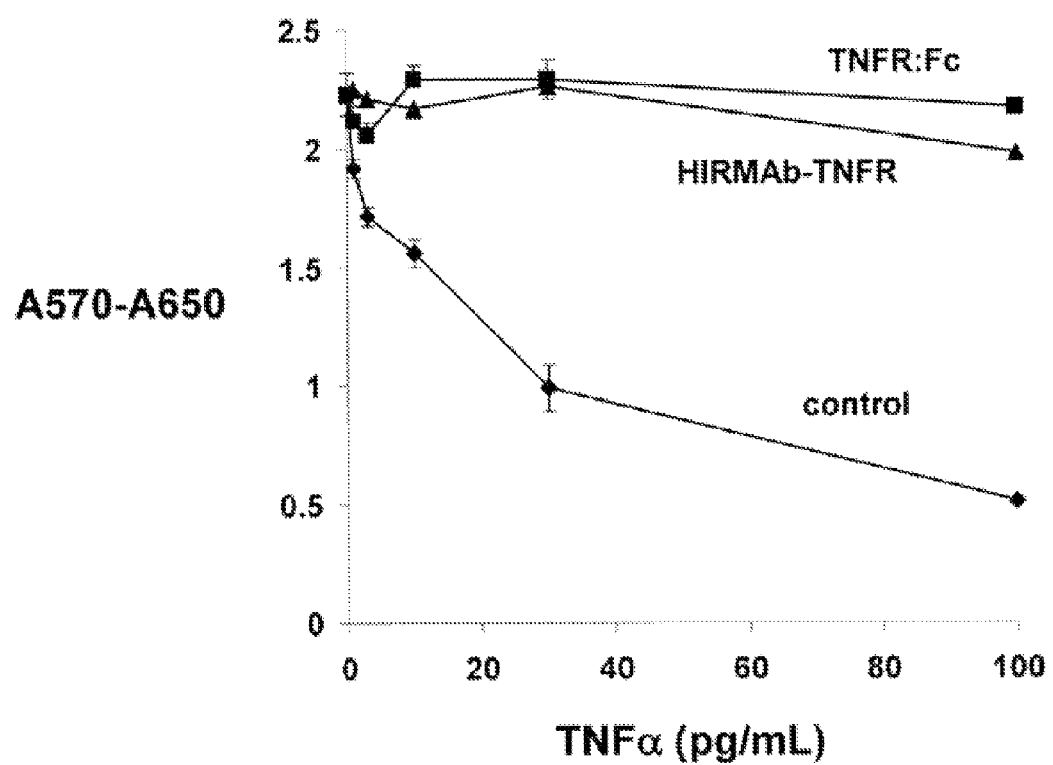
FIG. 8. TNFα causes cytotoxicity in actinomycin D-treated human WEHI-13VAR cells with an ED50 of about 10 pg/mL. However, in the presence of either 1.4 nM TNFR:Fc or 1.4 nM HIRMAb-TNFR, there is no cytotoxicity caused by the high concentrations of TNFα.

Human WEHI-13VAR cells (CRL-2148) were obtained from the American Type Culture Collection (Manassas, Va.), and used as a bio-assay of TNFα cytotoxicity (Espevik and Nissen-Meyer, (1986), *J. Immunol. Methods,* 95:99-105). The cells were plated in 24-well cluster dishes at 300,000 cells/well in RPMI-1640 medium with 10% fetal bovine serum (FBS). Following growth overnight, half of the medium was removed by aspiration, and was replaced by 200 μl of fresh RPMI-1640 medium, 50 μl/well of 10 μg/mL of actinomycin D (final concentration=1.0 μg/mL), and final concentrations of human recombinant TNFα ranging from 1 to 100 pg/mL. In some wells, the TNFα was complexed to recombinant TNFR:Fc, or the HIRMAb-TNFR fusion protein, for 30 min prior to addition to the wells. The final concentration of the TNFR:Fc or the HIRMAb-TNFR fusion protein was 1.4 nM. After overnight incubation (20 hours) at 37 C in a humidified incubator, the medium was supplemented with thiazoyl blue tetrazolium bromide (MTT) to a final concentration of 0.5 mg/mL. After a 3 hour incubation at 37 C, the reaction was terminated by the addition of solubilizing solution (48% isopropanol, 2% 1 N HCl). The absorbance at 570 nm and 650 nm, and the A570-A650 difference was computed. MTT is oxidized by mitochondria in healthy cells to formazan crystals, and this reaction is inversely related to cell viability. In the absence of actinomycin D, the TNFα, at a concentration of 1-100 pg/mL, was not toxic to the cells. However, in the presence of actinomycin D, these concentrations of TNFα produced a dose-dependent cytotoxicity with an ED50 of 5-10 pg/mL human TNFα (FIG. 8). However, the cytotoxic effect of the TNFα was blocked by the co-incubation of the cytokine with 1.4 nM concentrations of either the TNFR:Fc fusion protein or the HIRMAb-TNFR fusion protein (FIG. 8). This shows the TNFR decoy receptor is biologically active despite fusion to the carboxyl terminus of the HIRMAb.

Example 6

Site-Directed Mutagenesis of Amino Acid Sequence of TNFR

Within the 235 AA TNFR sequence of the decoy receptor cloned from human U87 glial cells (AA 465 to 699, SEQ ID NO 4), there is a polymorphism at positions 174 and 210. The arginine (Arg) at position 638 of the HIRMAb-TNFR heavy chain (SEQ ID NO 4) corresponds to Arg-174 of the 235 AA TNFR ECD. This Arg-174 is a natural R174M polymorphism, as methionine (Met) is found at position 174 in the human TNFR sequence (GenBank AAA36755). The R638M site-directed mutagenesis (SDM) can be performed by well known methods to convert the Arg-638 to Met-638, as shown in SEQ ID NO 7. The lysine (Lys) at position 674 of the HIRMAb-TNFR heavy chain (SEQ ID NO 4) corresponds to Lys-210 of the 235 AA TNFR ECD. This Lys-210 is a natural K210E polymorphism, as glutamate (Glu) is found at position 210 in the human TNFR sequence (GenBank AAA36755). The K674E site-directed mutagenesis (SDM) can be performed by well known methods to convert the Lys-674 to Glu-674, as shown in SEQ ID NO 7. The engineering of the pCD-HIRMAb-TNFR expression vector with the TNFR-R638M polymorphism (SEQ ID NO 7) is performed by SDM with the human TNFR-R638M FWD (Table 3, SEQ ID NO 8) and the human TNFR-R638M REV (Table 3, SEQ ID NO 9) ODN primers using well known site-directed mutagenesis methods. Similarly, the engineering of the pCD-HIRMAb-TNFR expression vector with the TNFR-K674E polymorphism is performed by SDM with the human TNFR-K674E FWD (Table 3, SEQ ID NO 10) and the human TNFR-K674E REV (Table 3, SEQ ID NO 11) ODN primers.

Example 7

Figure 9:
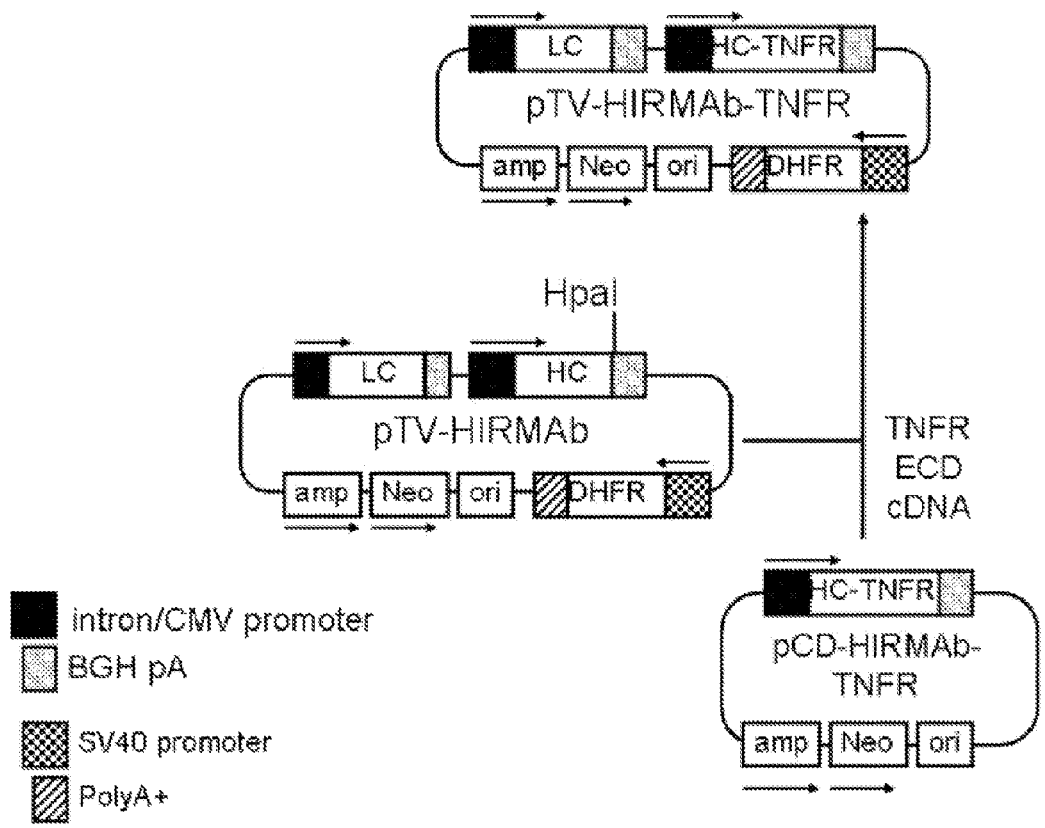
FIG. 9. Genetic engineering of pTV-HIRMAb-TNFR, which is a tandem vector (TV) containing separate and tandem expression cassettes encoding both the heavy chain and light chain of the HIRMAb-TNFR fusion protein, each gene driven by separate and tandem intron bearing/CMV promoters, and each terminated by the bovine growth hormone (BGH) poly adenylation (pA) sequence. The pTV-HIRMAb-TNFR is generated by subcloning the TNFR ECD cDNA into a unique HpaI site at the 3'-terminus of the HIRMAb HC cassette within the universal TV encoding the HIRMAb, designated pTV-HIRMAb. The TNFR ECD cDNA was produced by PCR using the pCD-HIRMAb-TNFR plasmid (FIG. 2B) as template.

Genetic Engineering of Tandem Vector Encoding the HIRMAb-TNFR Fusion Protein The HIRMAb-TNFR fusion protein is comprised of 2 heavy chains (HC) and 2 light chains (LC), as shown in FIG. 1. Therefore, the host cell must be permanently transfected with both the HC and LC genes. In addition, the host cell must be permanently transfected with a gene that allows for isolation of cell lines with amplification around the transgene insertion site. This is accomplished with selection of cell lines with methotrexate (MTX) following transfection of the host cell with a gene encoding for dihydrofolate reductase (DHFR). Therefore, it is necessary to obtain high production of all 3 genes in a single cell that ultimately produces the Master Cell Bank for manufacturing. In order to insure high expression of all 3 genes, a single piece of DNA, called a tandem vector (TV), was engineered as outlined in FIG. 9. The genetic engineering of the TV for HIRMAb-TNFR fusion protein, designated pTV-HIRMAb-TNFR, was completed by insertion of the TNFR ECD cDNA into the HpaI site of pTV-HIRMAb. The TNFR ECD cDNA was generated by PCR using custom ODNs and pCD-HIRMAb-TNFR (FIG. 2B) as the template. The pTV-HIRMAb is a tandem vector encoding the chimeric HIRMAb with a unique HpaI restriction site at the 3' terminus of the HIRMAb HC open reading frame. The pTV-HIRMAb contains tandem expression cassettes for the HIRMAb LC and HC genes, each cassette driven by an intron bearing CMV promoter, and each cassette terminated by a bovine growth hormone (BGH) poly adenylation (pA) sequence. The pTV-HIRMAb also contains a third expression cassette for murine dihydrofolate reductase (DHFR), which is driven by the SV40 promoter and is terminated by the hepatitis B virus (HBV) pA sequence. The HIRMAb-TNFR HC expression cassette is comprised of an intron bearing CMV promoter, a 9 nt full Kozak site (GCCGCCACC), a 2,100 nt HIRMAb HC-TNFR fusion protein open reading frame, and a BGH pA sequence. The 699 AA HIRMAb-TNFR HC protein encoded by the tandem vector shown in FIG. 9 is identical to the one in SEQ ID NO 4, and it is comprised of a 19 amino acid IgG signal peptide (AA 1 to 19, SEQ ID NO 4), the 442 amino acid HIRMAb HC (AA 20 to 461, SEQ ID NO 4), a 3 amino acid linker (Ser-Ser-Ser), and the 235 amino acid human TNFR-II ECD minus its signal peptide (AA 465 to 699, SEQ ID NO 4). The predicted molecular weight of the heavy chain fusion protein, minus glycosylation, is 73,900 Da, with a predicted isoelectric point (pI) of 8.45. The deduced amino acid sequence of the TNFR ECD portion of the fusion protein included 22 cysteine residues and 2 N-linked consensus glycosylation sites within the TNFR ECD at Asn-149 and Asn-171 (SEQ ID NO 4). The HIRMAb-TNFR fusion protein produced by the tandem vector described in FIG. 9 is comprised of 2 fusion heavy chains (AA 20-699, SEQ ID NO 4) and 2 light chains (LC). The LC expression cassette encompasses an intron bearing CMV promoter, a 9 nt full Kozak site (GCCGCCACC), a 705 nt HIRMAb LC fusion protein open reading frame, and a BGH pA sequence. The 214 AA HIRMAb-LC protein encoded by the tandem vector shown in FIG. 9 is identical to the one in SEQ ID NO 6, and it is comprised of a 20 amino acid IgG signal peptide (AA 1 to 20, SEQ ID NO 6), and the 214 amino acid HIRMAb LC (AA 21 to 234, SEQ ID NO 6).

Example 8

Stable Transfection of CHO Cells and Dilutional Cloning

Serum free medium (SFM) adapted DG44 Chinese hamster ovary (CHO) cells were electroporated with 5 μg of the pTV-HIRMAb-TNFR, following linearization with PvuI, using an electroporator. Five ×10$^6$ cells were electroporated with the DNA in 200 uL of phosphate buffered saline (PBS) and 0.2 cm cuvettes using a square wave and 160 volts. Cells were suspended in CHO serum free medium (SFM) and plated in 4×96-well plates. Selection of stable transfectants began 2 days following electroporation with 0.54 mg/ml G418. Aliquots of supernatant were taken for human IgG ELISA when colonies of transfectants were evident, i.e. 21 days. Positive clones were isolated and cultured individually for further characterization. DG44 cells lack endogenous DHFR, and rely on nutrients, hypoxanthine and thymidine (HT) for endogenous folate synthesis. Transfected cells carrying the TV express the exogenous DHFR. Transfected cell lines were further selected by placement in HT-deficient medium. Lines with amplification around the transgene insertion site were selected by subjecting the cells to increasing concentrations of MTX, starting at 20 nM MTX. Following stabilization of the cell line at 80-160 nM MTX, high producing clones were isolated by limited dilution cloning (DC) at 1 cell per well; a total of 4000 wells were plated at each round of DC, and medium IgG was measured with a human IgG ELISA using a high volume microplate dispenser and a microplate washer. The cloned cells were propagated in 125 mL plastic square bottles on an orbital shaker at a viable cell density of 1-2 million cells/mL, and produced human IgG levels of approximately 10 mg/L in serum free medium, as determined by IgG ELISA.

Example 9

Selective Targeting of Decoy Receptor to Brain In Vivo

The brain penetration of the HIRMAb-TNFR fusion protein was measured in the adult Rhesus monkey, since the HIRMAb cross reacts with the insulin receptor of Old World primates, but does not recognize the insulin receptor of lower species. In addition, commercially available TNFR decoy receptor fused to the human IgG1 Fc region, and designated TNFR:Fc, was purchased from R&D Systems. The TNFR:Fc fusion protein represents the state of the art with respect to decoy receptor fusion proteins. The TNFR:Fc has no specificity for any BBB receptor, and is expected not to penetrate the BBB. However, the BBB transport of the TNFR:Fc fusion protein has never been measured. Moreover, there is evidence in the literature that IgG molecules cross the BBB [Zlokovic et al, A saturable mechanism for transport of immunoglobulin G across the blood-brain barrier of the guinea pig. Exp. Neurol, 107, 263-270, 1990], and one could speculate that the TNFR:Fc fusion protein would also cross the BBB, in that this protein contains the majority of the constant region of human IgG1. For the brain uptake study, the CHO-derived HIRMAb-TNFR fusion protein was tritiated, in parallel with the non-oxidative radio-iodination of the TNFR:Fc fusion protein. The [$^3$H]-HIRMAb-TNFR and [$^{125}$I]-TNFR:Fc fusion proteins were co-injected into the Rhesus monkey. The results demonstrate that the TNFR:Fc fusion protein does not cross the BBB, and that there is a marked increase in brain penetration of the TNFR following fusion to the BBB molecular Trojan horse. The uptake of the fusion proteins in non-brain organs in the primate is also measured, which shows that fusion of the decoy receptor to the HIRMAb results in a selective targeting of the pharmaceutical to the CNS.

[$^{125}$I]-Bolton-Hunter reagent was used to radiolabel the TNFR:Fc fusion protein (#726-R2), which was purchased from R&D Systems (Minneapolis, Minn.), and shown to be homogenous by SDS-PAGE. The TNFR:Fc was radio-labeled with fresh Bolton-Hunter reagent to a specific activity of 11.5 uCi/ug and a trichloroacetic acid (TCA) precipitability of >99% following purification with a 1.0×28 cm column of Sephadex G-25 and elution with 0.01 M NaH2PO4/0.15 M NaCl/pH=7.4/0.05% Tween-20 (PBST). The TCA precipitation of the labeled TNFR:Fc fusion protein remained >99% at 24 hours after iodination, and the TNFR:Fc fusion protein was administered to the primate within 24 hrs of radio-labeling. [$^3$H]-N-succinimidyl propionate (NSP) was used to radiolabel the HIRMAb-TNFR fusion protein, which resulted in a specific activity of 3.0 uCi/ug and a TCA precipitability of 95% following purification with a 1.0×28 cm column of Sephadex G-25 and elution with 0.02 M Tris/0.15 M NaCl/pH=6.5 (TBS). The solution was buffer exchanged with TBS and an Ultra-15 microconcentrator (Millipore, Bedford, Mass.), which increased the TCA precipitability to 99%. The $^3$H-labeled HIRMAb-TNFR fusion protein was labeled in advance of the primate study and stored at −70 C.

An adult female Rhesus monkey, 4.1 kg, was injected intravenously (IV) with 1806 uCi of [$^3$H]-HIRMAb-TNFR fusion protein, 428 uCi of [$^{125}$I]-TNFR:Fc fusion protein in 3.1 mL of TBS by bolus injection over 30 seconds in the left femoral vein. The dose of HIRMAb-TNFR fusion protein was 0.15 mg/kg. The animal was initially anesthetized with intramuscular ketamine, and anesthesia was maintained by 1% isoflurane by inhalation. All procedures were carried out in accordance with the Guide for the Care and Use of Laboratory Animals as adopted and promulgated by the U.S. National Institutes of Health. Following intravenous drug administration, femoral venous plasma was obtained at 1, 2.5, 5, 15, 30, 60, and 120 min for determination of $^3$H and $^{125}$I radioactivity. The animal was euthanized, and samples of major organs (heart, liver, spleen, lung, skeletal muscle, and omental fat) were removed, weighed, and processed for determination of radioactivity. The cranium was opened and the brain was removed. Samples of frontal cortical gray matter, frontal cortical white matter, cerebellar gray matter, and cerebellar white matter were removed for radioactivity determination.

Samples (~2 gram) of frontal cortex were removed for capillary depletion analysis. The brain was homogenized in 8 mL cold PBS in a tissue grinder. The homogenate was supplemented with 9.4 mL cold 40% dextran (70 kDa, Sigma Chemical Co.), and an aliquot of the homogenate was taken for radioactivity measurement. The homogenate was centrifuged at 3200 g at 4 C for 10 min in a fixed angle rotor. The brain microvasculature quantitatively sediments as the pellet at this density of high molecular weigh dextran, and the post-vascular supernatant is a measure of capillary depleted brain parenchyma. The vascular pellet and supernatant were counted for $^3$H and $^{125}$I radioactivity in parallel with the homogenate. The volume of distribution (VD) was determined for each of the 3 fractions from the ratio of total $^{125}$I or $^3$H radioactivity in the fraction divided by the total $^{125}$I or $^3$H radioactivity in the 120 min terminal plasma.

Plasma and tissue samples were analyzed for $^{125}$I radioactivity with a gamma counter, and were analyzed for $^3$H radioactivity with a liquid scintillation counter. The $^{125}$I isotope emits radiation that is detected in the $^3$H channel (0-12 keV) of the liquid scintillation counter (LSC). Therefore, quench curves were produced using chloroform as the quench agent, to compute the efficiency of counting of $^{125}$I in the $^3$H window. All samples for $^3$H counting were solubilized in Soluene-350 (Perkin Elmer) and counted in the LSC in Opti-Fluor O (Perkin Elmer).

The $^3$H or $^{125}$I radioactivity in plasma, DPM/mL, was converted to % injected dose (ID)/mL, and the % ID/mL was fit to a bi-exponential equation, % ID/mL=$A1e^{-k1t}+A2e^{-k2t}$. The intercepts (A1, A2) and the slopes (k1, k2) were used to compute the median residence time (MRT), the central volume of distribution (Vc), the steady state volume of distribution (Vss), the area under the plasma concentration curve (AUC), and the systemic clearance (CL). Non-linear regression analysis used to compute the PK parameters, and the data were weighted by $1/(\% \text{ ID/mL})^2$.

The organ clearance (uL/min/g), also called the permeability-surface area (PS) product, is computed from the terminal organ uptake (% ID/g) and the 120 min plasma AUC (% IDmin/mL) as follows: organ PS product=[(% ID/g)/AUC]*1000. The HIRMAb-TNFR fusion protein was radiolabeled with the [$^3$H] and the TNFR:Fc fusion protein was radiolabeled with [$^{125}$I], and the proteins were co-injected IV into an adult Rhesus monkey. The clearance of the plasma radioactivity is shown in FIG. 12A, and the plasma radioactivity that was precipitable with TCA is shown in FIG. 12B. The plasma clearance profiles (FIG. 12A) were fit to a bi-exponential function (Methods) for estimation of the PK parameters, which are shown in Table 4 for each fusion protein. The uptake of the fusion proteins by brain and peripheral organs was measured as a % I.D./100 gram tissue, and these values are given in Table 5. The brain volume of distribution (VD) of the fusion proteins was measured with the capillary depletion method and the VD values for the homogenate, the vascular pellet, and the post-vascular supernatant are given in Table 6.

Figure 13:
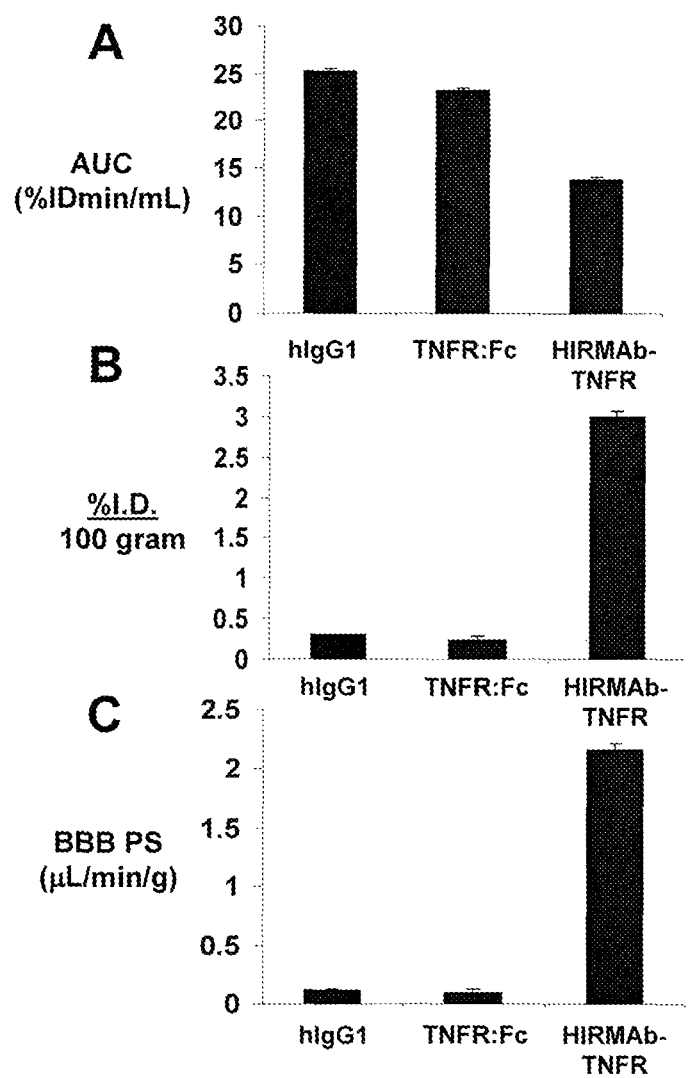
FIG. 13. The plasma area under the concentration curve or AUC (A), the brain uptake or % injected dose (I.D.) per 100 gram brain (B), and the BBB permeability-surface area (PS) product (C), are plotted for the TNFR:Fc fusion protein, for the HIRMAb-TNFR fusion protein, and a brain plasma volume marker, human IgG1 (hIgG1). All measurements were made at 2 hours after intravenous administration of the protein. Data are mean±SE (n=3 replicates per point).

The BBB PS products for the HIRMAb-TNFR and TNFR:Fc fusion proteins were computed from the 2 hour plasma AUC (FIG. 13A) and the brain uptake or % ID/100 g (FIG. 13B), and the PS products are given in FIG. 13C. For comparison, the data in FIG. 13 also display the AUC, the % ID/100 g, and the BBB PS product for a vascular space marker, human IgG1. The PS products were similarly computed for the HIRMAb-TNFR and TNFR:Fc fusion proteins in peripheral organs and these data are given in Table 7. The ratio of the PS product for the HIRMAb-TNFR fusion protein relative to the PS product for the TNFR:Fc fusion protein in each organ is plotted in FIG. 14.

TABLE 4

Pharmacokinetic parameters

| parameter | units | [$^{125}$I]-TNFR: Fc Fusion protein | [$^3$H]-HIRMAb-TNFR Fusion protein |
|---|---|---|---|
| A1 | % ID/mL | 0.211 ± 0.010 | 0.319 ± 0.015 |
| A2 | % ID/mL | 0.239 ± 0.010 | 0.146 ± 0.011 |
| k1 | min−1 | 0.082 ± 0.009 | 0.099 ± 0.011 |
| k2 | min−1 | 0.0057 ± 0.0004 | 0.0091 ± 0.0008 |
| MRT | min | 166 ± 12 | 93 ± 8 |
| Vc | mL/kg | 54 ± 1 | 52 ± 2 |
| Vss | mL/kg | 91 ± 3 | 118 ± 6 |
| AUC $^{120}$ | % IDmin/mL | 23.3 ± 0.2 | 13.9 ± 0.2 |
| AUCss | % IDmin/mL | 44.5 ± 1.9 | 19.3 ± 0.7 |
| CL | mL/min/kg | 0.55 ± 0.02 | 1.28 ± 0.04 |

Figure 12:
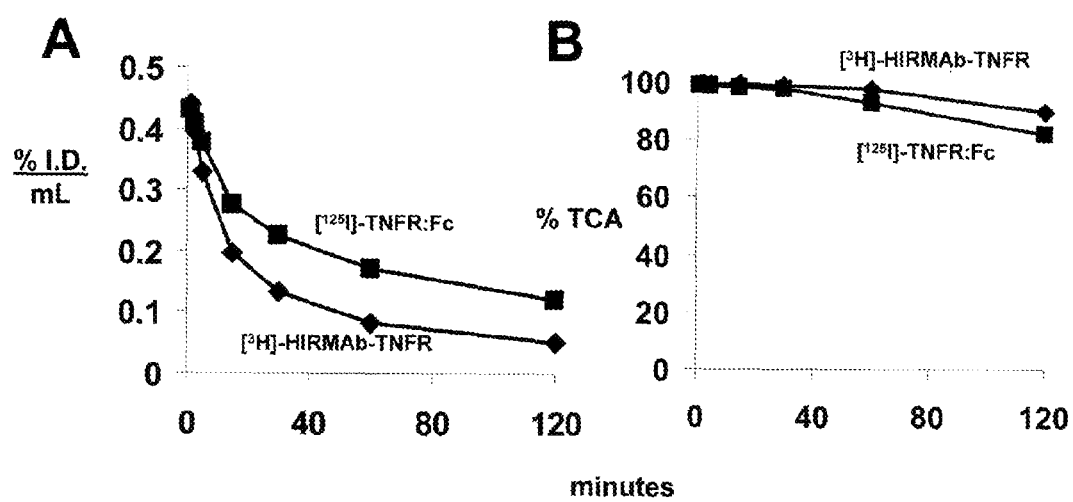
FIG. 12. (A) The plasma concentration of [$^{125}$I]-TNFR:Fc fusion protein and [$^{3}$H]-HIRMAb-TNFR fusion protein is plotted vs the time after a single intravenous injection of the proteins in the adult Rhesus monkey. Data are expressed as % injected dose (I.D.)/mL. (B) The % of plasma radioactivity that is precipitable by 10% trichloroacetic acid (TCA) is plotted vs. the time after injection for both proteins. Data are mean±SE (n=3 replicates per point).

Estimated from the plasma clearance data in FIG. 12.

TABLE 5

Organ uptake of [$^{125}$I]-TNFR: Fc and [$^3$H]-HIRMAb-TNFR in the Rhesus monkey

| organ | [$^{125}$I]-TNFR: Fc Fusion protein | [$^3$H]-HIRMAb-TNFR Fusion protein |
|---|---|---|
| Frontal gray | 0.230 ± 0.057 | 3.00 ± 0.07 |
| Frontal white | 0.070 ± 0.007 | 1.49 ± 0.19 |
| Cerebellar gray | 0.168 ± 0.009 | 2.41 ± 0.07 |
| Cerebellar white | 0.100 ± 0.004 | 2.23 ± 0.22 |
| heart | 1.06 ± 0.03 | 1.03 ± 0.08 |
| liver | 21.6 ± 0.2 | 30.3 ± 1.9 |
| spleen | 8.4 ± 0.2 | 26.6 ± 1.7 |
| lung | 3.96 ± 0.24 | 3.96 ± 0.57 |
| Skeletal muscle | 0.223 ± 0.013 | 0.17 ± 0.02 |
| fat | 0.279 ± 0.013 | 0.19 ± 0.01 |

Data are % I.D./100 grams; mean ± SE (n = 3).

TABLE 6

Capillary depletion analysis of HIRMAb-GDNF and TNFR: Fc distribution in brain

| Parameter | TNFR: Fc | HIRMAb-TNFR |
|---|---|---|
| Homogenate VD | 13 ± 3 | 354 ± 21 |
| Post-vascular supernatant VD | 8.3 ± 0.2 | 208 ± 23 |
| Brain capillary pellet VD | 0.4 ± 0.1 | 28 ± 5 |
| TCA precipitation (%) | 71 ± 2 | 93 ± 1 |

Mean ± SE (n = 3). VD = volume of distribution (uL/g); TCA = trichloroacetic acid.

TABLE 7

Organ PS products for TNFR: Fc and HIRMAb-TNFR fusion proteins

| | PS product (uL/min/g) | |
|---|---|---|
| organ | TNFR: Fc | HIRMAb-TNFR |
| Cerebral gray | 0.098 ± 0.020 | 2.2 ± 0.1 |
| Cerebral white | 0.030 ± 0.003 | 1.1 ± 0.2 |
| Cerebellar gray | 0.072 ± 0.003 | 1.7 ± 0.1 |
| Cerebellar white | 0.043 ± 0.002 | 1.6 ± 0.2 |
| Heart | 0.45 ± 0.02 | 0.72 ± 0.06 |
| Liver | 9.3 ± 0.1 | 21.8 ± 1.4 |
| Spleen | 3.6 ± 0.1 | 19.1 ± 0.8 |
| Lung | 1.7 ± 0.4 | 2.8 ± 0.4 |
| Skeletal muscle | 0.094 ± 0.004 | 0.12 ± 0.01 |
| Fat | 0.12 ± 0.01 | 0.14 ± 0.01 |

Data are mean ± SE (n = 3).

The selective transport of the HIRMAb-TNFR fusion protein across the primate BBB in vivo, relative to the TNFR:Fc fusion protein, is shown in Table 5, which gives the brain uptake of the proteins expressed as % ID/100 grams. The uptake data are expressed as 100 grams of tissue, because the weight of the Rhesus monkey brain is 100 grams. However, the brain uptake parameters in Table 5 are not direct measures of the relative brain penetration of the HIRMAb-TNFR and TNFR:Fc fusion proteins, and the following considerations should be made. First, the brain uptake, or % ID/g, is a function of the plasma AUC of the protein. Normalizing the % ID/g by the plasma AUC values in Table 4 results in the computation of the organ PS product, and the PS products are shown in FIG. 13 for brain and in Table 7 for peripheral organs. Second, the brain uptake, or % ID/g, must be corrected for the organ blood volume. Organ uptake values for a given protein could reflect simply sequestration of the protein in the blood space of the organ, which can vary widely between tissues. The organ blood volume factor is normalized by computation of the PS product for a blood volume marker, such as human IgG1, which is the isotype control of the HIRMAb. The BBB PS product for human IgG1 is shown in FIG. 13. The equivalence of the BBB PS product for human IgG1 and the TNFR:Fc fusion protein is quantitative evidence that the TNFR:Fc fusion protein does not cross the BBB. Computation of a PS product for a brain blood volume marker, such as human IgG1 or the TNFR:Fc fusion protein, is an approximation since the actual PS product for either protein, after correction for the brain blood volume, is zero. Third, the high BBB PS product for the HIRMAb-TNFR fusion protein (FIG. 13) could reflect sequestration of the fusion protein by the brain microvasculature, and not actual transcytosis across the BBB and penetration into brain parenchyma. For this reason, the capillary depletion analysis was performed. The high VD of the HIRMAb-TNFR fusion protein in the post-vascular supernatant, and low VD in the vascular pellet (Table 6), demonstrates that >90% of the HIRMAb-TNFR fusion protein taken up by brain has penetrated into the post-vascular parenchyma. The homogenate VD of the TNFR:Fc fusion protein, 13±3 uL/g (Table 6), is equal to the brain blood volume, which is further evidence that the TNFR:Fc fusion protein does not cross the BBB in the blood to brain direction.

Figure 14:
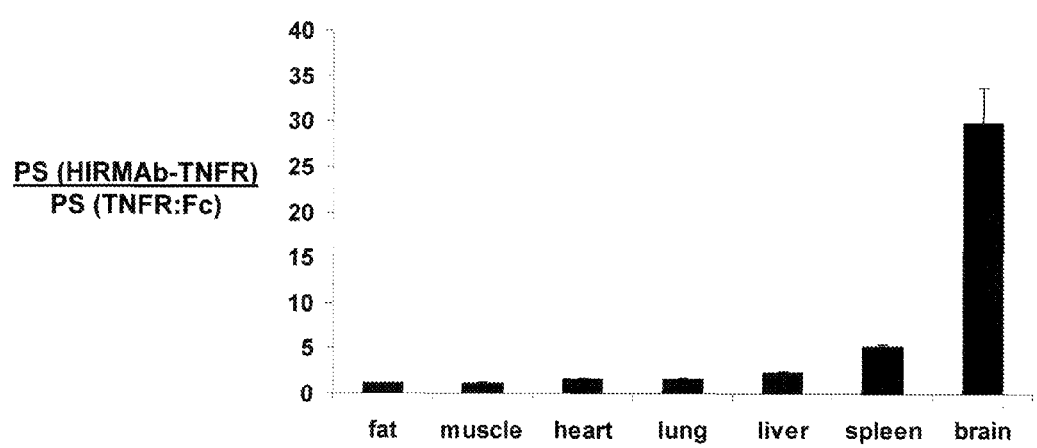
FIG. 14. Ratio of the organ PS product for the HIRMAb-TNFR fusion protein, relative to the organ PS product for the TNFR:Fc fusion protein, is plotted for each organ. Data are mean±SE (n=3 replicates per point). The ratio for brain is the mean of the values for frontal gray matter, frontal white matter, cerebellar gray matter, and cerebellar white matter, which varied between 22-37.

The PS products of the HIRMAb-TNFR and TNFR:Fc fusion proteins were also computed for peripheral organs (Table 7). The ratio of the PS product for the HIRMAb-TNFR fusion protein, relative to the PS product for the TNFR:Fc fusion protein, for brain and peripheral organs is plotted in FIG. 14. These data show that the ratio of the PS product for the HIRMAb-TNFR fusion protein, relative to the PS product for the TNFR:Fc fusion protein, is near unity for peripheral organs such as heart, lung, skeletal muscle, and fat, is modestly elevated 2- to 5-fold for organs such as liver or spleen, and is selectively, and markedly, elevated for brain (FIG. 14). The PS product ratio in brain, 30, is an under-estimate, since the actual BBB PS product for the TNFR:Fc fusion protein is zero.

The pharmacokinetic (PK) and brain uptake data for the primate allow for initial dosing considerations of therapeutic interventions with the HIRMAb-TNFR fusion protein. The brain uptake, 3.0% ID/100 gram (Table 5), at an injection dose of 0.2 mg/kg, produces a brain concentration of the HIRMAb-TNFR fusion protein of 1.1 pmol/gram fusion protein, which is equivalent to 2.2 pmol/gram, since there are 2 TNFR moieties per individual fusion protein (FIG. 1). The concentration of immunoreactive TNFα in normal brain is undetectable, but increases to 0.4 pmol/gram in traumatic brain injury [E. Shohami, M. Novikov, R. Bass, A. Yamin, and R. Gallily. Closed head injury triggers early production of TNF alpha and IL-6 by brain tissue. *J. Cereb. Blood Flow Metab.* 14: 615-9 (1994)]. Since the affinity of the HIRMAb-TNFR fusion protein for TNFα is high (FIG. 4B), a low dose of the HIRMAb-TNFR fusion protein of 0.2 mg/kg will sequester most of the cerebral TNFα in brain in traumatic brain injury. Higher doses of the fusion protein would sequester essentially 100% of the TNFα in brain in pathologic conditions.

In summary, the experimentation demonstrates that the re-engineering of a model decoy receptor pharmaceutical, the TNFR, as a fusion protein with a BBB molecular Trojan horse, the HIRMAb, produces a new chemical entity that rapidly penetrates the BBB in vivo. In contrast, the TNFR:Fc fusion protein, which represents the present state of the art, does not cross the BBB. The cerebral concentrations of the HIRMAb-TNFR fusion protein that are generated following the administration of relatively low systemic doses is sufficient to sequester nearly all of the target cytokine in the brain in pathologic conditions.

Example 10

Variation of Human Constant Regions

Figure 11:
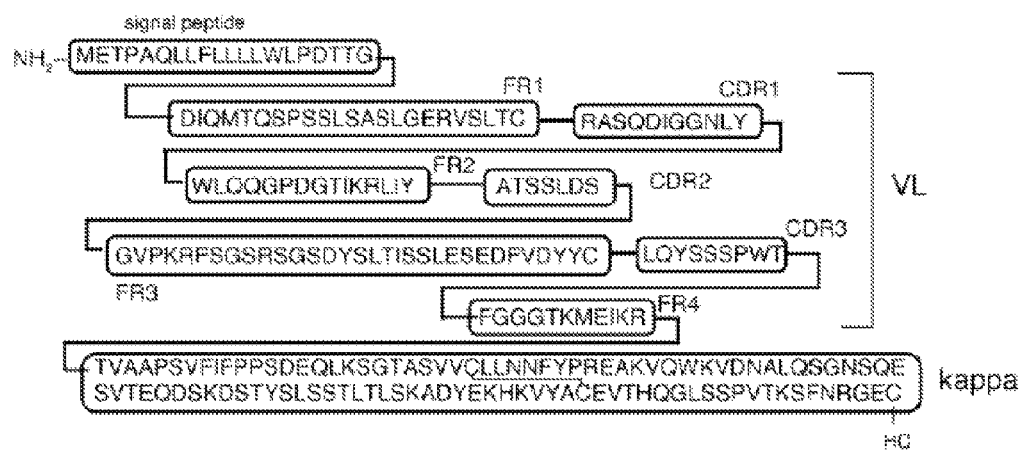
FIG. 11. Domain structure of light chain of the HIRMAb-TNFR fusion protein (SEQ ID NO 6). The 20 amino acid IgG signal peptide (SEQ ID NO 25) is followed by the VL of the HIRMAb light chain, which is comprised of 3 CDRs (CDR1, CDR2, CDR3 (SEQ ID NOS 27, 29 and 31, respectively, in order of appearance)) and 4 FRs (FR1, FR2, FR3, FR4 (SEQ ID NOS 26, 28, 30 and 32, respectively, in order of appearance)), which is followed by the human kappa light chain C-region (SEQ ID NO 33).

The domain structure of the HC of the fusion protein, including the complementarity determining regions (CDRs) and framework regions (FR) of the chimeric HIRMAb HC are given in FIG. 10. The constant region is also shown in FIG. 10, and is derived from human IgG1. The amino acid sequence of the C-region comprising the CH1, hinge, CH2, and CH3 domains is given in FIG. 10. The domain structure of the LC, including the CDRs and FRs of the chimeric HIRMAb LC is given in FIG. 11. The constant region is derived from human kappa LC, and the amino acid sequence comprising the human kappa constant region is shown in FIG. 11.

The constant (C)-region of the HIRMAb HC-TNFR fusion protein is comprised of amino acids 133 to 461 of SEQ ID NO. 4, and is derived from the human IgG1 isotype. In addition, the heavy chain C-region could be derived from the C-region of other human IgG isotypes, including human IgG2, IgG3, and IgG4. The different C-region isotypes each offer well known advantages or disadvantages pertaining to flexibility around the hinge region, protease sensitivity, activation of complement or binding to the Fc receptor. The C-region of the HIRMAb LC is comprised of amino acids 129 to 234 in SEQ ID NO. 6, and is from the human kappa isotype. In addition, the light chain C-region could be derived from the human lambda light chain isotype.

Example 11

Treatment of Brain Diseases with the HIRMAb-TNFR Fusion Protein

Tumor necrosis factor (TNF)-α is a pro-inflammatory cytokine that plays a pathogenetic role in acute and chronic disorders of the brain. Both TNF-α, and the TNFR are up-regulated in brain ischemia (Lambertsen et al, (2007) *Neurosci.*, 144:934-949). The trans-cranial administration of the TNFR extracellular domain (ECD) reduces the size of the infarct in a middle cerebral artery occlusion (MCAO) model (Nawashiro et al, (1997), *Brain Res.*, 778:265-271). The TNFR ECD must be injected directly into brain, because the soluble decoy receptor is a large molecule that does not cross the blood-brain barrier (BBB). In spinal cord injury (SCI), the intra-thecal administration of a fusion protein of human IgG1 Fc fragment and the ECD of the human TNFR type II reduces the neuropathic pain associated with the SCI (Marchand et al, (2008), *Eur. J. Pain*, 1-12). Similarly, the trans-cranial administration of the TNFR-II:Fc fusion protein in a traumatic brain injury (TBI) model is therapeutic (Knoblach et al, (1999), *J. Neuroimmunol.*, 95:115-125). However, the intravenous administration of the TNFR:Fc fusion protein in TBI is not therapeutic (Knoblach et al, (1999), *J. Neuroimmunol.*, 95:115-125), because the molecule does not cross the BBB. In addition to acute brain disorders, such as ischemia or brain or spinal cord injury, the use of the BBB transportable TNFR:Fc fusion proteins may also be therapeutic in chronic neurodegeneration (Tweedie et al, (2007), *Curr. Alzheimer Res.*, 4:375-378).

Example 12

Treatment of Brain Cancer with a MAb-VEGFR Decoy Receptor Fusion Protein

A decoy vascular endothelial growth factor (VEGF) receptor (VEGF):Fc fusion protein can be engineered and expressed (Holash et al, (2002), *Proc. Natl. Acad. Sci. USA*, 99:11393-11398). The VEGF:Fc fusion protein would be expected to sequester endogenous VEGF, which is a growth factor for new vessel growth. Such pharmaceuticals may have particular use as anti-angiogenesis factors in cancer, including brain cancer. However, the VEGF:Fc fusion protein is a large molecule drug, which would not be expected to cross the BBB (Pardridge, (2008), *Bioconj. Chem.*, (19: 1327-1338). What is needed is a re-engineering of the VEGFR decoy receptor as an IgG fusion protein, such as that depicted in FIG. 1 for the TNFR. Such a form of the VEGF would penetrate the human BBB via transport on the endogenous insulin receptor. Once across the BBB, the MAb-VEGR fusion protein would then sequester VEGF within the brain, behind the BBB, and reduce new vessel growth in brain cancer.

Example 13

Treatment of Brain Ischemia with a MAb-Fn14 Decoy Receptor Fusion Protein

Tumor necrosis factor-like weak inducer of apoptosis (TWEAK) is a member of the TNF gene family. The TWEAK receptor is a membrane protein called Fn14. Soluble Fn14 decoy receptors have been engineered as Fc fusion proteins, wherein the ECD of the Fn14 is fused to the amino terminus of the human IgG1 Fc fragment. The TWEAK:Fc fusion protein reduces the size of the stroke in a middle cerebral artery occlusion model; the TWEAK:Fc fusion protein must be administered to the brain via a trans-cranial injection (Yepes et al, (2005), *Am. J. Pathol.*, 166:511-520; Zhang et al, (2007), *J. Cereb. Blood Flow Metab.*, 27:534-544), since this large molecule pharmaceutical does not cross the BBB. However, it is not practical to drill a hole in the head to administer acute stroke therapies in humans. Therefore, what is needed is a re-engineering of the Fn14 decoy receptor as an IgG-Fn14 fusion protein, wherein the Fn14 ECD is fused to the carboxyl terminus of a BBB penetrating IgG, such as that shown in FIG. 1. Such a protein could be given non-invasively via intravenous injection, followed by receptor-mediated transport across the BBB into the ischemic brain.

Example 14

Treatment of Multiple Sclerosis with a MAb-LtαR Decoy Receptor Fusion Protein

Lymphotoxin α (LTα) is also known as TNFα, and can form a hetero-trimeric complex in the membrane with lymphotoxin β (Ltβ). The Ltβcomplex activates the Ltβ receptor (LtβR) to initiate intracellular signal transduction phenomenon and an inflammatory cascade. The LtβR ECD may act as a decoy receptor and sequester endogenous Ltβ, which could be therapeutic in brain disease. A LtβR:Fc fusion protein is therapeutic in experimental demyelination (Plant et al, 2007), and may be therapeutic in human demyelination, such as multiple sclerosis. However, a LtβR:Fc fusion protein would not be expected to cross the human BBB. The LtβR decoy receptor can be re-engineered as a MAb-LtβR fusion protein, such as that depicted in FIG. 1. Such a fusion protein would cross the BBB and sequester endogenous Ltβ within the brain, behind the BBB.

Example 15

Treatment of Neuro-AIDS with a MAb-TRAIL-R Decoy Receptor Fusion Protein

TNF-related apoptosis-inducing ligand (TRAIL) is an inflammatory cytokine, and acts via binding to the TRAIL receptor (TRAIL-R). TRAIL plays a pathologic role in the dementia of acquired immune deficiency syndrome (AIDS), following infection of neurons in the brain by the human immunodeficiency virus (HIV)-1 (Ryan et al, (2004), *J. Neuroimmunol.*, 148:127-139). A new approach to the treatment of the neurological manifestations of AIDS, or neuro-AIDS, may be the sequestration of TRAIL in brain with a soluble TRAIL-R decoy receptor. However, the ECD of the TRAIL-R, or its Fc fusion protein would not penetrate the brain, owing to lack of transport across the BBB. This problem could be solved by re-engineering the TRAIL-R decoy receptor as a MAb-TRAIL-R fusion protein, such as that depicted in FIG. 1. The MAb-TRAIL-R fusion protein would undergo receptor-mediated transport across the BBB, and enter brain, where the fusion protein would sequester TRAIL within the brain.

Example 16

Treatment of Multiple Sclerosis with a MAb-IL6-R Decoy Receptor Fusion Protein

Inflammatory cytokines, such as interleukin (IL)-6, may play a role in demyleinating diseases, such as experimental autoimmune encephalomyelitis (EAE), or multiple sclerosis. The IL-6 receptor (IL-6R) could suppress the action of endogenous IL-6 within the brain following the administration of a soluble IL-6R decoy receptor protein. The administration of the IL-6R:Fc fusion protein, wherein the ECD of IL-6R is fused to the amino terminus of the human IgG1 Fc fragment, is therapeutic in EAE (Linker et al, (2008), *J. Neuroimmunol.*, 205:64-72). However, the penetration of the IL-6R:Fc fusion protein into the brain in multiple sclerosis may be limited, owing to lack of transport through the BBB in vivo. In contrast, a MAb-IL-6R fusion protein, such as that depicted in FIG. 1, could penetrate the BBB via receptor-mediated transport, and thereby sequester endogenous IL-6 in the brain, behind the BBB.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 3

SEQUENCE LISTING

```
<210> 1
<211> 18
<212> DNA
<213> artificial sequence
<220>
<223> Description of Artificial Sequence: Synthetic DNA
<400> 1
CCTTGCCCGCCCAGGTGG <210> 2
<211> 21
<212> DNA
<213> artificial sequence
<220>
<223> Description of Artificial Sequence: Synthetic DNA
<400> 2
TCAGTCGCCAGTGCTCCCTTC <210> 3
<211> 3193
<212> DNA
<213> artificial sequence
<220>
<223> Description of Artificial Sequence: Synthetic DNA
<400> 3
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCGTTTAAACGGGCCCTCTAGACTCG
AGCGGCCGCCACTGTGCTGGAGCCGCCACCATGGACTGGACCTGGAGGGTGTTCTGCCTGCTTGCAGTGGCCCCCGG
AGCCCACAGCCAGGTTCAGCTGCAGCAGTCTGGACCTGAGCTGGTGAAGCCTGGGGCTTTAGTGAAGATATCCTGCA
AGGCTTCTGGTTACACCTTCACAAACTACGATATACACTGGGTGAAGCAGAGGCCTGGACAGGGACTTGAGTGGATT
GGATGGATTTATCCTGGAGATGGTAGTACTAAGTACAATGAGAAATTCAAGGGCAAGGCCACACTGACTGCAGACAA
ATCCTCCAGCACAGCCTACATGCACCTCAGCAGCCTGACTTCTGAGAAATCTGCAGTCTATTTCTGTGCAAGAGAGT
GGGCTTACTGGGGCCAAGGGACTCTGGTCACTGTCTCTGCAGCTAGCACCAAGGGCCCATCGGTCTTCCCCCTGGCA
CCCTCCTCCAAGAGCACCTCTGGGGGCACAGCGGCCCTGGGCTGCCTGGTCAAGGACTACTTCCCCGAACCGGTGAC
GGTGTCGTGGAACTCAGGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACATCTGCAACGTGAATCACAAGCCC
AGCAACACCAAGGTGGACAAGAAAGTTGAGCCCAAATCTTGTGACAAAACTCACACATGCCCACCGTGCCCAGCACC
TGAACTCCTGGGGGGACCGTCAGTCTTCCTCTTCCCCCCAAAACCCAAGGACACCCTCATGATCTCCCGGACCCCTG
AGGTCACATGCGTGGTGGTGGACGTGAGCCACGAAGACCCTGAGGTCAAGTTCAACTGGTACGTGGACGGCGTGGAG
GTGCATAATGCCAAGACAAAGCCGCGGGAGGAGCAGTACAACAGCACGTACCGTGTGGTCAGCGTCCTCACCGTCCT
GCACCAGGACTGGCTGAATGGCAAGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCCCATCCCGGGATGAGCTGACCAAG
AACCAGGTCAGCCTGACCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTCTACAGCAAGCTCACCG
TGGACAAGAGCAGGTGGCAGCAGGGGAACGTCTTCTCATGCTCCGTGATGCATGAGGCTCTGCACAACCACTACACG
CAGAAGAGCCTCTCCCTGTCTCCTGGTAGTAGTTCCTTGCCCGCCCAGGTGGCATTTACACCCTACGCCCGGAGCC
CGGGAGCACATGCCGGCTCAGAGAATACTATGACCAGACAGCTCAGATGTGCTGCAGCAAGTGCTCGCCGGGCCAAC
ATGCAAAAGTCTTCTGTACCAAGACCTCGGACACCGTGTGTGACTCCTGTGAGGACAGCACATACACCCAGCTCTGG
AACTGGGTTCCCGAGTGCTTGAGCTGTGGCTCCCGCTGTAGCTCTGACCAGGTGGAAACTCAAGCCTGCACTCGGGA
ACAGAACCGCATCTGCACCTGCAGGCCCGGCTGGTACTGCGCGTGAGCAAGCAGGAGGGGTGCCGGCTGTGCGCGC
CGCTGCGCAAGTGCCGCCCGGGCTTCGGCGTGGCCAGACCAGGAACTGAAACATCAGACGTGGTGTGCAAGCCCTGT
GCCCCGGGGACGTTCTCCAACACGACTTCATCCACGGATATTTGCAGGCCCCACCAGATCTGTAACGTGGTGGCCAT
CCCTGGGAATGCAAGCAGGGATGCAGTCTGCACGTCCACGTCCCCCACCCGGAGTATGGCCCCAGGGGCAGTACACT
TACCCCAGCCAGTGTCCACACGATCCCAACACACGCAGCCAACTCCAAAACCCAGCACTGCTCCAAGCACCTCCTTC
CTGCTCCCAATGGGCCCCAGCCCCCCAGCTGAAGGGAGCACTGGCGACTGAAACCCGAGCTCGGTACCAAGCTTAAG
TTTAAACCGCTGATCAGCCTCGACTGTGCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAAATTGCATCGCATTGTCTGAGTAGGTGT
CATTCTATTCTGGGGGGTGGGTGGGGCAGGACAGCAAGGGGGAGGATTGGGAAGACAATAGCAGGCATGCTGGGGA
TGCGGTGGGCTCTATGGCTTCTGAGGCGGAAAGAACCAGCGCTGGCTCTAGGGGGTATCCCCACGCGCCCTGTAGCG
GCGCATTAAGCGCGGCGGGTGTGGTGGTTACGCGCA

<210> 4
<211> 699
```

TABLE 3 -continued
SEQUENCE LISTING

```
<212> PRT
<213> artificial sequence
<220>
<223> Description of Artificial Sequence: Synthetic Protein
<400> 4
MDWTWRVFCLLAVAPGAHSQVQLQQSGPELVKPGALVKISCKASGYTFTNYDIHWVKQRP
GQGLEWIGWIYPGDGSTKYNEKFKGKATLTADKSSSTAYMHLSSLTSEKSAVYFCAREWA
YWGQGTLVTVSAASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGSSSLPAVFATPYAPEPGS
TCRLREYYDQTAQMCCSKCSPGQHAKVFCTKTSDTVCDSCEDSTYTQLWNWVPECLSCGS
RCSSDQVETQACTREQNRICTCRPGWYCALSKQEGCRLCAPLRKCRPGFGVARPGTETSD
VVCKPCAPGTFSNTTSSTDICRPHQICNVVAIPGNASRDAVCTSTSPTRSMAPGAVHLPQ
PVSTRSQHTQPTPKPSTAPSTSFLLPMGPSPPAEGSTGD <210> 5
<211> 1,809
<212> DNA
<213> artificial sequence
<220>
<223> Description of Artificial Sequence: Synthetic DNA
<400> 5
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCGTTTAAACTTAAGCTTGGTACCGA
GCTCGGATCCACTAGTCCAGTGTGGTGGAATTCTGCAGGCCGCCACCATGGAGACCCCCGCCCAGCTGCTGTTCCTG
TTGCTGCTTTGGCTTCCAGATACTACCGGCGACATCCAGATGACCCAGTCTCCATCCTCCTTATCTGCCTCTCTGGG
AGAAAGAGTCAGTCTCACTTGTCGGGCAAGTCAGGACATTGGTGGTAACTTATACTGGCTTCAGCAGGGACCAGATG
GAACTATTAAACGCCTGATCTACGCCACATCCAGTTTAGATTCTGGTGTCCCCAAAAGGTTCAGTGGCAGTAGGTCT
GGGTCAGATTATTCTCTCACCATCAGCAGCCTTGAGTCTGAAGATTTTGTAGACTATTACTGTCTACAGTATTCTAG
TTCTCCGTGGACGTTCGGTGGAGGCACAAAGCTGGAAATAAAACGAACTGTGGCTGCACCATCTGTCTTCATCTTCC
CGCCATCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGCAAGGA
CAGCACCTACAGCCTCAGCAGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGTTAGCTCGAGTCTAGAGGGCCC
GTTTAAACCCGCTGATCAGCCTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCGCATTGTCTGAGTAGGT
GTCATTCTATTCTGGGGGGTGGGGTGGGCAGGACAGCAAGGGGGAGGATTGGGAAGACAATAGCAGGCATGCTGGG
GATGCGGTGGGCTCTATGGCTTCTGAGGCGGAAAGAACCAGCGCTGGCTCTAGGGGGTATCCCCACGCGCCCTGTAG
CGGCGCATTAAGCGCGGCGGGTGTGGTGGTTACGCGCA <210> 6
<211> 234
<212> PRT
<213> artificial sequence
<220>
<223> Description of Artificial Sequence: Synthetic Protein
<400> 6
METPAQLLFLLLLWLPDTTGDIQMTQSPSSLSASLGERVSLTCRASQDIGGNLYWLQQGPDGTIKRLIYATSSLDSG
VPKRFSGSRSGSDYSLTISSLESEDFVDYYCLQYSSSPWTFGGGTKMEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGLSSPVTKSFNR
GEC <210> 7
<211> 699
<212> PRT
<213> artificial sequence
<220>
<223> Description of Artificial Sequence: Synthetic Protein
<400> 7
MDWTWRVFCLLAVAPGAHSQVQLQQSGPELVKPGALVKISCKASGYTFTNYDIHWVKQRP
GQGLEWIGWIYPGDGSTKYNEKFKGKATLTADKSSSTAYMHLSSLTSEKSAVYFCAREWA
YWGQGTLVTVSAASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGSSSLPAVFATPYAPEPGS
TCRLREYYDQTAQMCCSKCSPGQHAKVFCTKTSDTVCDSCEDSTYTQLWNWVPECLSCGS
```

TABLE 3 -continued

```
SEQUENCE LISTING
```

RCSSDQVETQACTREQNRICTCRPGWYCALSKQEGCRLCAPLRKCRPGFGVARPGTETSD
VVCKPCAPGTFSNTTSSTDICRPHQICNVVAIPGNASMDAVCTSTSPTRSMAPGAVHLPQ
PVSTRSQHTQPTPEPSTAPSTSFLLPMGPSPPAEGSTGD

```
<210> 8
<211> 31
<212> DNA
<213> artificial sequence
<220>
<223> Description of Artificial Sequence: Synthetic DNA
<400> 8
CTGGGAATGCAAGCATGGATGCAGTCTGCAC <210> 9
<211> 31
<212> DNA
<213> artificial sequence
<220>
<223> Description of Artificial Sequence: Synthetic DNA
<400> 9
GTGCAGACTGCATCCATGCTTGCATTCCCAG <210> 10
<211> 31
<212> DNA
<213> artificial sequence
<220>
<223> Description of Artificial Sequence: Synthetic DNA
<400> 10
ACGCAGCCAACTCCAGAACCCAGCACTGCTC <210> 11
<211> 31
<212> DNA
<213> artificial sequence
<220>
<223> Description of ArtificialSequence: Synthetic DNA
<400> 11
GAGCAGTGCTGGGTTCTGGAGTTGGCTGCGT
```

```
SEQUENCE LISTING
```

```
<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccttgcccgc ccaggtgg                                                 18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcagtcgcca gtgctccctt c                                             21

<210> SEQ ID NO 3
<211> LENGTH: 3193
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 3

```
gttgacattg attattgact agttattaat agtaatcaat tacggggtca ttagttcata        60
gcccatatat ggagttccgc gttacataac ttacggtaaa tggcccgcct ggctgaccgc       120
ccaacgaccc ccgcccattg acgtcaataa tgacgtatgt tcccatagta acgccaatag       180
ggactttcca ttgacgtcaa tgggtggagt atttacggta aactgcccac ttggcagtac       240
atcaagtgta tcatatgcca agtacgcccc ctattgacgt caatgacggt aaatggcccg       300
cctggcatta tgcccagtac atgaccttat ggactttcc tacttggcag tacatctacg       360
tattagtcat cgctattacc atggtgatgc ggttttggca gtacatcaat gggcgtggat       420
agcggtttga ctcacgggga tttccaagtc tccacccat tgacgtcaat gggagtttgt       480
tttggcacca aaatcaacgg gactttccaa aatgtcgtaa caactccgcc ccattgacgc       540
aaatgggcgg taggcgtgta cggtgggagg tctatataag cagagctctc tggctaacta       600
gagaacccac tgcttactgg cttatcgaaa ttaatacgac tcactatagg gagacccaag       660
ctggctagcg tttaaacggg ccctctagac tcgagcggcc gccactgtgc tggagccgcc       720
accatggact ggacctggag ggtgttctgc ctgcttgcag tggcccccgg agcccacagc       780
caggttcagc tgcagcagtc tggacctgag ctggtgaagc ctggggcttt agtgaagata       840
tcctgcaagg cttctggtta caccttcaca aactacgata tacactgggt gaagcagagg       900
cctggacagg gacttgagtg gattggatgg atttatcctg agatggtag tactaagtac       960
aatgagaaat tcaagggcaa ggccacactg actgcagaca atcctccag cacagcctac      1020
atgcacctca gcagcctgac ttctgagaaa tctgcagtct atttctgtgc aagagagtgg      1080
gcttactggg gccaagggac tctggtcact gtctctgcag ctagcaccaa gggcccatcg      1140
gtcttccccc tggcaccctc ctccaagagc acctctgggg gcacagcggc cctgggctgc      1200
ctggtcaagg actacttccc cgaaccggtg acggtgtcgt ggaactcagg cgccctgacc      1260
agcggcgtgc acaccttccc ggctgtccta cagtcctcag gactctactc cctcagcagc      1320
gtggtgaccg tgccctccag cagcttgggc acccagacct acatctgcaa cgtgaatcac      1380
aagcccagca acaccaaggt ggacaagaaa gttgagccca atcttgtgac aaaaactcac      1440
acatgcccac cgtgcccagc acctgaactc ctggggggac cgtcagtctt cctcttcccc      1500
ccaaaaccca aggacaccct catgatctcc cggacccctg aggtcacatg cgtggtggtg      1560
gacgtgagcc acgaagaccc tgaggtcaag ttcaactggt acgtggacgg cgtggaggtg      1620
cataatgcca agacaaagcc gcgggaggag cagtacaaca gcacgtaccg tgtggtcagc      1680
gtcctcaccg tcctgcacca ggactggctg aatggcaagg agtacaagtg caaggtctcc      1740
aacaaagccc tcccagcccc catcgagaaa accatctcca aagccaaagg cagccccga       1800
gaaccacagg tgtacaccct gcccccatcc cgggatgagc tgaccaagaa ccaggtcagc      1860
ctgacctgcc tggtcaaagg cttctatccc agcgacatcg ccgtggagtg ggagagcaat      1920
gggcagccgg agaacaacta caagaccacg cctcccgtgc tggactccga cggctccttc      1980
ttcctctaca gcaagctcac cgtggacaag agcaggtggc agcagggaa cgtcttctca       2040
tgctccgtga tgcatgaggc tctgcacaac cactacacgc agaagagcct ctccctgtct      2100
cctggtagta gttccttgcc cgcccaggtg gcatttacac cctacgcccc ggagcccggg      2160
```

-continued

```
agcacatgcc ggctcagaga atactatgac cagacagctc agatgtgctg cagcaagtgc    2220
tcgccgggcc aacatgcaaa agtcttctgt accaagacct cggacaccgt gtgtgactcc    2280
tgtgaggaca gcacatacac ccagctctgg aactgggttc ccgagtgctt gagctgtggc    2340
tcccgctgta gctctgacca ggtggaaact caagcctgca ctcgggaaca gaaccgcatc    2400
tgcacctgca ggcccggctg gtactgcgcg ctgagcaagc aggaggggtg ccggctgtgc    2460
gcgccgctgc gcaagtgccg cccgggcttc ggcgtggcca gaccaggaac tgaaacatca    2520
gacgtggtgt gcaagccctg tccccgggga cgttctcca acacgacttc atccacggat    2580
atttgcaggc cccaccagat ctgtaacgtg gtggccatcc ctgggaatgc aagcagggat    2640
gcagtctgca cgtccacgtc ccccacccgg agtatggccc caggggcagt acacttaccc    2700
cagccagtgt ccacacgatc ccaacacacg cagccaactc caaaacccag cactgctcca    2760
agcacctcct tcctgctccc aatgggcccc agccccccag ctgaagggag cactggcgac    2820
tgaaacccga gctcggtacc aagcttaagt ttaaaccgct gatcagcctc gactgtgcct    2880
tctagttgcc agccatctgt tgtttgcccc tcccccgtgc cttccttgac cctggaaggt    2940
gccactccca ctgtcctttc ctaataaaat gaggaaattg catcgcattg tctgagtagg    3000
tgtcattcta ttctgggggg tggggtgggg caggacagca aggggagga ttgggaagac    3060
aatagcaggc atgctgggga tgcggtgggc tctatggctt ctgaggcgga agaaccagc    3120
gctggctcta gggggtatcc ccacgcgccc tgtagcggcg cattaagcgc ggcgggtgtg    3180
gtggttacgc gca                                                       3193
```

<210> SEQ ID NO 4
<211> LENGTH: 699
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
                20                  25                  30

Pro Gly Ala Leu Val Lys Ile Ser Cys Lys Ala Ser Gly Tyr Thr Phe
            35                  40                  45

Thr Asn Tyr Asp Ile His Trp Val Lys Gln Arg Pro Gly Gln Gly Leu
        50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175
```

```
Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Ser Ser Ser
450                 455                 460

Leu Pro Ala Gln Val Ala Phe Thr Pro Tyr Ala Pro Glu Pro Gly Ser
465                 470                 475                 480

Thr Cys Arg Leu Arg Glu Tyr Tyr Asp Gln Thr Ala Gln Met Cys Cys
                485                 490                 495

Ser Lys Cys Ser Pro Gly Gln His Ala Lys Val Phe Cys Thr Lys Thr
            500                 505                 510

Ser Asp Thr Val Cys Asp Ser Cys Glu Asp Ser Thr Tyr Thr Gln Leu
            515                 520                 525

Trp Asn Trp Val Pro Glu Cys Leu Ser Cys Gly Ser Arg Cys Ser Ser
            530                 535                 540

Asp Gln Val Glu Thr Gln Ala Cys Thr Arg Glu Gln Asn Arg Ile Cys
545                 550                 555                 560

Thr Cys Arg Pro Gly Trp Tyr Cys Ala Leu Ser Lys Gln Glu Gly Cys
                565                 570                 575

Arg Leu Cys Ala Pro Leu Arg Lys Cys Arg Pro Gly Phe Gly Val Ala
            580                 585                 590
```

```
Arg Pro Gly Thr Glu Thr Ser Asp Val Val Cys Lys Pro Cys Ala Pro
            595                 600                 605
Gly Thr Phe Ser Asn Thr Thr Ser Ser Thr Asp Ile Cys Arg Pro His
    610                 615                 620
Gln Ile Cys Asn Val Val Ala Ile Pro Gly Asn Ala Ser Arg Asp Ala
625                 630                 635                 640
Val Cys Thr Ser Thr Ser Pro Thr Arg Ser Met Ala Pro Gly Ala Val
                645                 650                 655
His Leu Pro Gln Pro Val Ser Thr Arg Ser Gln His Thr Gln Pro Thr
            660                 665                 670
Pro Lys Pro Ser Thr Ala Pro Ser Thr Ser Phe Leu Leu Pro Met Gly
            675                 680                 685
Pro Ser Pro Pro Ala Glu Gly Ser Thr Gly Asp
            690                 695

<210> SEQ ID NO 5
<211> LENGTH: 1809
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctctc tggctaacta     600
gagaacccac tgcttactgg cttatcgaaa ttaatacgac tcactatagg gagacccaag     660
ctggctagcg tttaaactta agcttggtac cgagctcgga tccactagtc cagtgtggtg     720
gaattctgca gccgccacc atggagaccc cgcccagct gctgttcctg ttgctgcttt      780
ggcttccaga tactaccggc gacatccaga tgacccagtc tccatcctcc ttatctgcct     840
ctctgggaga aagagtcagt ctcacttgtc gggcaagtca ggacattggt gtaaacttat     900
actggcttca gcagggacca gatggaacta ttaaacgcct gatctacgcc acatccagtt     960
tagattctgg tgtcccaaa aggttcagtg cagtaggtc tggtcagat tattctctca      1020
ccatcagcag ccttgagtct gaagatttg tagactatta ctgtctacag tattctagtt     1080
ctccgtggac gttcggtgga ggcacaaagc tggaaataaa acgaactgtg gctgcaccat     1140
ctgtcttcat cttcccgcca tctgatgagc agttgaaatc tggaactgcc tctgttgtgt     1200
gcctgctgaa taacttctat cccagagagg ccaaagtaca gtggaaggtg gataacgccc     1260
tccaatcggg taactcccag gagagtgtca cagagcagga cagcaaggac agcacctaca     1320
gcctcagcag caccctgacg ctgagcaaag cagactacga gaaacacaaa gtctacgcct     1380
gcgaagtcac ccatcagggc ctgagctcgc ccgtcacaaa gagcttcaac aggggagagt     1440
```

-continued

```
gttagctcga gtctagaggg cccgtttaaa cccgctgatc agcctcgact gtgccttcta   1500
gttgccagcc atctgttgtt tgcccctccc ccgtgccttc cttgaccctg gaaggtgcca   1560
ctcccactgt cctttcctaa taaaatgagg aaattgcatc gcattgtctg agtaggtgtc   1620
attctattct gggggggtggg gtggggcagg acagcaaggg ggaggattgg gaagacaata   1680
gcaggcatgc tggggatgcg gtgggctcta tggcttctga ggcggaaaga accagcgctg   1740
gctctagggg gtatcccac gcgccctgta gcggcgcatt aagcgcggcg ggtgtggtgg   1800
ttacgcgca                                                            1809
```

<210> SEQ ID NO 6
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Gly Thr Lys Met Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 7
<211> LENGTH: 699
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
```

-continued

```
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Ser Ser Ser
    450                 455                 460
Leu Pro Ala Gln Val Ala Phe Thr Pro Tyr Ala Pro Glu Pro Gly Ser
465                 470                 475                 480
Thr Cys Arg Leu Arg Glu Tyr Tyr Asp Gln Thr Ala Gln Met Cys Cys
                485                 490                 495
Ser Lys Cys Ser Pro Gly Gln His Ala Lys Val Phe Cys Thr Lys Thr
            500                 505                 510
Ser Asp Thr Val Cys Asp Ser Cys Glu Asp Ser Thr Tyr Thr Gln Leu
        515                 520                 525
Trp Asn Trp Val Pro Glu Cys Leu Ser Cys Gly Ser Arg Cys Ser Ser
    530                 535                 540
Asp Gln Val Glu Thr Gln Ala Cys Thr Arg Glu Gln Asn Arg Ile Cys
545                 550                 555                 560
Thr Cys Arg Pro Gly Trp Tyr Cys Ala Leu Ser Lys Gln Glu Gly Cys
                565                 570                 575
Arg Leu Cys Ala Pro Leu Arg Lys Cys Arg Pro Gly Phe Gly Val Ala
            580                 585                 590
Arg Pro Gly Thr Glu Thr Ser Asp Val Val Cys Lys Pro Cys Ala Pro
        595                 600                 605
Gly Thr Phe Ser Asn Thr Thr Ser Ser Thr Asp Ile Cys Arg Pro His
    610                 615                 620
Gln Ile Cys Asn Val Val Ala Ile Pro Gly Asn Ala Ser Met Asp Ala
625                 630                 635                 640
Val Cys Thr Ser Thr Ser Pro Thr Arg Ser Met Ala Pro Gly Ala Val
                645                 650                 655
His Leu Pro Gln Pro Val Ser Thr Arg Ser Gln His Thr Gln Pro Thr
            660                 665                 670
Pro Glu Pro Ser Thr Ala Pro Ser Thr Ser Phe Leu Leu Pro Met Gly
        675                 680                 685
Pro Ser Pro Pro Ala Glu Gly Ser Thr Gly Asp
    690                 695
```

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgggaatgc aagcatggat gcagtctgca c                                    31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

-continued gtgcagactg catccatgct tgcattccca g                                31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgcagccaa ctccagaacc cagcactgct c                                31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagcagtgct gggttctgga gttggctgcg t                                31

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Asp Trp Thr Trp Arg Val Phe Cys Leu Leu Ala Val Ala Pro Gly
1               5                   10                  15

Ala His Ser

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Val Gln Leu Gln Gln Ser Gly Pro Glu Leu Val Lys Pro Gly Ala
1               5                   10                  15

Leu Val Lys Ile Ser Cys Lys Ala Ser
            20                  25

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Tyr Thr Phe Thr Asn Tyr Asp Ile His
1               5                   10

<210> SEQ ID NO 15
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Val Lys Gln Arg Pro Gly Gln Gly Leu Glu Trp Ile Gly
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Tyr Pro Gly Asp Gly Ser Thr Lys Tyr Asn Glu Lys Phe Lys
1               5                   10                  15

Gly

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Ala Thr Leu Thr Ala Asp Lys Ser Ser Ser Thr Ala Tyr Met His
1               5                   10                  15

Leu Ser Ser Leu Thr Ser Glu Lys Ser Ala Val Tyr Phe Cys Ala Arg
            20                  25                  30

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Trp Ala Tyr
1

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Gly Gln Gly Thr Leu Val Thr Val Ser Ala
1               5                   10

<210> SEQ ID NO 20
<211> LENGTH: 98
<212> TYPE: PRT
<213> ORGANISM: Homo sapiens

<400> SEQUENCE: 20
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 21
<211> LENGTH: 12
<212> TYPE: PRT
<213> ORGANISM: Homo sapiens

<400> SEQUENCE: 21

Glu Pro Lys Ser Cys Asp Lys Thr His Thr Cys Pro
1               5                   10

<210> SEQ ID NO 22
<211> LENGTH: 113
<212> TYPE: PRT
<213> ORGANISM: Homo sapiens

<400> SEQUENCE: 22

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 23
<211> LENGTH: 106
<212> TYPE: PRT
<213> ORGANISM: Homo sapiens

<400> SEQUENCE: 23

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45
```

```
Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105
```

<210> SEQ ID NO 24
<211> LENGTH: 235
<212> TYPE: PRT
<213> ORGANISM: Homo sapiens

<400> SEQUENCE: 24

```
Leu Pro Ala Gln Val Ala Phe Thr Pro Tyr Ala Pro Glu Pro Gly Ser
 1               5                  10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Arg Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Lys Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Met Glu Thr Pro Ala Gln Leu Leu Phe Leu Leu Leu Leu Trp Leu Pro
 1               5                  10                  15
```

```
Asp Thr Thr Gly
            20

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Ile Gln Met Thr Gln Ser Pro Ser Ser Leu Ser Ala Ser Leu Gly
1               5                   10                  15
Glu Arg Val Ser Leu Thr Cys
            20

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ala Ser Gln Asp Ile Gly Gly Asn Leu Tyr
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Leu Gln Gln Gly Pro Asp Gly Thr Ile Lys Arg Leu Ile Tyr
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Thr Ser Ser Leu Asp Ser
1               5

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Val Pro Lys Arg Phe Ser Gly Ser Arg Ser Gly Ser Asp Tyr Ser
1               5                   10                  15
Leu Thr Ile Ser Ser Leu Glu Ser Glu Asp Phe Val Asp Tyr Tyr Cys
            20                  25                  30
```

```
<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Gln Tyr Ser Ser Ser Pro Trp Thr
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Gly Gly Gly Thr Lys Met Glu Ile Lys Arg
1               5                   10

<210> SEQ ID NO 33
<211> LENGTH: 106
<212> TYPE: PRT
<213> ORGANISM: Homo sapiens

<400> SEQUENCE: 33

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

What is claimed:

1. A HIRMAb-TNFR bifunctional decoy receptor fusion antibody comprising two fusion heavy chains of SEQ ID NO:4, and two light chains of SEQ ID NO:6.

\* \* \* \* \*